(12) United States Patent
Player et al.

(10) Patent No.: US 7,829,584 B2
(45) Date of Patent: Nov. 9, 2010

(54) PYRIDINES AND PYRIDINE N-OXIDES AS MODULATORS OF THROMBIN

(75) Inventors: Mark R. Player, Phoenixville, PA (US); Tianbao Lu, Churchville, PA (US); Huaping Hu, Pennington, NJ (US); Xizhen Zhu, Monmouth Junction, NJ (US); Christopher Teleha, Fort Washington, PA (US); Kevin Kreutter, Plainsboro, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 886 days.

(21) Appl. No.: 11/685,544

(22) Filed: Mar. 13, 2007

(65) Prior Publication Data

US 2007/0225282 A1    Sep. 27, 2007

Related U.S. Application Data

(60) Provisional application No. 60/784,361, filed on Mar. 21, 2006.

(51) Int. Cl.
C07D 213/00 (2006.01)
A61K 31/44 (2006.01)

(52) U.S. Cl. ................................ 514/332; 546/265

(58) Field of Classification Search ................ None
See application file for complete search history.

(56) References Cited

U.S. PATENT DOCUMENTS

| | | | |
|---|---|---|---|
| 4,652,440 A | 3/1987 | Paik et al. | |
| 4,727,064 A | 2/1988 | Pitha | |
| 4,764,604 A | 8/1988 | Muller | |
| 4,957,939 A | 9/1990 | Gries et al. | |
| 5,024,998 A | 6/1991 | Bodor | |
| 5,122,361 A | 6/1992 | Kung et al. | |
| 2003/0158218 A1 | 8/2003 | Nantermet et al. | |

FOREIGN PATENT DOCUMENTS

| | | |
|---|---|---|
| CA | 2164684 | 12/1994 |
| EP | 759429 | 2/1997 |
| EP | 761241 | 3/1997 |
| EP | 604022 | 6/2007 |
| WO | WO96/11668 | 4/1996 |
| WO | WO96/32143 | 10/1996 |
| WO | WO96/38136 | 12/1996 |
| WO | WO2004/091613 | 10/2004 |

OTHER PUBLICATIONS

Naterme, P.G. et al., "P2 pyridine N-oxide thrombin inhibitors a novel peptidomimetic scaffold", Bioorganic & Medicinal Chemistry Letters, vol. 15, Apr. 2005, pp. 2771-2775.
*Angewandte Chemie* 92:390-391, 1980.
*Biochem Pharmacol* 22: 3099-3108, Cheng Y and Prusoff WH (1973).

*Bioorg. Med Chem. Lett.* 15:2771, 2005.
*Bioorg. Med. Chem.* 10:1115-1122, 2002.
*Bioorg. Med. Chem.* 6:1631-1639, '1998.
*Can. J. Physiol. Pharmacol.* 77:79-88, 1999.
*Chem. Pharm. Bull.* 48:982-990, 2000.
*Chem. Soc. Rev.* 3:513-544, 1974.
*Chemico-Biological Interactions* 117:191-217, 1999.
*Collect. Czech. Chem. Commun.* 45:504-516, 1980.
*Collect. Czech. Chem. Commun.* 64:649-672, 1999.
*Helv. Chim. Acta* 59:229-235, 1976.
*Helv. Chim. Acta* 77:1057-1064, 1994.
*Heterocycles* 36:431-434, 1993), VII-3.
*J. Am. Chem. Soc.* 105:7435-7442, 1983.
*J. Am. Chem. Soc.* 118:2521-2522, 1996.
*J. Am. Chem. Soc.* 122:712-713, 2000.
*J. Am. Chem. Soc.* 125:12110-12111, 2003.
*J. Antibiotics* 53:1086-1095, 2000.
*Biol. Chem.* 121:235-253, 1937.
*J. Biol. Chem.* 280:19496-19506, 2005.
*J. Chem. Soc. C: Organic* 1375-1380, 1970), VII-4.
*J. Fluorine Chem.* 18:497-506, 1981.
*J. Heterocycl. Chem.* 34:145-151, 1997.
*J. Heterocycl. Chem.* 38:1297-1306, 2001.
*J. Labelled. Compd. Radiopharm.* 45:423-434, 2002.
*J. Med. Chem.* 39:892-903, 1996.
*J. Med. Chem.* 43:1754-1764, 2000.
*J. Med. Chem.* 45:2841-2849, 2002.
*J. Med. Chem.* 45:3639-3648, 2002.
*J. Med. Chem.* 45:4755-4761, 2002.
*J. Med. Chem.* 46:461-473, 2003.
*J. Med. Chem.* 47:612-626, 2004.
*J. Org. Chem.* 20:6781-6789, 2004.

(Continued)

*Primary Examiner*—Zinna N Davis
(74) *Attorney, Agent, or Firm*—Thomas J. Dodd

(57) ABSTRACT

The present invention describes compounds of Formula I:

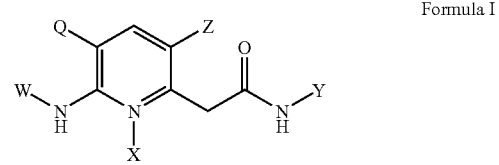

Formula I wherein W, X, Y, Z, and Q are defined herein, or a pharmaceutically acceptable salt thereof, for the prophylaxis, or treatment of diseases and conditions related to thrombin activity in a mammal.

10 Claims, No Drawings

OTHER PUBLICATIONS

*J. Org. Chem.* 22:7752-7754, 2004.
*J. Org. Chem.* 51:1889-1891, 1986.
*J. Org. Chem.* 55:541-548, 1990.
*J. Org. Chem.* 58:4642-4645, 1993.
*J. Org. Chem.* 60:1408-1412, 1995.
*J. Org. Chem.* 65:1158-1174, 2000.
*J. Org. Chem.* 67:6550-6552, 2002.
*J. Org. Chem.* 67:674-683, 2002.
*J. Org. Chem.* 68:8838-8846, 2003.
*J. Pharm. Sci.* 62:1900-1902, 1973.
*J. Pharmaceutical Sci.* 64:367-391, 1975.
*Journal of Heterocyclic Chemistry*, 21:673-679, 1984.
Khaw et al., *Science* 209:295-297, (1980).
*Labelled Compd. Radiopharm.* 36:685-699, 1995.
*Life Sciences* 8:1123-1128, 1969.
*Med. Chem.* 45:461-473, 2003.
*Org. Lett.* 2:3425-3427, 2000.
*Org. Process Res. Dev.* 8:192, 2004.
*Organic Process Research & Development* 8:192-200, 2004.
*Tetrahedron* 57:5321-5326, 2001.
*Tetrahedron Lett.* 39:5159-5162, 1998.
*Tetrahedron Lett.* 40:2481-2484, 1999.
*Tetrahedron Lett.* 46:135-137, 2005.
United States Pharmacopeia/National Formulary for 1995, pp. 1636-1637, published by United States Pharmacopeial Convention, Inc., Rockville, Maryland (1994).
*Chem. Pharm. Bull.* 47:1013, 1999.

PYRIDINES AND PYRIDINE N-OXIDES AS MODULATORS OF THROMBIN

CROSS REFERENCE TO RELATED APPLICATIONS

This present application claims benefit of U.S. Provisional Patent Application Ser. No. 60/784361, filed Mar. 21, 2006, which is incorporated herein by reference in its entirety and for all purposes.

FIELD OF THE INVENTION

The present invention relates to novel compounds that function as thrombin inhibitors.

BACKGROUND OF THE INVENTION

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor, and autoamplifies its own production through a feedback mechanism. Thus, inhibitors of thrombin function have therapeutic potential in a host of cardiovascular and non-cardiovascular diseases.

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi. In addition, the use of the paramagnetic contrasting agent, gadolinium diethylenetriaminepentaacetic acid in magnetic resonance imaging of patients treated by thrombolysis for acute myocardial infarction has been reported.

A need continues to exist for non-peptidic compounds that are potent and selective protease inhibitors, and which possess greater bioavailability and fewer side-effects than currently available protease inhibitors. Accordingly, new protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to the novel compounds of Formula I:

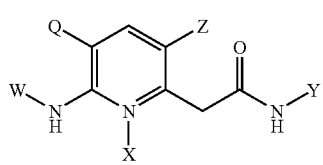

Formula I wherein

Z is H, F, Cl, Br, —CN, $C_{(1-4)}$alkyl, —C≡CH, —C≡CCH$_3$, or —C≡CCH$_2$CH$_3$;

X is absent or oxygen;

Q is H or F;

W is —CH$_2$C(R$^1$)$_2$R$^2$;

R$^1$ is independently hydrogen, C$_{1-4}$ alkyl, halogen, or both R$^1$ may be taken together to form a C$_{(3-6)}$cycloalkyl ring;

R$^2$ is heterocyclyl (preferably piperidinyl), phenyl, 4-fluorophenyl, 4-fluoroheteroaryl (preferably 4-fluoropyridyl, 4-fluoropyridyl-N-oxide), or heteroaryl (preferably pyridinyl, pyrimidinyl, pyridinyl-N-oxide), wherein said phenyl or 4-fluorophenyl is optionally substituted with one R$^3$;

R$^3$ is —C$_{(1-4)}$alkyl, —CF$_3$, —Cl, —F, —Br, —CO$_2$H, —CH$_2$CO$_2$H, —CO$_2$Et, —CH$_2$CO$_2$Et, —CH$_2$NHCH$_2$CO$_2$H, —CH$_2$NHCH$_2$CO$_2$Et,

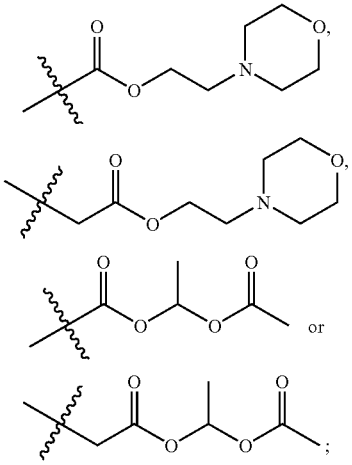

Y is selected from the group consisting of:

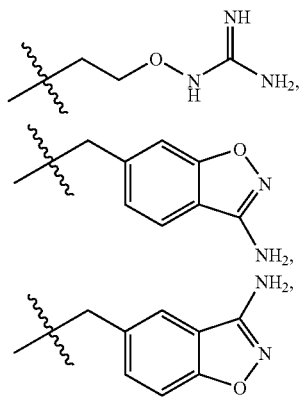

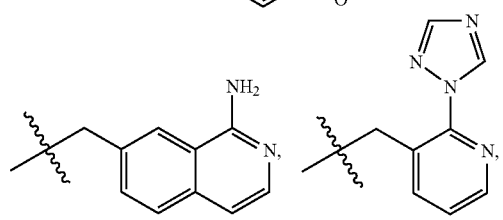

-continued

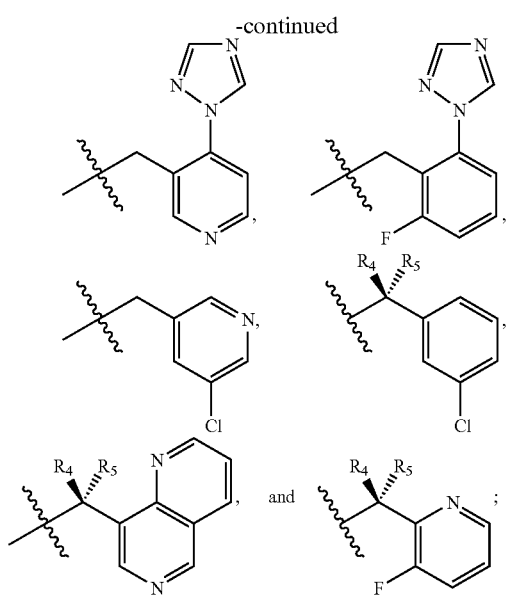

$R_4$ and $R_5$ are independently H or D (deuterium), provided that at least one of $R_4$ and $R_5$ is deuterium.

Also provided are processes for preparing the compounds of Formula I. The novel compounds of the present invention are potent inhibitors of thrombin.

Also provided are methods of treating thrombosis in a mammal by administering an effective amount of a compound of Formula I.

The invention includes a composition for inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods for treating myocardial infarction; unstable angina; stroke; restenosis; deep vein thrombosis; disseminated intravascular coagulation caused by trauma, or septic hemodialysis; cardiopulmonary bypass surgery; adult respiratory distress syndrome; endotoxic shock; hypercoagulability during chemotherapy; Alzheimer's disease; and fibrin formation in the eye. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes compositions which are useful for in vivo imaging of thrombi in a mammal, comprising a compound of the present invention which is capable of being detected from outside the body. Preferred are compositions comprising a compound of the present invention and a detectable label, such as a radioactive or paramagnetic atom.

In another aspect, the present invention provides diagnostic compositions which are useful for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

DETAILED DESCRIPTION OF THE INVENTION

The present invention is directed to the novel compounds of Formula I:

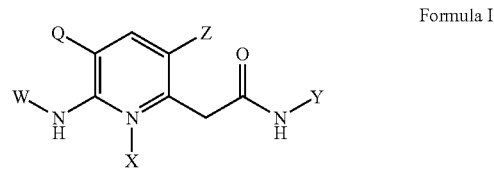

Formula I wherein

Z is H, F, Cl, Br, —CN, $C_{(1-4)}$alkyl, —C≡C—H, —C≡C—CH$_3$, or —C≡C—CH$_2$CH$_3$;

X is absent or oxygen;

Q is H, or F;

W is —CH$_2$C(R$^1$)$_2$R$^2$;

R$^1$ is independently hydrogen, $C_{1-4}$ alkyl, halogen, or both R$^1$ may be taken together to form a $C_{(3-6)}$cycloalkyl ring;

R$_2$ is heterocyclyl, phenyl, 4-fluorophenyl, 4-fluoroheteroaryl, or heteroaryl, wherein said phenyl or 4-fluorophenyl is optionally substituted with one R$^3$;

R$^3$ is —$C_{(1-4)}$alkyl, —CF$_3$, —Cl, —F, —Br, —CO$_2$H, —CH$_2$CO$_2$H, —CO$_2$Et, —CH$_2$CO$_2$Et, —CH$_2$NHCH$_2$CO$_2$H, —CH$_2$NHCH$_2$CO$_2$Et,

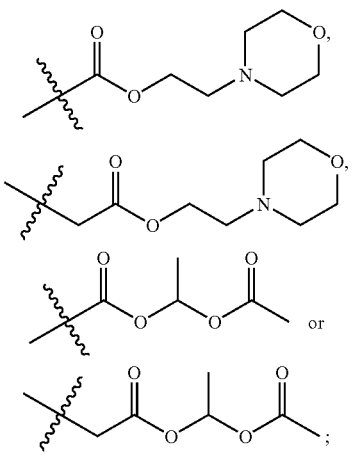

Y is selected from the group consisting of:

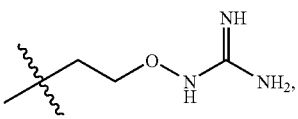

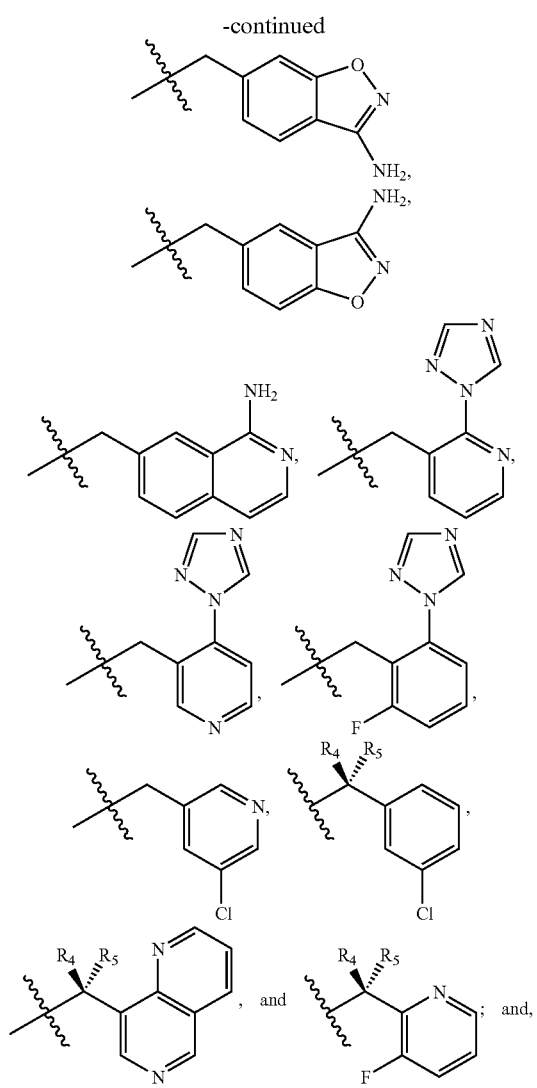

R$_4$ and R$_5$ are independently H or D (deuterium), provided that at least one of R$_4$ and R$_5$ is deuterium.

Also provided are processes for preparing the compounds of Formula I. The novel compounds of the present invention are potent inhibitors of thrombin.

Also provided are methods of treating thrombosis in a mammal by administering an effective amount of a compound of Formula I.

In an embodiment of the invention, one or more of the following limitations are present:

Z is H, F, Cl, Br, —CN, C$_{(1-4)}$alkyl, —C≡C—H, —C≡C—CH$_3$, or —C≡C—CH$_2$CH$_3$;

X is absent or oxygen;

Q is H, or F;

W is —CH$_2$C(R$^1$)$_2$R$^2$;

R$^1$ is independently hydrogen, C$_{1-4}$ alkyl, halogen, or both R$^1$ may be taken together to form a C$_{(3-6)}$cycloalkyl ring;

R$_2$ is heterocyclyl, phenyl, 4-fluorophenyl, 4-fluoroheteroaryl, or heteroaryl, wherein said phenyl or 4-fluorophenyl may be substituted with one R$^3$;

R$^3$ is —C$_{(1-4)}$alkyl, —CF$_3$, —Cl, —F, —Br, —CO$_2$H, —CH$_2$CO$_2$H, —CO$_2$Et, —CH$_2$CO$_2$Et, —CH$_2$NHCH$_2$CO$_2$H, —CH$_2$NHCH$_2$CO$_2$Et, Y is selected from the group consisting of:

In an embodiment of the invention, one or more of the following limitations are present:

Z is H, F, Cl, Br, —CN, C$_{(1-4)}$alkyl, —C≡C—H, —C≡C—CH$_3$, or —C≡C—CH$_2$CH$_3$;

X is absent or oxygen;

Q is H, or F;

W is —CH$_2$C(R$^1$)$_2$R$^2$;

wherein each R$^1$ is independently hydrogen, C$_{1-4}$ alkyl, halogen, or both R$^1$ may be taken together to form a C$_{(3-6)}$ cycloalkyl ring;

R$_2$ is piperidin-2-yl, phenyl, 4-fluorophenyl, pyrimidyl, pyridinyl, or pyridinyl-N-oxide, wherein said phenyl or 4-fluorophenyl is optionally substituted with one R$^3$;

wherein R$^3$ is —C$_{(1-4)}$alkyl, —CF$_3$, —Cl, —F, —Br, —CO$_2$H, —CH$_2$CO$_2$H, —CO$_2$Et, —CH$_2$CO$_2$Et, —CH$_2$NHCH$_2$CO$_2$H, —CH$_2$NHCH$_2$CO$_2$Et,

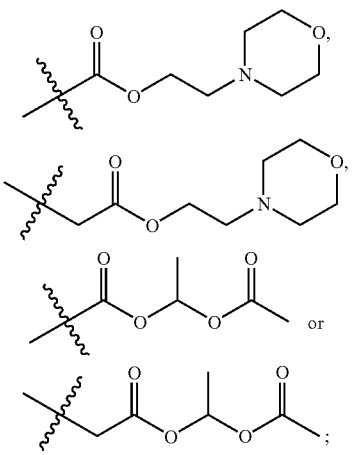

Y is selected from the group consisting of:

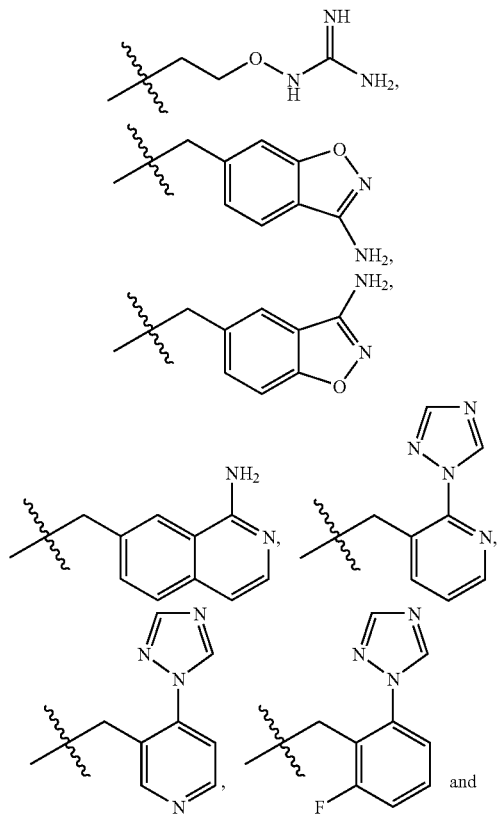

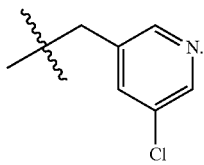

In an embodiment of the invention, one or more of the following limitations are present:

Z is H, F, Cl, Br, —CN, or C$_{(1-4)}$alkyl;

X is absent or oxygen;

Q is H, or F;

W is —CH$_2$C(R$^1$)$_2$R$^2$;

R$^1$ is independently hydrogen, C$_{1-4}$ alkyl, or halogen;

R$^2$ is piperidin-2-yl, 4-fluorophenyl, phenyl, pyrimidyl, pyridinyl, or pyridinyl-N-oxide, wherein said phenyl or 4-fluorophenyl is optionally substituted at the ortho position (relative to C(R$^1$)$_2$) with one R$^3$;

wherein R$^3$ is —CO$_2$H, —CH$_2$CO$_2$H, —CO$_2$Et, —CH$_2$CO$_2$Et, —CH$_2$NHCH$_2$CO$_2$H, —CH$_2$NHCH$_2$CO$_2$Et,

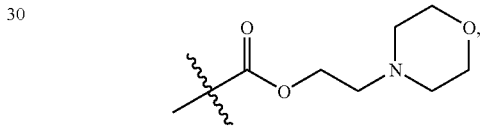

Y is selected from the group consisting of:

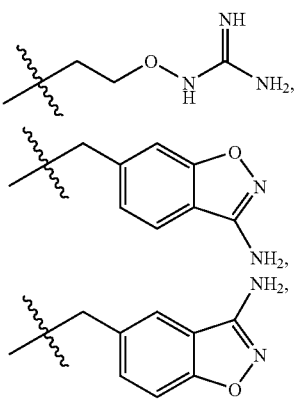

-continued

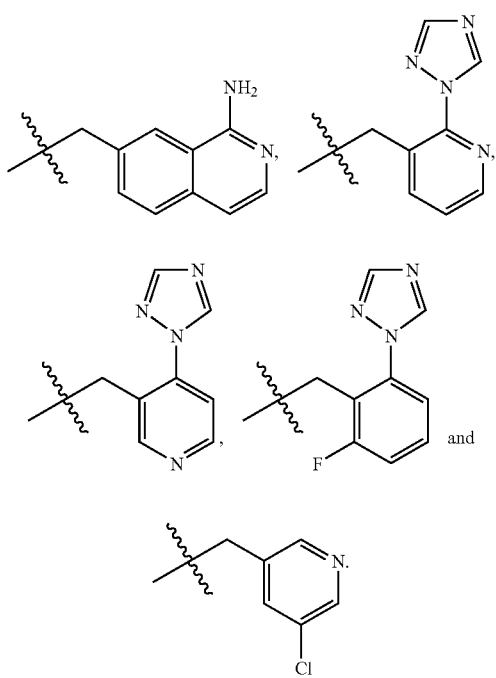

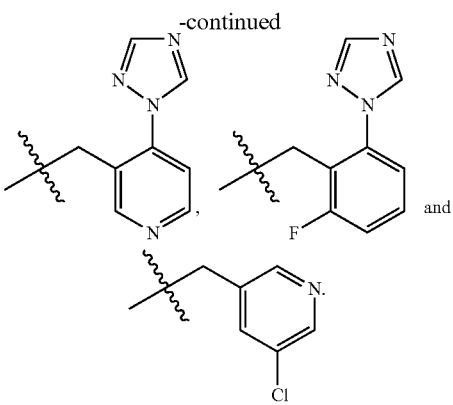

In an embodiment of the invention, one or more of the following limitations are present:

Z is Cl, or —CN;

X is absent or oxygen;

Q is H;

W is —CH$_2$CF$_2$R$^2$;

R$^2$ is phenyl, pyrimidyl, 4-fluorophenyl, or pyridyl; and

Y is selected from the group consisting of:

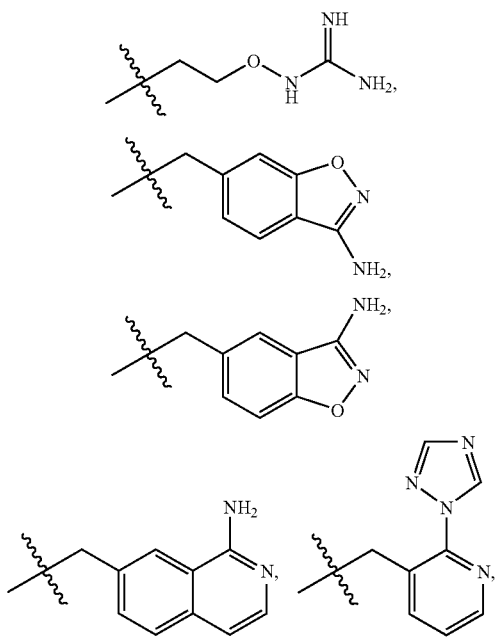

Embodiments of the present invention include prophetic compounds selected from the group consisting of:

An example of representative compounds of the present invention include those selected from the group consisting of:

| Cpd | Name |
|---|---|
| 1 | 3-cyano-6-(2,2-difluoro-2-phenyl-ethylamino)-2-{2-[(aminoiminomethyl)aminooxy]ethyl}aminocarbonylmethyl-pyridine 1-oxide, |
| 2 | 3-chloro-6-(2,2-difluoro-2-phenyl-ethylamino)-2-{2-[(aminoiminomethyl)aminooxy]ethyl}aminocarbonylmethyl-pyridine 1-oxide, |
| 3 | 3-cyano-6-(2,2-difluoro-2-pyridin-2-yl-ethylamino)-2-(3-Amino-benzo[d]isoxazol-5-ylmethyl)aminocarbonylmethyl-pyridine 1-oxide, |
| 4 | 3-cyano-6-(2,2-difluoro-2-pyridin-2-yl-ethylamino)-2-(3-amino-benzo[d]isoxazol-6-ylmethyl)aminocarbonylmethyl-pyridine 1-oxide, |
| 5 | 3-cyano-6-(2,2-difluoro-2-pyridin-2-yl-ethylamino)-2-(1-Amino-isoquinolin-7-ylmethyl)aminocarbonylmethyl-pyridine 1-oxide, |
| 6 | 3-cyano-6-(2,2-difluoro-2-pyridin-2-yl-ethylamino)-2-(4-[1,2,4]triazol-1-yl-pyridin-3-ylmethyl)aminocarbonylmethyl-pyridine 1-oxide, |
| 7 | 3-cyano-6-(2,2-difluoro-2-pyridin-2-yl-ethylamino)-2-(2-[1,2,4]triazol-1-yl-6-fluoro-phenylmethyl)aminocarbonylmethyl-pyridine 1-oxide, |
| 8 | 3-cyano-6-(2,2-difluoro-2-(4-fluoro-phenyl)-ethylamino)-2-(4-[1,2,4]triazol-1-yl-pyridin-3-ylmethyl)aminocarbonylmethyl-pyridine 1-oxide, |
| 9 | 3-cyano-6-(2,2-difluoro-2-pyrimidin-2-yl-ethylamino)-2-(4-[1,2,4]triazol-1-yl-pyridin-3-ylmethyl)aminocarbonylmethyl-pyridine 1-oxide, |
| 10 | 3-cyano-6-(2,2-difluoro-2-pyridin-2-yl-ethylamino)-2-(2-[1,2,4]triazol-1-yl-pyridin-3-ylmethyl)aminocarbonylmethyl-pyridine 1-oxide, |
| 11 | N-{2-[(aminoiminomethyl)aminooxy]ethyl}-2-[3-chloro-6-(2,2-difluoro-2-phenyl-ethylamino)-pyridin-2-yl]-acetamide, |
| 12 | 3-cyano-6-(2,2-difluoro-2-pyridin-2-yl-ethylamino)-2-(5-chloro-pyridin-3-ylmethyl)aminocarbonylmethyl-pyridine 1-oxide, and pharmaceutically acceptable salts thereof |

Embodiments of the present invention include prophetic compounds selected the group consisting of:

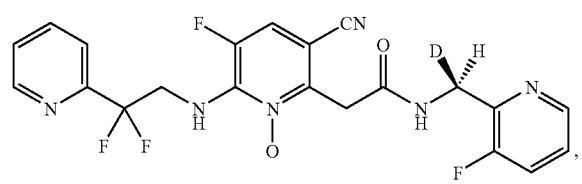

-continued

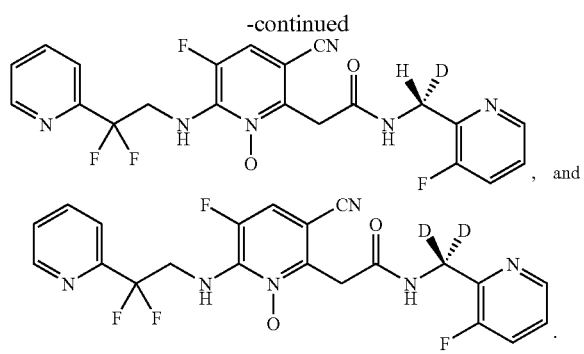

, and

The compounds of the present invention may also have polymorphic crystalline forms, with all polymorphic crystalline forms being included in the present invention.

The compounds of Formula I may also be solvated, especially hydrated. Hydration may occur during manufacturing of the compounds or compositions comprising the compounds, or the hydration may occur over time due to the hygroscopic nature of the compound.

The compounds of Formula I may in some cases also incorporate deuterium as a replacement for hydrogen. Oxidation at $sp^3$-hybridized carbon centers is sometimes a major route of metabolism in drug candidates (for example, see *Bioorg. Med Chem. Lett.* 15:2771, 2005), and the replacement of C—H with C-D at known metabolically-labile sites often indicates (via kinetic isotope effects) that cleavage of the $sp^3$ C—H bond is at least partially rate-limiting in the cytochrome P450-mediated oxidation cycle (see, for example, *J. Biol. Chem.* 280:19496, 2005, and references therein). Replacement of hydrogen with deuterium at an oxidation-prone $sp^3$-hybridized carbon center in a pharmacologically-active molecule may therefore increase the metabolic stability of the molecule in vitro and in vivo, and this may be reflected in a prolonged duration of action (e.g., increased half-life) relative to the non-deuterated congener (see *Can. J. Physiol. Pharmacol.* 77:79, 1999 for a recent review). Since primary deuterium kinetic isotope effects for C-D cleavage are sometimes ~7 or higher in non-enzymatic systems (*Chem. Soc. Rev.* 3:513, 1974), the half-life of a deuterated drug candidate may in principle be increased as much as ~7-fold provided cleavage of the C-D bond is fully rate-limiting. However, deuterium isotope effects of ~2-3-fold are a more common upper limit seen in biological systems in vitro and in vivo (*Life Sciences* 8:1123, 1969; *J. Pharm. Sci.* 62:1900, 1973; *J. Biol. Chem.* 280:19496, 2005). In contrast to the relatively large effect that deuterium (relative to hydrogen) may have on the stability of a drug candidate towards enzymatic degradation, deuterium is generally considered to have a relatively small effect on the physico-chemical properties (such as logP) of a molecule due to the close similarity in size and polarity of the two isotopes (*Chemico-Biological Interactions* 117:191, 1999).

It seems possible that replacement of an oxidation-prone methylene ($CH_2$) carbon of a drug candidate with the monodeuterated congener CHD (of appropriate stereochemistry) may provide roughly the same increase in metabolic stability as the dideuterated congener $CD_2$, since P450-mediated oxidation is sometimes highly stereoselective, with abstraction of one of the prochiral methylene hydrogens greatly favored over the other. However, the metabolic stability of the monodeuterated congener CHD (of appropriate stereochemistry) may be somewhat less than for the dideuterated congener $CD_2$ if, for example, the single cytochrome P450 responsible for oxidation at that site is not highly stereoselective, or if multiple members of the P450 superfamily oxidize the molecule at that carbon in vivo (*J. Biol. Chem.* 280:19496, 2005).

Dideuteration of a drug candidate with a "typical" molecular weight of ~500 dosed at ~1 g/day would maximally release ~0.004 mol of deuterium/day into a hypothetical 70 kg patient that is comprised of ~7 kg (~7000 mol) hydrogen (Emsley, John; *The Elements*, $3^{rd}$ ed., Clarendon Press, Oxford, 1998). This corresponds to 1 part deuterium in ~1.8 million parts hydrogen (0.6 ppm D/day), which appears negligible compared to the natural abundance deuterium found at 1 part in ~6400 (~0.016% D or ~160 ppm D) relative to hydrogen (*J. Pharmaceutical Sci.* 64:367, 1975). Furthermore, cytochrome P450-mediated cleavage of a C-D bond uses water as the ultimate acceptor of the liberated deuterium atom (*J. Biol. Chem.* 280:19496, 2005). While systemic deuterated water concentrations of ≧25% are toxic to many animals, continuous exposure to systemic ~15% deuterated water appears to be tolerated for months in multiple mammalian species, including dogs. Humans of all ages have routinely and without adverse effect ingested single doses of 0.1 mL $D_2O$/kg body weight (0.7 mol deuterium for a 70 kg human), which doubles the natural abundance of systemic deuterium from ~0.015% (~150 ppm D) to ~0.030% (~300 ppm D) before returning to baseline with a half-life of a few days (see *J. Pharmaceutical Sci.* 64:367, 1975 and *Can. J. Physiol. Pharmacol.* 77:79, 1999 for reviews on the effects of $D_2O$ administration to animals and humans). One human was maintained at ~0.5% systemic deuterium (5000 ppm D) for over four months without apparent adverse effect via an initial 400 mL 50% $D_2O$ oral dose, followed by daily 40 mL 50% $D_2O$ ingestion (*J. Clin. Invest.* 46:313, 1967). As expected, after four months of $D_2O$ ingestion the 0.5% systemic deuterium was extensively distributed into the "non-exchangeable" C—H carbon pool, presumably via metabolic pathways using deuterated carbon precursors from the "exchangeable" (carbon acid) C—H carbon pool. For example, 23 of the 46 hydrogens in cholesterol had 0.45% D incorporation, as predicted (*J. Biol. Chem.* 121:235, 1937). Therefore, while a dideuterated drug candidate of molecular weight ~500 chronically dosed at ~1 g/day would seem highly unlikely to release enough deuterium in vivo to pose a health risk to the patient over the long term, a monodeuterated congener would by definition maximally release only one-half that amount of deuterium into the patient (i.e., ~0.002 mol, or 0.3 ppm deuterium/day rather than 0.6 ppm deuterium/day).

A suitably deuterated thrombin inhibitor with a prolonged duration of action may allow for a less frequent dosing schedule than would otherwise be possible with the non-deuterated congener, thus potentially improving patient dosing compliance. The increased half-life possibly seen with a deuterated thrombin inhibitor may also cause a reduction in the peak-to-trough ratio of plasma drug levels for a given dosing schedule relative to the non-deuterated congener, and this effect could improve the safety margin of the thrombin inhibitor. In another aspect, the present invention includes compositions which are useful for in vivo imaging of thrombi in a mammal, comprising the compounds of the present invention which is capable of being detected outside the body. Preferred are compositions comprising a compound of the present invention and a detectable label, such as a radioactive or paramagnetic atom.

In another aspect, the present invention provides diagnostic compositions which are used for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

According to a preferred aspect, useful compounds are those wherein the pyridine substituent, which is adjacent to the difluoromethylene, is substituted with a detectable label, such as a radioactive iodine atom, such as I-125, I-131 or I-123. The detectable label can also be a radioactive or paramagnetic chelate in which a suitable ligand (L) is attached to said pyridine substituent, either directly or via a divalent linking group (A"). By suitable ligand is meant an organic moiety that is capable of chelating a radioactive or paramagnetic metal ion.

In these compounds, the divalent linking group A" includes groups that are capable of covalently bonding with both the pyridyl and the chelating means. For example, A" may be —C(=S)—, —C(=O)—, —C(=NH)—$(CH_2)_6$—C(=NH)—, —C(=O)—$(CH_2)_6$—C(=O)—, and the like.

Also, in the compounds represented by Formula I, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene group or by up to four separated ethylene units separated by a nitrogen or oxygen or sulfur atom. Preferred as a completing means is diethylenetrimine-N,N,N',N",N"'-pentaacetic acid (DTPA). DTPA is well known in the art as a chelating means for the radioactive atoms indium-111 (In-111), technetium-99m (Tc-99m), and the paramagnetic atom gadolinium (Gd). Khaw, et al., Science 209:295 (1980); Paik C. H. et al., U.S. Pat. No. 4,652,440 (1987); Gries, H. et al., U.S. Pat. No. 4,957,939 (1990). A preferred chelating ligand, L, is 1-(para-aminobenzyl)-diethylenetriaminepentaacetic acid. Also included as chelating means are compounds which contain sulfhydryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The compounds of Formula I can be labeled with radioactive iodine by using an exchange reaction. Exchange of hot iodine for cold iodine is well known in the art. Alternatively, a radio iodine labeled compounds can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of the compounds of Formula I complexed with a radioactive atom; suitable radioactive atoms include Co-57, Cu-67, Ga-67, Ga-68, Ru-97, Tc-99m, In-111, In-113m, Hg-197, Au-198, and Pb-203. Some radioactive atoms have superior properties for use in radiochemical imaging techniques. In particular, technetium-99m (Tc-99m) is an ideal radioactive atom for imaging because of its nuclear properties. Rhenium-186 and -188 also have gamma emission which allows it to be imaged. Preferred compositions contain the radioactive atom, Tc-99m.

The compounds of Formula I can be labeled by any of the many techniques known in the art to provide a composition of the present invention. For example, the compounds can be labeled through a chelating agent such as diethylenetriaminepentaacetic acid (DTPA) or metallothionein, both of which can be covalently attached to the compounds of Formula I.

In general, the compositions of the present invention containing technetium-99m are prepared by forming an aqueous mixture of technetium-99m and a reducing agent and a water-soluble ligand, and then contacting the mixture with a compound of the present invention represented by Formula I. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula I having a DTPA chelating means with technetium-99m. This may be accomplished by combining a predetermined amount (as 5 µg to 0.5 mg) of a compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2-0.22 micron), then is dispensed into 0.9% saline for injection, if desired.

Another embodiment of the compositions of the present invention is prepared by labeling a compound of Formula I having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of Formula I having a metallothionein attached thereto. After incubating the mixture for a period of time and under conditions which allow for an exchange of the technetium-99m from the glucoheptonate complex to the metallothionein of a compound of Formula I, the technetium-labeled composition of the present invention is formed.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartrate, and sodium dithionite. The preferred agents are stannous reducing agents, especially stannous chloride or stannous glucoheptonate. The amount of reducing agent is that amount necessary to reduce the technetium-99m to provide for the binding to the chelating means of a compound of Formula I in this radioisotope's reduced state. For example, stannous chloride ($SnCl_2$) is the reducing agent and can be used in range from 1-1,000 µg/mL.

Citric acid complexes with technetium-99m quickly to form a stable technetium-99m-citrate complex. Upon contact with a compound of Formula I, substantially quantitative transfer of technetium-99m from its citrate complex to the chelating means of a compound of Formula I is achieved rapidly and under mild conditions. The amount of citric acid (as sodium citrate) can range from about 0.5 mg/ml up to the amount maximally soluble in the medium. Preferred amounts of citric acid range from 15 to 30 µg/ml.

The amount of compound of Formula I having a chelating means can range from 0.001 to about 3 mg/mL, preferably about 0.017 to about 0.15 mg/mL. Finally, technetium-99m in the form of pertechnetate can be used in amounts of preferably about 1-50 mCi. The amount of mCi per mg of compound of the present invention is preferably about 30-150.

The reaction between a compound of Formula I and the metal ion-transfer ligand complex is preferably carried out in a aqueous solution at a pH at which a compound of Formula I is stable. By "stable", it is meant that the compound remains soluble and retains its inhibitory activity against $\alpha$-thrombin. Normally, the pH for the reaction will be from about 5 to 9, the preferred pH being above 6-8. The technetium-99m-citrate complex and a compound of Formula I are incubated, preferably at a temperature from about 20° C. to about 60° C., most preferably from about 20° C. to about 37° C., for a sufficient amount of time to allow transfer of the metal ion from the citrate complex to the chelating means of the compound of Formula I. Generally, less than one hour is sufficient to complete the transfer reaction under these conditions.

Alternative compositions of the present invention include an In-111 labeled compound of the present invention.

The present invention also includes compositions of the compounds of the present invention which are useful for in vivo imaging of thrombi in a mammal, comprised of the compounds represented by Formula I complexed to a paramagnetic atom.

Preferred paramagnetic atoms are divalent or trivalent ions of elements with an atomic number of 21 to 29, 42, 44 and 58 to 70. Suitable ions include chromium (III), manganese (II), iron (III), iron (II), cobalt (II), nickel (II), copper(II), praseodymium (III), neodymium (III), samarium (III) and ytterbium (III). Because of their very strong magnetic moments, gadolinium (III), terbium (III), dysoprosium (III), holmium (III), and erbium (III) are preferred. Especially preferred for the paramagnetic atom is gadolinium (III).

The compositions of the present invention may be prepared by combining a compound of Formula I with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of a compound of Formula I in a similar aqueous medium and stirred. The reaction mixture may be heated moderately until the reaction is completed. Insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The present invention also includes diagnostic compositions which are useful for in vivo imaging of thrombi in a mammal, comprising a pharmaceutically acceptable carrier and a diagnostically effective amount of a composition derived from a compound of Formula I.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts.

Also, the diagnostically effective amount and method of administration can be tailored to achieve optimal efficacy but will depend on such factors as weight, diet, concurrent medication and other factors which those skilled in the medical arts will recognize. The dose for imaging should be sufficient for detecting the presence of the imaging agent at the site of a thrombus in question. Typically, radiologic imaging will require that the dose provided by the pharmaceutical composition position of the present invention be about 5 to 20 µCi, preferably about 10 µCi. Magnetic resonance imaging will require that the dose provided be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

"Pharmaceutically acceptable carriers" for in vivo use are well known in the pharmaceutical art, and are described, for example, in *Remington's Pharmaceutical Sciences*, Mack Publishing Co. (A. R. Gennaro edit. 1985). The pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The present invention also encompasses diagnostic compositions prepared for storage or administration. These would additionally contain preservatives, stabilizers and dyes. For example, sodium benzoate, sorbic acid and esters of para-hydroxybenzoic acid may be added as preservatives. Idem at 1449. In addition, antioxidants and suspending agents may be used.

The in vivo imaging methods of the present invention also offer several advantages over previous imaging techniques for the detection or monitoring of the presence, size, regression or increase of a thrombus. In particular, the present invention provides compounds, compositions and diagnostic compositions that bind tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

The term "in vivo imaging" as used herein relates to methods of the detection of a thrombus in a mammal, as well as the monitoring of the size, location and number of thrombi in a mammal, as well as dissolution or growth of the thrombus.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the antecubital vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula I having a chelating means attached thereto may be injected into the mammal, followed at a later time by the radioactive atom thereby forming in vivo at the site of the thrombus the composition comprising a compound of Formula I complexed to a radioactive atom. Alternatively, a composition comprising a compound of Formula I complexed to a radioactive atom may be injected into the mammal.

The "diagnostically effective amount" of the compounds, compositions or diagnostic compositions used in the methods of the present invention will, as previously mentioned, depend on the route of administration, the type of mammal being treated, and the physical characteristics of the specific mammal under treatment. These factors and their relationship to determining this dose are well known to skilled practitioners in the medical diagnostic arts. The dose for in vivo imaging should be sufficient for detecting the presence of the imaging agent at the site of a thrombus in question. Typically, radiologic imaging will require that the dose provided by the diagnostic composition of the present invention be about 5 to 20 μCi, preferably about 10 μCi. Magnetic resonance imaging will require that the dose provided by the diagnostic composition be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to its ground state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention are detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

| Abbreviation | Meaning |
| --- | --- |
| DMSO | dimethylsulfoxide |
| tBu, or t-Bu as in KOtBu or tBuOH | tert-butyl |
| TFA | trifluoroacetic acid |
| DCM | dichloromethane |
| DIEA or DIPEA | diisopropylethyl amine |
| DIC | diisopropylcarbodiimide |
| OAc, as in Pd(OAc)$_2$ | acetate |
| BOP | O-benzotriazol-1-yloxytris(dimethylamino)-phosphonium hexafluorophosphate |
| MCPBA or mCPBA | meta-chloroperoxybenzoic acid |
| Me, as in MeOH | methyl |
| Et, as in CO$_2$Et | ethyl |
| DMF | dimethylformamide |
| Tf$_2$O | triflic anhydride |
| NBS | N-bromo succinimide |
| AIBN | azobis(isobutylnitrile) |
| Gly | glycine |
| Boc | tert-butoxycarbonyl |
| DCC | dicyclohexylcarbodiimide |
| KHMDS | potassium hexamethyl disilazane |
| LAH | lithium aluminum hydride |
| DIBAL | diisobutyl aluminum hydride |
| D, as in DCl or D$_2$O | deuterium |
| TEA | triethylamine |
| THF | tetrahydrofuran |
| PPh$_3$ | triphenylphosphine |
| Hex | hexanes |
| LC/MS (ESI) | liquid chromatograph/mass spectrum (electrospray ionization) |
| LCMS/ELSD | liquid chromatograph mass spectrum/evaporative light scattering detector |
| DMAP | dimethylaminopyridine |
| NMR | nuclear magnetic resonance |
| TLC | thin layer chromatography |
| BINAP | 2,2'-bis(diphenylphosphino)-1,1'-binaphthyl |
| dba, as in Pd$_2$(dba)$_3$ | dibenzylideneacetone |
| EDTA | ethyldiaminetetraacetic acid |
| NMP | N-methyl pyrrolidone |

Chemical Definitions

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The term "alkyl" as employed herein by itself or as part of another group refers to both straight and branched chain radicals of up to 12 carbons, unless the chain length is limited thereto, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl. Preferably, alkyl is 1 to 6 carbon atoms.

The term "alkynyl" is used herein to mean a straight or branched chain radical of 2-20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkynyl moiety as a substituent group, the unsaturated linkage, i.e., the vinylene or acetylene linkage, is preferably not directly attached to a nitrogen, oxygen or sulfur moiety.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

The term "triflate" refers to the anion trifluoromethane sulfonate, $CF_3SO_3^-$, abbreviated $OTf^-$. The adjectival form of "triflate" is "triflic". For example, triflic anhydride refers to trifluoromethane sulfonate anhydride, $(CF_3SO_2)_2O$, abbreviated $Tf_2O$.

Pharmaceutically Acceptable Salts

The pharmaceutically acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, trifluoroacetate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth, including salts with a guanidinyl moiety. Also, the basic nitrogen-containing groups may be quaternized with such agents as lower alkyl halides, such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Preferred acids for forming acid addition salts include HCl, HBr, and acetic acid.

Applications

For their end-use application, the present invention may be employed for a number of therapeutic purposes. The present invention inhibits thrombin. Therefore, these compounds are useful for the treatment or prophylaxis of states characterized by abnormal venous or arterial thrombosis involving either thrombin production or action.

These states include, but are not limited to, deep vein thrombosis; pulmonary embolism; arterial thrombosis; systemic embolism usually from the atrium during arterial fibrillation or from the left ventricle after transmural myocardial infarction; unstable angina; restenosis; adult respiratory distress syndrome; endotoxic shock; hypercoagulability during chemotherapy; disseminated intravascular coagulopathy which occurs during septic shock, viral infections and cancer; myocardial infarction; stroke; coronary artery bypass; fibrin formation in the eye; orthopedic surgery such as hip replacement; and thrombus formation resulting from either thrombolytic therapy or percutaneous transluminal coronary angioplasty (PCTA). A preferred use of the invention is for the prophylaxis or treatment of deep vein thrombosis.

Compounds of the present invention are expected to have utility in the treatment and prophylaxis of disseminated intravascular coagulation caused by any mechanism including bacteria, multiple trauma, and intoxication.

Compounds of the present invention are expected to be useful in situations where there are elevated thrombin levels without signs of hypercoagulability, such as in Alzheimer's disease and pancreatitis.

Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention may also be used as an anticoagulant in extracorporeal blood circuits.

Stents have been shown to reduce restenosis, but are thrombogenic. A strategy for reducing the thrombogenicity of stents is to coat, embed, adsorb or covalently attach a thrombin-inhibiting agent to the stent surface. The compounds of the present invention can be employed for this purpose. Compounds of the invention can be attached to, or embedded within soluble and/or biodegradable polymers as and thereafter coated onto stent materials. Such polymers can include polyvinylpyrrolidone, polyhydroxy-propylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent No. 2,164,684 and PCT Published Applications Nos. WO 96/11668, WO 96/32143 and WO 96/38136.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement.

The compounds of the present invention may be useful in treating neurodegenerative diseases, such as Alzheimer's disease and Parkinson's disease.

The compounds of the present invention may be administered in an effective amount within the dosage range of about 0.1 to about 500 mg/kg, preferably between 0.1 to 10 mg/kg body weight, on a regimen in single or 2-4 divided daily doses.

The compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The compounds of the present invention may also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

For compositions of the present invention suitable for administration to a human, the term "excipient" is meant to include, but not be limited by, those excipients described in the *Handbook of Pharmaceutical Excipients*, American Pharmaceutical Association, $2^{nd}$ Ed. (1994), which is herein incorporated by reference in its entirety. Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxy-propylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

General Synthetic Methods

Typical preparations of exemplified compounds in the present invention are shown in Schemes I-VIId.

Scheme I describes a typical protocol for accessing targets for which Z is CN and Q is F. In this case, nucleophile addition (i.e., t-butoxide) occurs predominantly ortho to Q (i.e., ortho to fluorine). Commercially available I-1 (Aldrich) undergoes chloride displacement in the presence of spray-dried KF in hot DMSO to afford trifluoropyridine I-2, which in turn is activated toward regioselective nucleophilic aromatic displacement of fluoride by KOtBu to provide I-3. Nucleophilic aromatic substitution by malonate derivatives such as the sodium salt of t-butyl methyl malonate in hot dioxane is then directed ortho to the Z substituent (i.e., cyano) to provide I-4. I-4 then undergoes deprotection of both t-butyl groups as well as decarboxylation of the unmasked carboxylic acid in the presence of TFA to provide I-5. Conversion to the 2-chloropyridine I-6 under standard POCl₃ conditions, followed by acidic deprotection of the methyl ester in warm aqueous HCl/dioxane provides I-7. The free acid is then converted to the activated ester I-8 (e.g., nitrophenyl ester) using a phenol derivative (e.g., 4-nitrophenol) with DIC as the coupling reagent. Pyridine N-oxide formation is then accomplished using sodium percarbonate in the presence of triflic anhydride in acetonitrile to afford I-9. Attack of the activated ester by ~1-1.2 eq amine Y—NH₂ occurs at room temperature in DCM/CH₃CN to yield I-10, and final targets I-11 are obtained by reaction of 2-chloropyridine N-oxide I-10 with amine W—NH₂ in hot DMSO in the presence of DIEA.

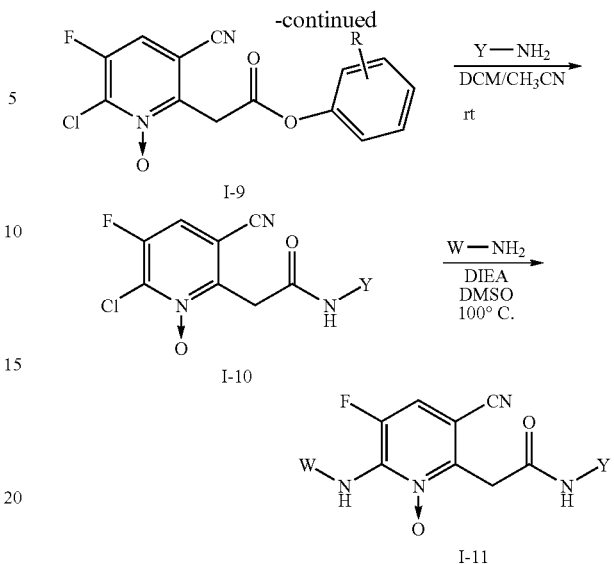

Scheme II describes a typical protocol for accessing targets for which Z is CN and Q is H. In this case, nucleophile addition (i.e., malonate carbanion derivative) occurs both ortho to Z (i.e., ortho to cyano) and ortho to Q (i.e., ortho to hydrogen). Known II-1 (*Angew. Chem.* 92:390-1, 1980) is treated with the sodium salt of dimethyl malonate carbanion in warm dioxane to afford a mixture of regioisomers II-2 (only the desired regioisomer is drawn in Scheme II). This mixture of malonate adducts II-2 is carried forward in warm aqueous HCl/dioxane to hydrolyze the methyl esters and to decarboxylate one of the unmasked carboxylic acids to provide the mixture of regioisomers II-3. This mixture of free acids is then converted to the regioisomeric activated esters II-4 using a phenol derivative (e.g., 4-nitrophenol) and a coupling reagent such as DIC. At this stage, silica gel chromatography allows for the isolation of the single desired regioisomer II-4 (desired regioisomer is drawn in Scheme II). Conversion of II-4 to final targets II-7 in three steps is exactly analogous to that described in Scheme I for the conversion of I-8 to I-11.

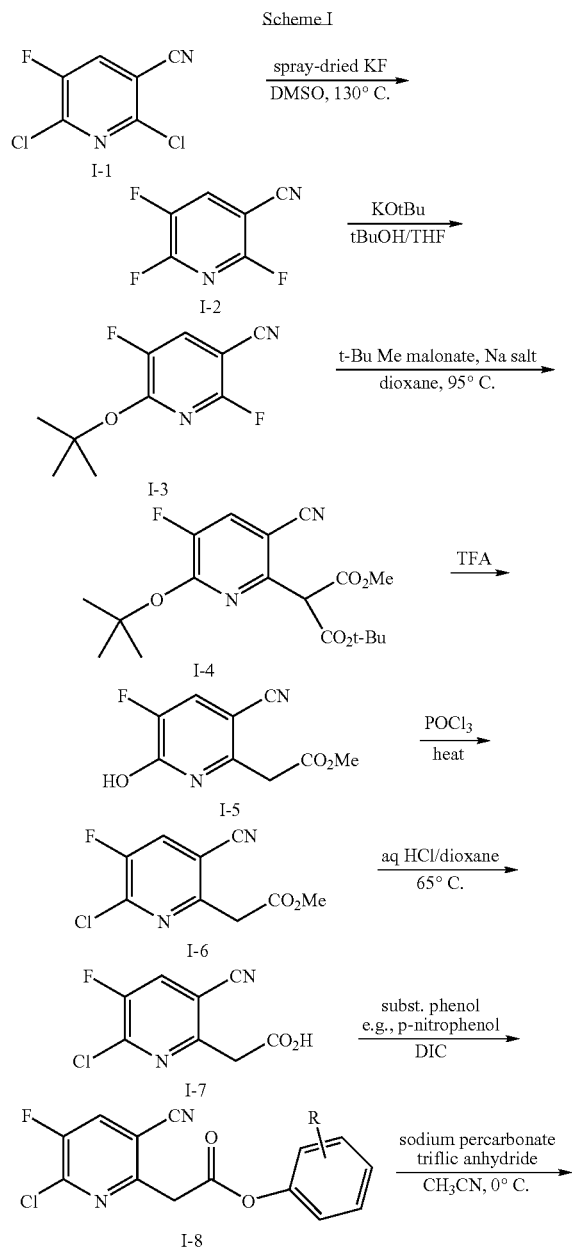

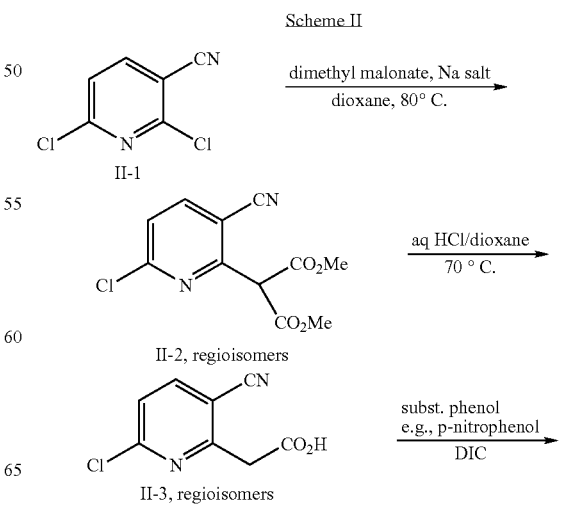

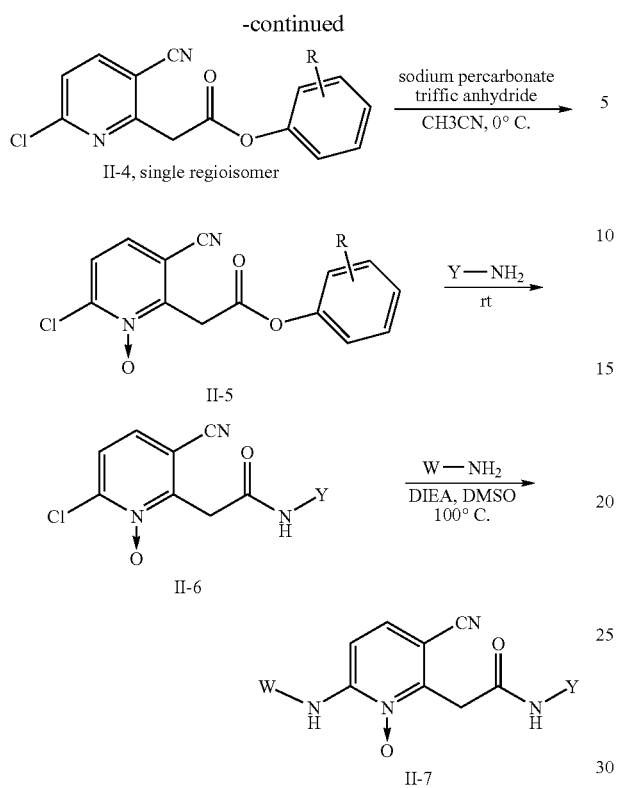

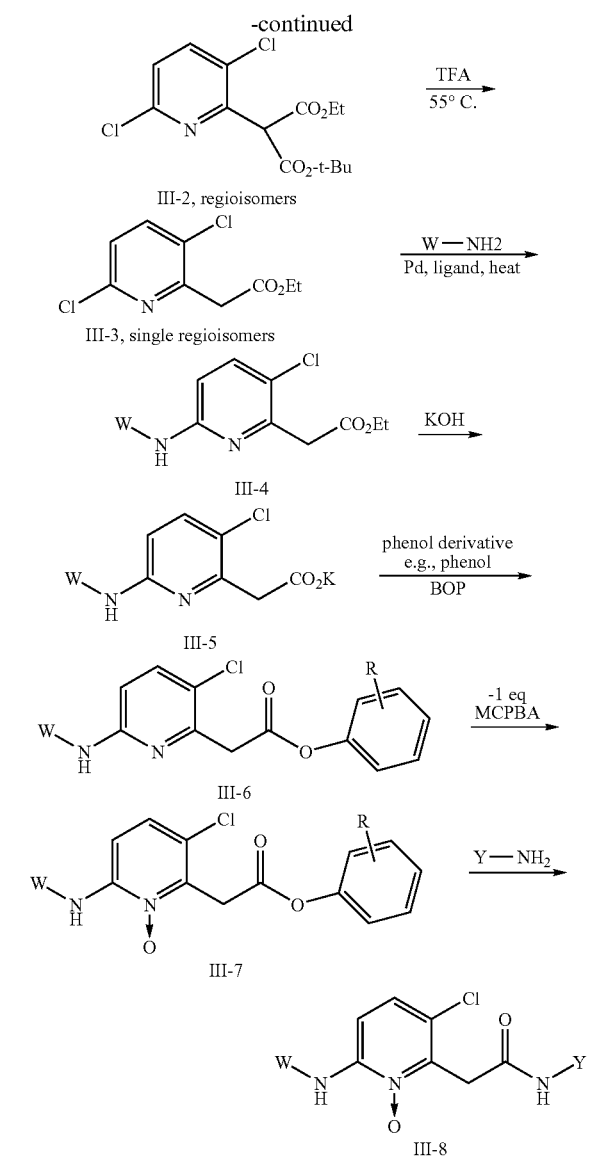

Scheme III illustrates one method for accessing certain targets for which Z is Cl and Q is H. Known III-1 (*J. Chem Soc. C: Org.* 1375, 1970) is treated with the sodium salt of the t-butyl ethyl malonate carbanion in hot DMSO to afford a mixture of regioisomers III-2 (only the desired regioisomer is drawn in Scheme III), and this mixture is decarboxylated in warm TFA to provide III-3. At this stage, silica gel chromatography allows for the isolation of the single desired regioisomer III-3, as drawn in Scheme III. Amine W—$NH_2$ is then used to regioselectively displace the 2-chloro moiety of III-3 via a Buchwald amination protocol using a palladium(0)-ligand complex, such as that generated in situ from Pd(OAc)$_2$ and 2-(dicyclohexylphosphino)biphenyl, in hot toluene in the presence of a suitable base, such as $K_3PO_4$ (*J. Org. Chem.* 65:1158, 2000), to provide aminopyridine III-4. Saponification of the ester under standard basic aqueous conditions, followed by BOP-mediated activated ester formation from a phenol and the azeotropically-dried carboxylate salt III-5 afforded the aryl ester III-6. Aminopyridine III-6 was converted to the pyridine N-oxide III-7 via treatment with MCPBA, and final target III-8 was accessed by attack of the aryl ester III-7 by Y—$NH_2$ in warm MeOH.

Schemes IV and V outline general methods for accessing targets for which Z is H, F, Cl, Br, $C_{(1-4)}$alkyl, —CC—H, —CC—$CH_3$, and —CC-Et, and for all claimed Q, for which X is oxygen. Scheme IV is preferred for targets for which nucleophile addition (i.e., malonate carbanion derivative) occurs ortho to the Z substituent. Known IV-1 (see Scheme VII) is heated with KF in the presence of a polar aprotic solvent such as DMSO or sulfolane (Eur. Pat. Appl. 759429, 1997; *Helv. Chim. Acta* 59:229-35, 1976) to afford the difluoropyridine IV-2.

The malonate adduct IV-3 is then obtained by reaction of difluoropyridine IV-2 with two equivalents of a malonate carbanion derivative such as the sodium salt of t-butyl methyl malonate, either at rt or elevated temperature, in a solvent such as dioxane or DMSO. TFA can then be used to deprotect the t-butyl ester, with decarboxylation of the resulting carboxylic acid to provide IV-4.

Treatment of methyl ester IV-4 with warm aqueous HCl, in the presence or absence of a cosolvent such as dioxane, affords the free acid IV-5. It may sometimes prove expedient to deprotect and decarboxylate the t-butyl ester and saponify Scheme III

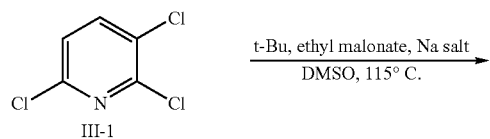

the methyl ester without the use of TFA, but rather with warm aqueous HCl alone in one step, to provide IV-5 directly from IV-3. The free acid IV-5 is then coupled to a phenol, such as p-nitrophenol, in the presence of a coupling reagent such as DIC, to afford activated ester IV-6.

The pyridine IV-6 is then converted to the pyridine N-oxide IV-7 by the use of a peroxyacid where, e.g., R is trifluoroacetyl, 3-chlorobenzoyl, or trifluoromethylsulfonyl.

Trifluoroperacetic acid can be generated in situ from 30% aq $H_2O_2$ and either trifluoroacetic acid or trifluoroacetic anhydride. 3-chloroperbenzoic acid is commercially available (Aldrich). Trifluoromethylpersulfonic acid is thought to be generated in situ from the addition of triflic anhydride to a suspension of sodium percarbonate (Aldrich) in cold acetonitrile. The N-oxidation step can occur in a solvent chosen from $CH_3CN$, DCM, and/or $CHCl_3$, and/or mixtures thereof, and at temperatures preferably ranging from 0° C. to 70° C. Conversion of IV-7 to final targets IV-9 in two steps occurs exactly analogously to that described for the conversion of I-9 to I-11 in Scheme I.

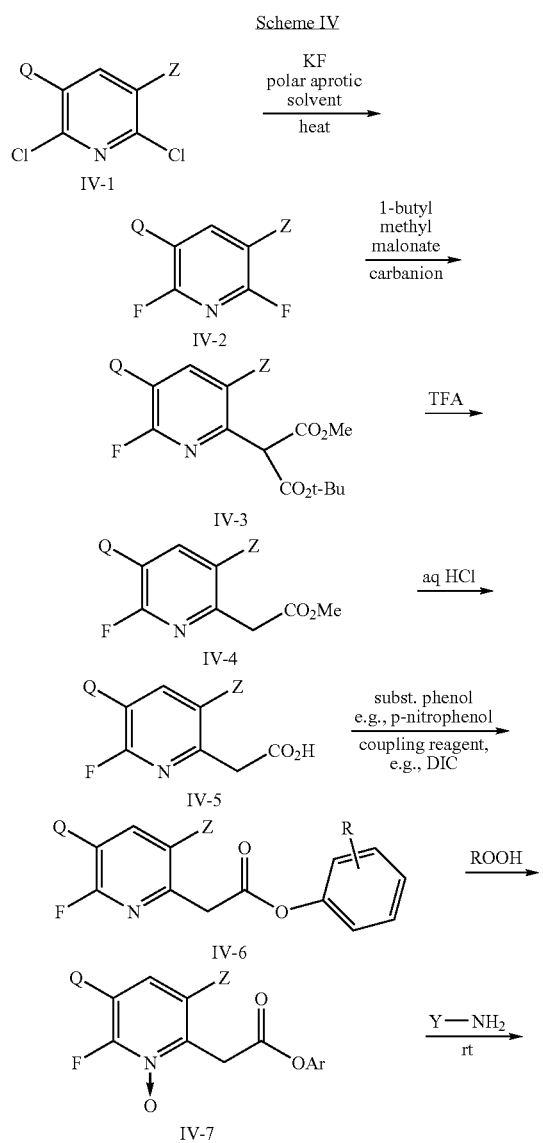

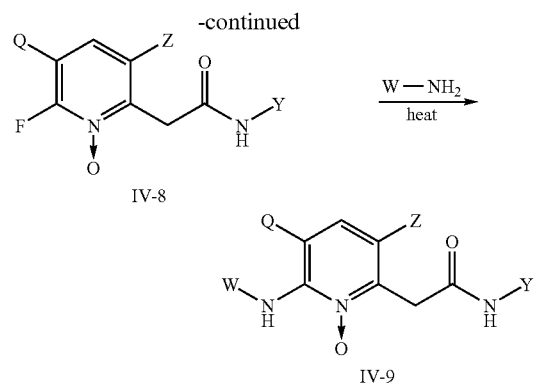

Scheme V is preferred for targets for which nucleophile addition (i.e., t-butoxide oxyanion) occurs ortho to the Q substituent. Known V-1 (see Scheme VII) is heated with KF in the presence of a polar aprotic solvent such as DMSO or sulfolane (Eur. Pat. Appl. 759429, 1997; *Helv. Chim. Acta* 59:229-35, 1976) to afford the difluoropyridine V-2. Intermediate V-2 is activated toward regioselective nucleophilic aromatic displacement of fluoride by t-butoxide oxyanion, e.g., KOtBu, to provide V-3. Nucleophilic aromatic substitution by a malonate anion derivative, e.g., sodium or potassium t-butyl methyl malonate, in a solvent such as hot DMSO, is then directed ortho to the Z substituent of V-3. Treatment of the resulting malonate derivative adduct with TFA engenders loss of both t-butyl groups and subsequent decarboxylation of the unmasked carboxylic acid to complete the conversion of intermediate V-3 to methyl ester V-4 in two steps. Conversion to the 2-chloropyridine V-5 occurs under standard chlorination conditions, e.g., hot $POCl_3$, $PCl_5$, or $SOCl_2$ or oxalyl chloride in the presence or absence of DMF. Chloropyridine V-5 is then heated with KF in the presence of a polar aprotic solvent such as DMSO or sulfolane (Eur. Pat. Appl. 759429, 1997; *Helv. Chim. Acta* 59:229-35, 1976) to afford the fluoropyridine V-6. Acidic deprotection of the methyl ester in warm aqueous HCl/dioxane provides V-7 without undue loss of the fluoropyridine moiety (*Bioorg. Med. Chem.* 6:1631-1640, 1998). The free acid V-7 is then converted to final the activated ester V-8 (e.g., nitrophenyl ester) using a phenol derivative (e.g., 4-nitrophenol) with DIC as the coupling reagent. Pyridine N-oxide formation is then accomplished using sodium percarbonate in the presence of triflic anhydride in acetonitrile to afford V-9. Conversion of V-9 to final targets V-11 in two steps occurs exactly analogously to that described for the conversion of I-9 to I-11 in Scheme I.

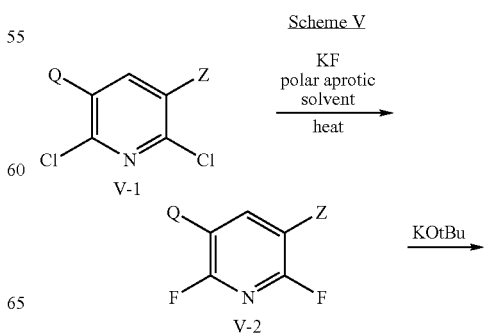

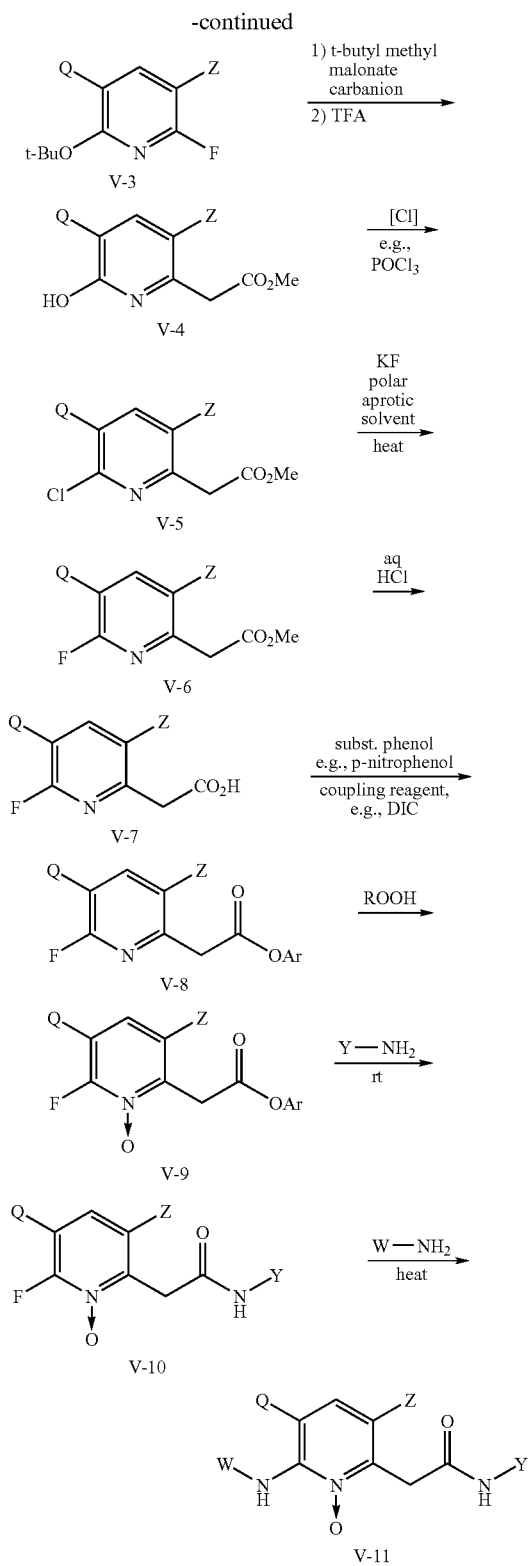

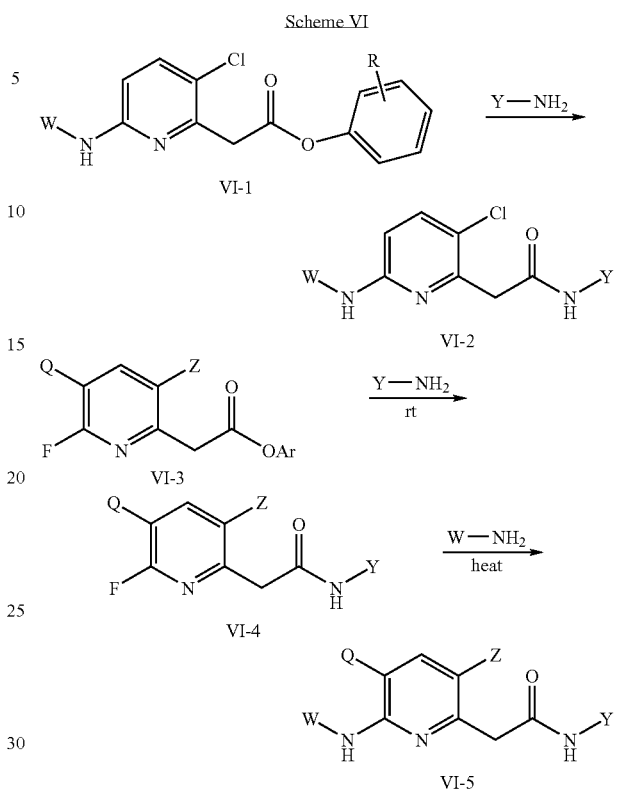

Scheme VI outlines methods for accessing targets for which X is absent. The methods are exactly analogous to the conversion of III-6 to III-8 and V-8 to V-11 in Schemes III and V, respectively, except the oxidation step in both cases has been omitted.

Scheme VII shows synthetic routes for all starting material 2,6-dichloropyridines IV-1 and V-1. VII-1 (Aldrich), VII-2 (*Journal of Heterocyclic Chemistry* 21:673-9, 1984; *Heterocycles* 36:431-434, 1993), VII-3 (*J. Chem. Soc. C: Organic* 1375, 1970), VII-4 (*Angewandte Chemie* 92:390-391, 1980), and VII-5 (Aldrich) are all known compounds. In addition, the difluoropyridine VII-6 (analogous to IV-2 and V-2) is known (*J. Fluorine Chem.* 18:497-506, 1981).

Commercially available iodopyridine VII-7 (Matrix Scientific) can undergo palladium-mediated cross-coupling with tetramethyltin (*J. Labelled. Compd. Radiopharm.* 45:423-434, 2002), ethyne (*Tetrahedron Lett.* 39:5159-5162, 1998), propyne (*Tetrahedron Lett.* 40:2481-2484, 1999), or 1-butyne (*J. Med. Chem.* 39:892-903, 1996) in the presence of the appropriate ligand(s) to afford the methylpyridine VII-8, the ethynylpyridine VII-9, the prop-1-ynylpyridine VII-10, or the but-1-ynlypyridine VII-11, respectively. The alkynylpyridines VII-9-VII-11 can be reduced to the corresponding alkylpyridines VII-12-VII-14 in the presence of $H_2$ and $PtO_2$, Pt/C, or Pd/C while retaining the chloro substituents (*J. Med. Chem.* 45:3639-3648, 2002; *J. Org. Chem.* 55:541-548, 1990; *J. Med. Chem.* 45:2841-2849, 2002; *J. Heterocycl. Chem.* 34:145-152, 1997; *J. Heterocycl. Chem.* 38:1297-1306, 2001). Alternatively, prior to alkyne reduction, the 3-alkynyl-2,6-dichloropyridines VII-9-VII-11 can be converted to the corresponding 3-alkynyl-2,6-fluoropyridines with the use of KF in a hot polar aprotic solvent, as described in Schemes IV and V (e.g., the conversion of IV-1 to IV-2), and the resulting 3-alkynyl-2,6-fluoropyridines can be reduced ($H_2$ and Pd or Pt; *Bioorg. Med. Chem.* 10:1115-1122, 2002) to the corresponding 3-alkyl-2,6-fluoropyridines (e.g., IV-2 where Q is H and Z is ethyl, propyl, or butyl) with potentially less hydrogenolysis than might be observed with the corresponding 2,6-chloropyridines.

Known fluoroaminopyridine VII-15 (*Helv. Chim. Acta* 77:1057-1064, 1994) can be treated with KI and NaNO$_2$ under standard Sandmeyer conditions to afford fluoroiodopyridine VII-16 (*J. Org. Chem.* 22:7752-7754, 2004), that can then under go methylation or alkynylation and reduction exactly as described above to afford the alkyl- and alkynylpyridines VII-17-VII-23. Finally, fluoroaminopyridine VII-15 can be chlorinated (*J. Med. Chem.* 45:4755-4761, 2002) or brominated (*J. Org. Chem.* 60:1408-1412, 1995) under standard Sandmeyer conditions to afford VII-24 or VII-25, respectively.

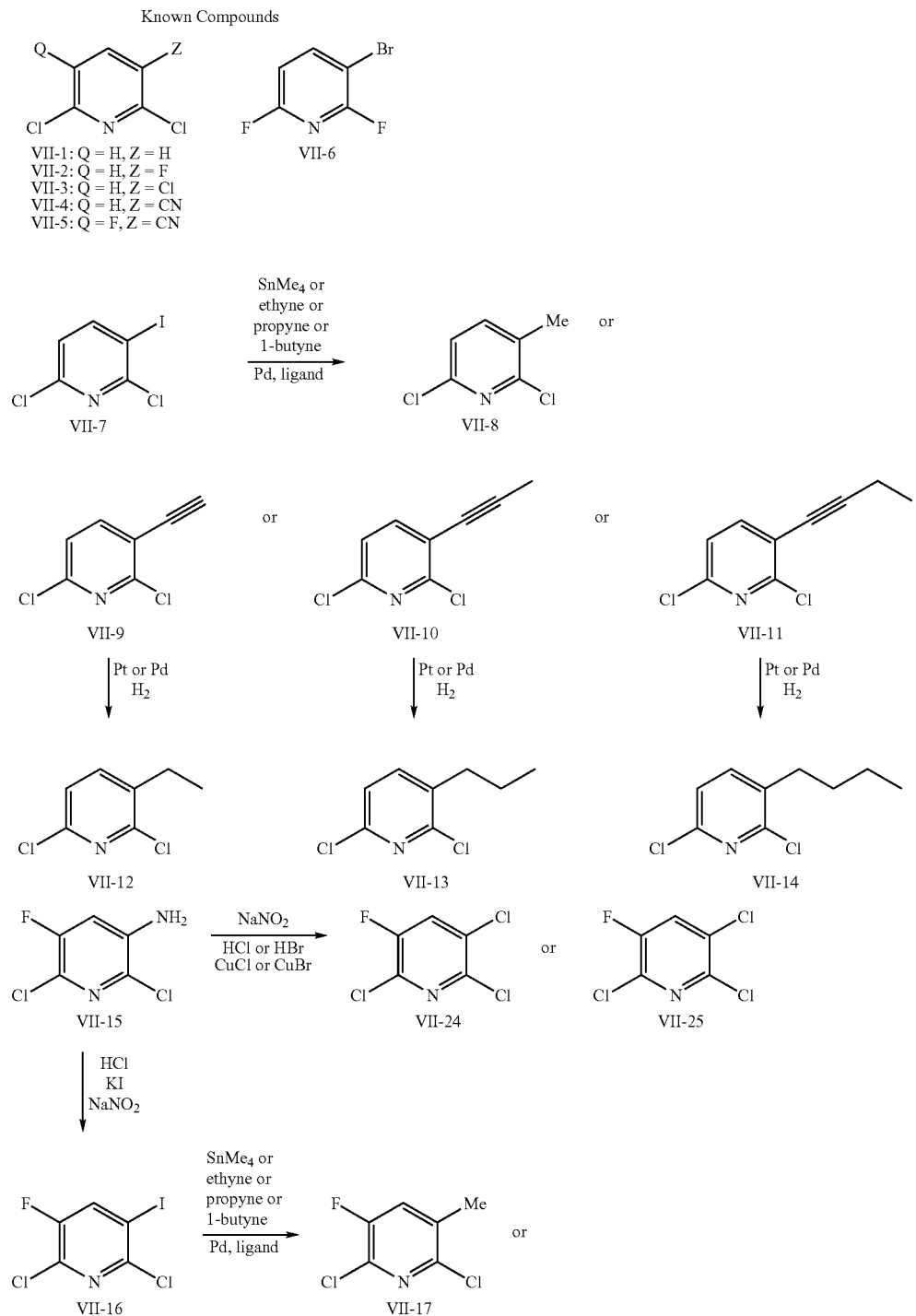

-continued

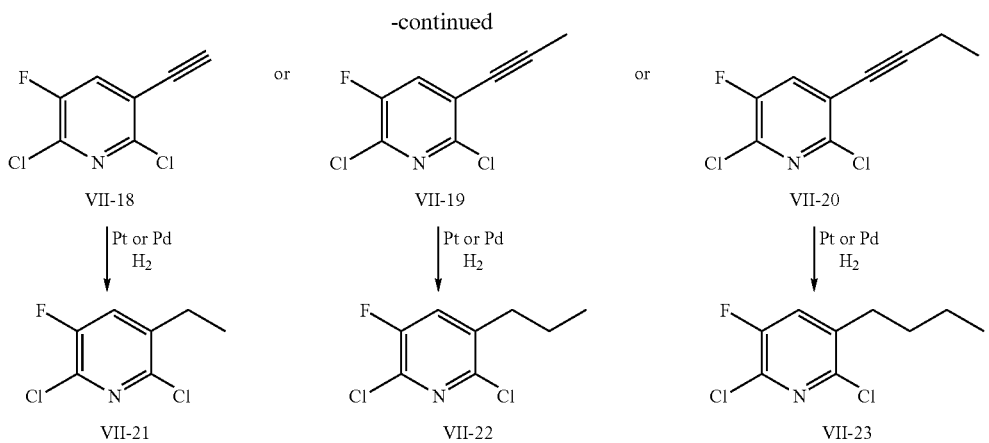

Compounds of formula W—NH$_2$ can be synthesized as follows. When R$^2$ is heteroaryl or phenyl, and C(R$^1$)$_2$ is CF$_2$, amines W—NH$_2$ can be synthesized as described in Scheme VIIb (WO 2004091613, *J. Org. Chem.* 68:8838, 2003, *Org. Process Res. Dev.* 8:192, 2004, and references therein.) For example, (hetero)aryl halides (iodides, but also 2-bromopyridines and 2-bromopyrimidines) VIIb-1 are converted to difluoro derivatives VIIb-2 in the presence of copper (*Chem. Pharm. Bull.* 47:1013, 1999; 48:982, 2000). These esters VIIb-2 can be converted to the amine targets VIIb-3 via borane reduction of the amide (if no ring nitrogen; WO 2004091613) or via activation of the alcohol followed by substitution by nucleophilic nitrogen (*Org. Process Res. Dev.* 8:192, 2004; WO 2004091613). Commercial halides suitable for the copper-mediated reaction include but are not limited to those labeled "VIIb-4 to VIIb-6" (16 halides are listed; the analogous meta- and para-substituted iodides are also often commercially available).

Amines VIIb-10 (fluorine or hydrogen substituted) are accessible from commercial toluenes VIIb-7 (fluorine or hydrogen substituted) via bromination to VIIb-8 (*Collect. Czech. Chem. Commun.* 64:649, 1999; *J. Med. Chem.* 47:612, 2004). Displacement with a glycine derivative (*J. Labelled Compd. Radiopharm.* 36:685, 1995; *J. Org. Chem.* 67:674, 2002), followed by Boc protection of the secondary amine affords VIIb-9. The standard multistep sequence (described for conversion of VIIb-1 to VIIb-3) then provides the target amines VIIb-10.

Amines VIIb-13 (fluorine or hydrogen substituted) are accessible via sequential cyanide attack on the benzyl bromide VIIb-8 (*Collect. Czech. Chem. Commun.* 45:504, 1980) to afford nitrile VIIb-11, hydrolysis to the acid VIIb-12 (*J. Org. Chem.* 64:4830, 1999), isobutylene-mediated conversion to the t-butyl ester under acidic conditions, and finally the standard multistep sequence (described for conversion of VIIb-1 to VIIb-3) to install the difluoroethylamine moiety. Amine VIIb-15 is accessible via PtO$_2$-mediated pyridine ring reduction (*J. Org. Chem.* 51:1889, 1986) of known VIIb-14 (WO 2004091613).

Scheme VIIb

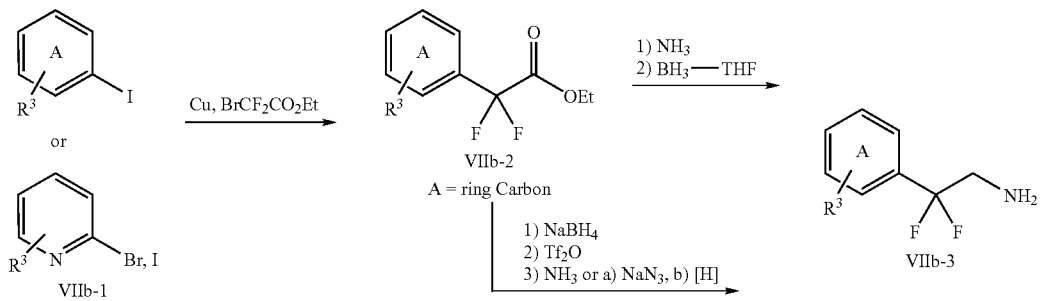

 is phenyl or heteroaryl

-continued

Commercially available precursors

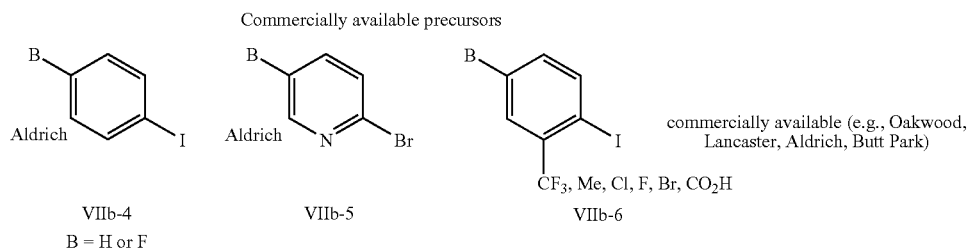

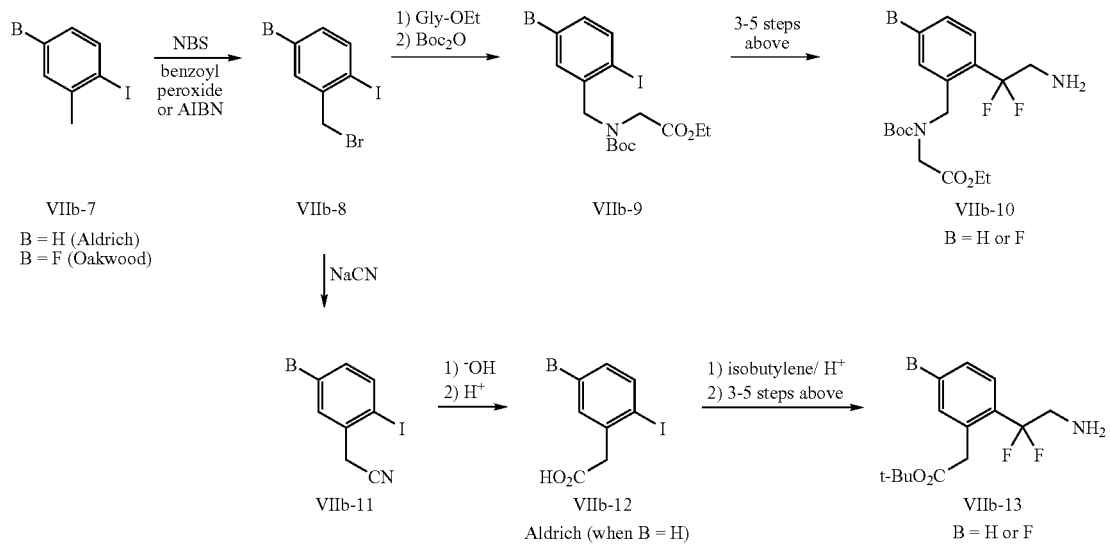

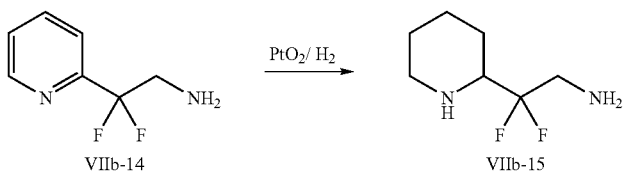

Scheme VIIc describes how t-butyl ester- and t-butyl carbamate-containing molecules can be converted to final target free acids or prodrug esters. Tert-Butyl ester amines VIIc-1 (such as VIIb-13) are heated in DMSO with DIPEA and V-10 to afford the $S_NAr$ products, which are then treated with acid to liberate the desired free acids VIIc-2. Treatment of VIIc-2 with acidic ethanol (*Tetrahedron* 57:5321, 2001) provides the ethyl esters VIIc-3, treatment of VIIc-2 with morpholinoethanol and a carbodiimide such as DCC (*J. Pharm. Sci.* 83:644, 1994) affords the morpholinoethyl esters VIIc-4, and treatment of VIIc-2 with 1-haloethyl acetate under basic conditions (*J. Antibiotics* 53:1086, 2000) yields the 1-acetoxyethyl acetates VIIc-5. Amine VIIb-10 is heated with V-10 under $S_NAr$ conditions and treated with acid as described for VIIc-2 to provide the ethyl ester VIIc-6. Treatment of VIIc-6 with aqueous alkali provides the amino acid VIIc-7.

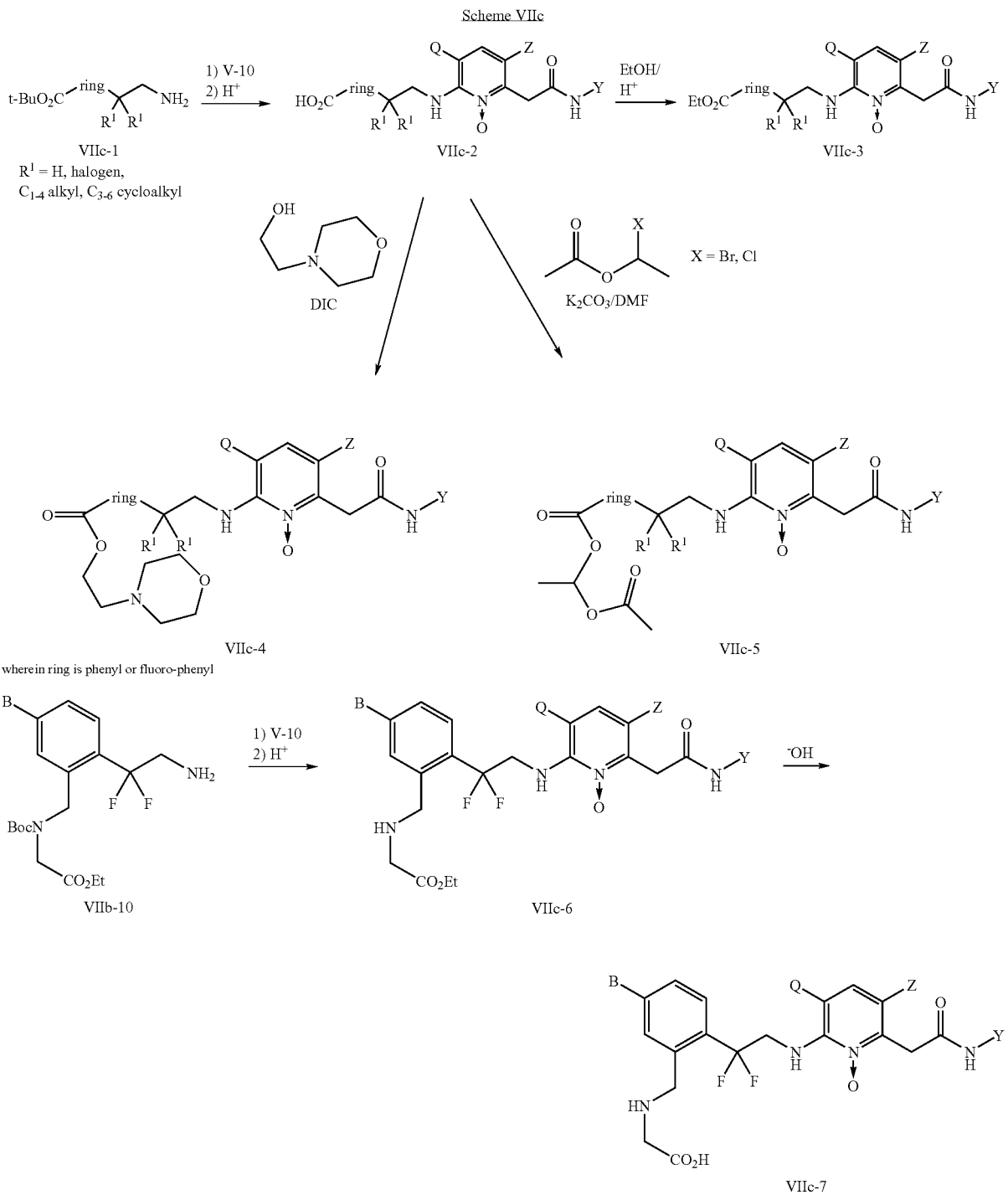

When $R^2$ is heteroaryl or phenyl, and $C(R^1)_2$ is $C(CH_3)_2$ or C(cycloalkyl), amines W—$NH_2$ can be synthesized as described in Scheme VIId. (Hetero)aryl fluorides VIId-1 (when known or commercially available) are treated with a secondary nitrile (branched at the position alpha to the nitrile) and KHMDS to afford tertiary nitriles VIId-2 (*J. Am. Chem. Soc.* 122:712, 2000), which are then reduced with LAH or Pd/C/$H_2$ under standard conditions to afford the amines VIId-3. Pyridine nitrile VIId-4 is reduced with LAH or Pd/C/$H_2$ under standard conditions to afford amine VIId-5. Reduction of the pyridine ring of VIId-5 with $PtO_2/H_2$ (*J. Org. Chem.* 51:1889, 1986) provides piperidine VIId-6. Piperidine VIId-7 is commercially available (Tyger Scientific). $S_NAr$ reaction of piperidine amines VIIb-15, VIId-6, and VIId-7 with chloropyridine N-oxide V-10 would be expected to proceed with predominant attack by the primary amine rather than the secondary amine of VIIb-15, VIId-6, and VIId-7 for steric reasons.

Scheme VIId

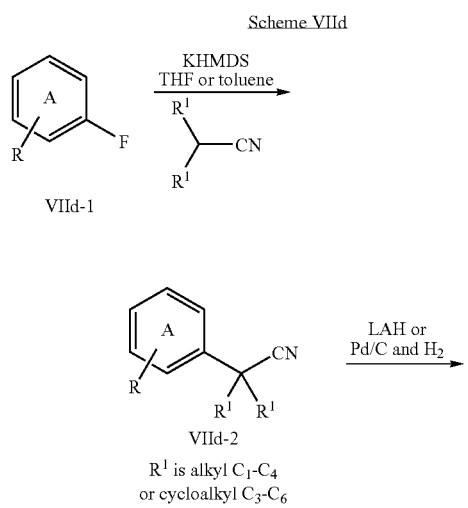

$R^1$ is alkyl $C_1$-$C_4$
or cycloalkyl $C_3$-$C_6$

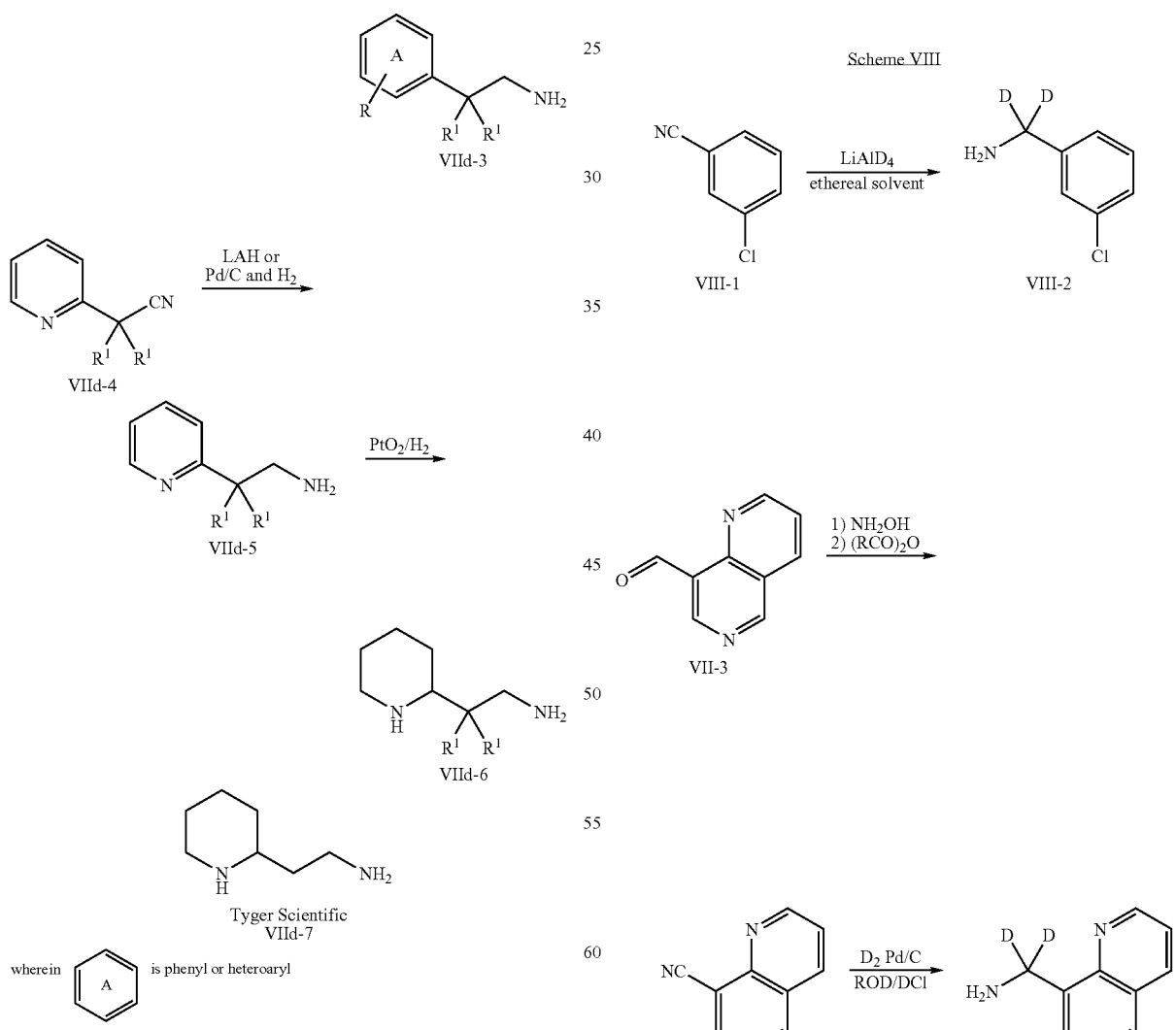

wherein [A] is phenyl or heteroaryl

Compounds of formula Y—NH$_2$ can be synthesized as disclosed herein or by known methods (WO 2004091613 A2). Scheme VIII shows the preparation of the three dideuterated amines VIII-2, VIII-5, and VIII-8 of formula Y—NH$_2$ that are described above. The starting materials are known VIII-1 (Aldrich), VIII-3 (US 2003/0158218A1; prior to reduction to 8-hydroxymethyl-1,6-napthyridine with DIBAL), and VIII-7 (Alfa Aesar).

Compound VIII-2 can be prepared from VIII-1 using LiAlD$_4$ at room temperature in an ethereal solvent such as THF (*J. Med. Chem.* 43:1754, 2000). Aldehyde VIII-3 can be converted to nitrile VIII-4 under standard conditions of hydroxylamine to form the intermediate oxime followed by an anhydride to eliminate water (*J. Org. Chem.* 58:4642, 1993). Nitrile VIII-4 can be converted to VIII-5 using either reduction with D$_2$ in the presence of Pd/C or Raney nickel catalysis with basic deuterated solvent (*J. Med. Chem.* 45:461, 2003; *J. Am. Chem. Soc.* 105:7435, 1983), or using LiAlD$_4$ as described above. Compound VIII-7 can be converted to VIII-8 using reduction of D$_2$ in the presence of Pd/C (*J. Med. Chem.* 46:461, 2003).

-continued

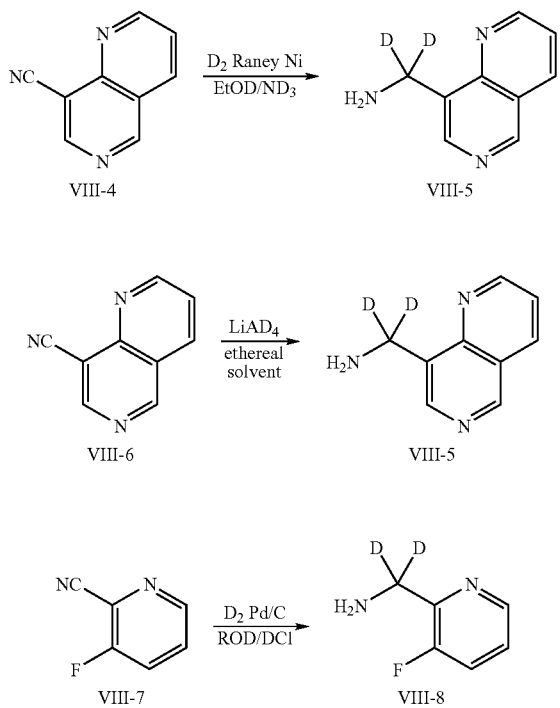

Scheme IX shows the asymmetric synthesis of the six chiral monodeuterated amines IX-6 IX-7, IX-8, IX-9, IX-12, and IX-13 of formula Y—NH$_2$ that are described above. Starting material IX-1 is commercially available (Aldrich). Starting material aldehyde IX-2 has been described above as VIII-3 in Scheme VIII (US 2003/0158218A1). Starting material IX-10 is commercially available (Frontier Scientific).

The asymmetric reduction of aryl aldehydes to monodeuterated benzyl alcohols with formic acid-D$_2$/TEA and a chiral ruthenium catalyst in CH$_3$CN has been reported to proceed under mild conditions on the gram scale in high yield (>90%), high enantiomeric excess (97-99% ee), and with established absolute stereochemistry (5 examples) (*Org. Lett.* 2:3425, 2000, and references therein). The ruthenium catalyst is easily prepared in both chiral configurations [(R,R)-IX-3 and (S,S)-IX-3] from commercially available dichloro(p-cymene)ruthenium(II) dimer (Aldrich, Strem) and commercially available (1S,2S)-(+)-N-p-Tosyl-1,2-diphenylethylenediamine (S,S-TsDPEN) (Aldrich, Strem) or (1R,2R)-(−)-N-p-Tosyl-1,2-diphenylethylenediamine (R,R-TsDPEN) (Aldrich, Strem) (*J. Am. Chem. Soc.* 118:2521, 1996). The resulting S-configuration monodeuterated alcohols IX-4, IX-5, and IX-11 can then be converted to the amine targets IX-6, IX-7, and IX-12 with the opposite (R) configuration, via activation of the alcohol as the sulfonate (e.g., mesylate or triflate), then displacement with either azide (*J. Org. Chem.* 20:6781, 2004) or concentrated ammonia in a protic solvent (*J. Am. Chem. Soc.* 125:12110, 2003). Note: Only the S-alcohols from the (R,R)-IX-3 ruthenium catalyst are drawn. The R-alcohols are synthesized from the same aldehyde starting materials IX-1, IX-2, and IX-10, but using the (S,S)-IX-3 catalyst (not drawn). These are then converted to the S-configuration amine targets IX-8, IX-9, and IX-13 exactly as described for the R-amine targets IX-6, IX-7, and IX-12.

Scheme IX

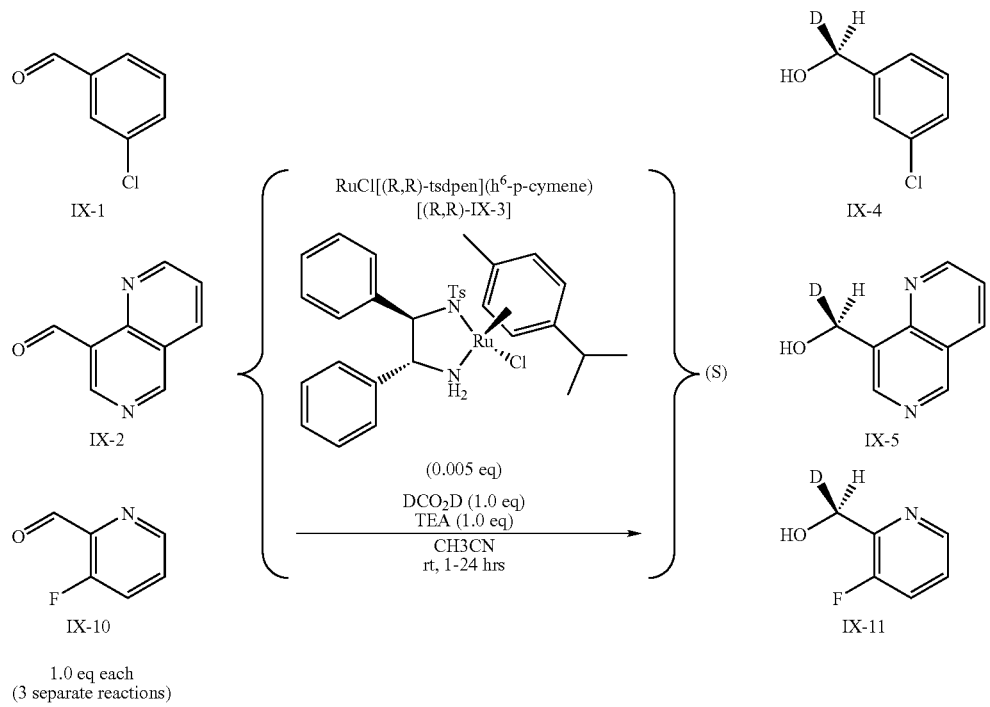

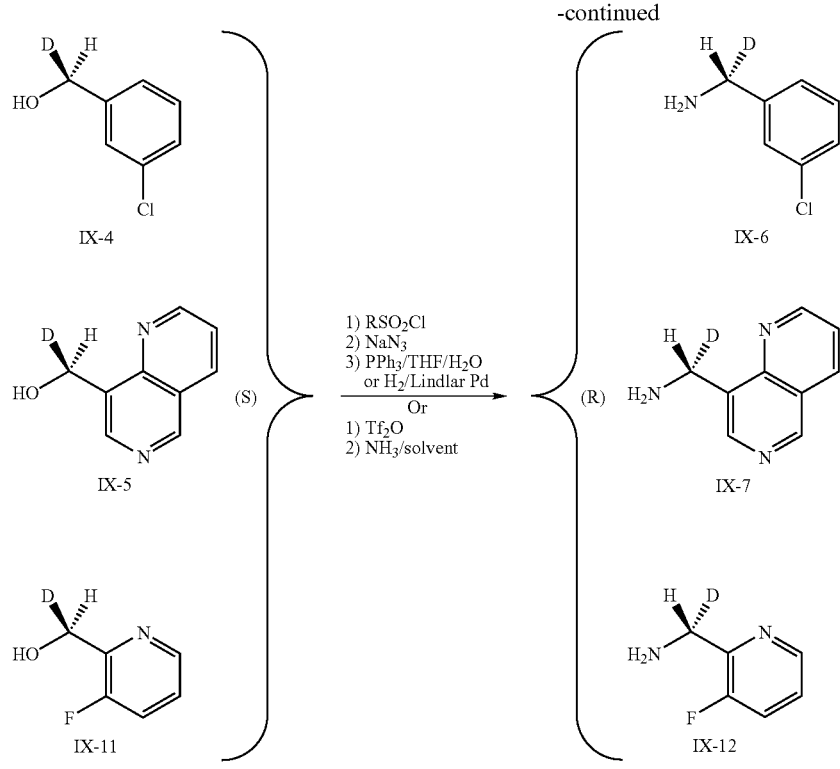

EXAMPLE 1

3-cyano-6-(2,2-difluoro-2-phenyl-ethylamino)-2-{2-[(aminoiminomethyl)aminooxy]ethyl}aminocarbonylmethyl-pyridine 1-oxide (Cpd 1)

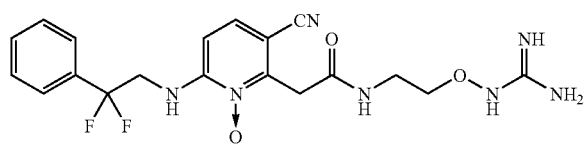

Step A 3-cyano-6-(2,2-difluoro-2-phenyl-ethylamino)-2-(2-{[(tert-butoxycarbonyl)amino-(tert-butoxycarbonyl)iminomethyl]aminooxy}ethyl)aminocarbonylmethyl-pyridine 1-oxide

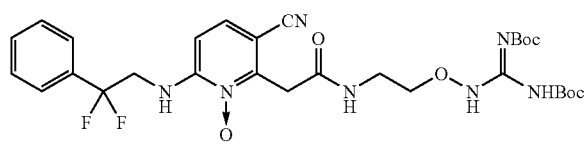

The title compound was prepared as described in Example 6i-j, using the HCl salt of ({[(tert-butoxycarbonyl)amino-(tert-butoxycarbonyl)iminomethyl]aminooxy}ethyl)amine (WO 2004/091613 A2) and 2,2-difluoro-2-phenyl-ethylamine (WO 2004/091613 A2; prepared from iodobenzene as described in detail for 1-chloro-3-iodobenzene).

Step B 3-cyano-6-(2,2-difluoro-2-phenyl-ethylamino)-2-{2-[(aminoiminomethyl)aminooxy]ethyl}aminocarbonylmethyl-pyridine 1-oxide A premixed solution of 0.5 mL TFA/0.5 mL DCM/0.1 mL anisole was added to 3-cyano-6-(2,2-difluoro-2-phenyl-ethylamino)-2-(2-{[(tert-butoxycarbonyl)amino-(tert-butoxycarbonyl)iminomethyl]aminooxy}ethyl)aminocarbonylmethyl-pyridine 1-oxide (32.6 mg, 51.5 μmol), as prepared in the previous step, and the homogeneous yellow solution was stirred at rt for 1 h. The reaction was then concentrated under reduced pressure, taken up in anisole (2 mL) and concentrated under vacuum, and the residue was purified by silica flash chromatography (10 mm×7" column; 9:1 DCM/MeOH/saturated NH₃ eluent; 5 mL fractions; fractions 10-13 combined) to yield the title compound as an off-white solid (14.3 mg, 64%). $^1$H-NMR (300 MHz, CD$_3$OD) δ 7.59-7.42 (m, 6H), 6.94 (d, 1H), 4.14 (t, J=13.7 Hz, 2H), 4.06 (s, 2H), 3.81 (m, 2H), 3.43 (m, 2H). LC/MS (ESI): calcd mass 433.2. found 434.5 (MH)$^+$.

EXAMPLE 2

3-chloro-6-(2,2-difluoro-2-phenyl-ethylamino)-2-{2-[(aminoiminomethyl)aminooxy]ethyl}aminocarbonylmethyl-pyridine 1-oxide (Cpd 2)

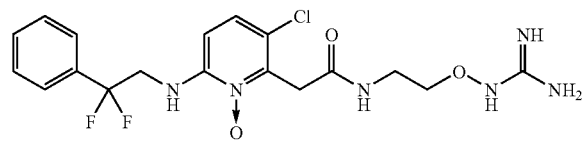

Step A (3,6-dichloro-pyridin-2-yl)-acetic Acid Ethyl Ester

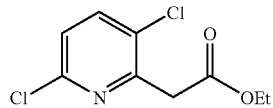

Malonic acid t-butyl ester ethyl ester (7.1 mL, 36 mmol) was added via syringe over one minute with swirling to a frozen mixture of NaH (968 mg, 38.3 mmol) in DMSO (10 mL) at 0° C. The ice bath was removed and the mixture was stirred at rt for 15 min, and then at 115° C. for less than a minute until H$_2$ evolution had subsided, and was then allowed to cool to rt. A solution of 2,3,6-trichloropyridine (3.26 g, 17.9 mmol) (J. Chem. Soc. C: Organic 1375, 1970) in DMSO (12 mL) was added, and the reaction stirred at 115° C. for 4 h. The reaction was then cooled to rt, shaken with 0.5 M NaH$_2$PO$_4$ (100 mL), and extracted with ether (1×50 mL; 2×25 mL). The organic layers were combined, washed with brine (1×20 mL), dried (Na$_2$SO$_4$), and concentrated under high vac at 95° C. to give a mixture of dichloro-pyridin-2-yl-malonic acid tert-butyl ester ethyl ester regioisomers as a clear amber oil (6.40 g) that was immediately used in the next step without further purification or characterization.

A portion of this mixture of malonate adduct regioisomers (5.79 g) was taken up in water (2.5 mL) and TFA (13 mL), and stirred at 55° C. for 10 min. The reaction was then cooled on an ice bath while 2 M K$_2$CO$_3$ (50 mL) was added portionwise with swirling. After vigorously shaking with periodic pressure release, the neutralized mixture was extracted with ether (2×60 mL), the organic layers were combined, dried (Na$_2$SO$_4$), and concentrated. The residue was taken up in minimal toluene and purified with silica flash chromatography (7:1→5:1 Hex/EtOAc) to afford the title compound as a pale yellow clear oil (1.98 g, 52% over 2 steps).

Step B

[3-chloro-6-(2,2-difluoro-2-phenyl-ethylamino)-pyridin-2-yl]-acetic Acid Ethyl Ester

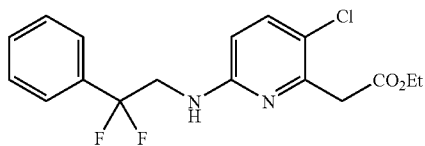

A mixture of (3,6-dichloro-pyridin-2-yl)-acetic acid ethyl ester (139 mg, 593 μmol), as prepared in the previous step, 2,2-difluoro-2-phenylethylamine (132.5 mg, 844 μmol) (see Example 8a), K$_3$PO$_4$ (317 mg, 1.50 mmol) (Fluka, Catalog # 04347), Pd(OAc)$_2$ (5.8 mg, 26 μmol), biphenyl-2-yl-dicyclohexyl-phosphane (22 mg, 62 μmol) (Strem) was taken up in dry, argon-sparged dioxane (650 μL), and the mixture was sealed under a blanket of argon. The yellowish heterogeneous mixture was microwaved with stirring (Smith Synthesizer) at 150° C. for 20 min, and the resulting amber-red heterogeneous mixture was diluted with 8 mL ether, filtered, and concentrated. Flash silica chromatography of the residue (6:1 hexanes/EtOAc eluent) afforded the title compound as a light yellow oil (128 mg, 61%).

Step C

[3-chloro-6-(2,2-difluoro-2-phenyl-ethylamino)-pyridin-2-yl]-acetic Acid Phenyl Ester

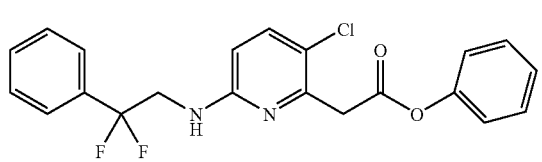

A mixture of [3-chloro-6-(2,2-difluoro-2-phenyl-ethylamino)-pyridin-2-yl]-acetic acid ethyl ester (125.2 mg, 353 μmol), as prepared in the previous step, MeOH (1.16 mL), and 1.0 M KOH (aq) (388 μL) was stirred at 50° C. for 2 h. The resulting pale yellow solution was then concentrated under rotary evaporation (carefully, to avoid "bumping"), and the residue was taken up with toluene (3×2 mL) and concentrated each time to provide the potassium carboxylate salt as a yellowish solid that was used without further purification or characterization.

A mixture of the above potassium carboxylate salt (assume 353 μmol), cis-dicyclohexano-18-crown-6 (6.0 mg, 16 μmol), BOP (241 mg, 545 μmol), phenol (37.9 mg, 403 μmol), and DMF (200 μL) were stirred for 1-2 min at rt, and then DIPEA (180 μL, 1.03 mmol) was added in one portion. The mixture was shaken overnight at rt, and the resulting beige slurry was diluted with 1 M NaH$_2$PO$_4$ (2 mL) and extracted with ether (1×4 mL) and EtOAc (2×2 mL). The combined organic layers were dried (2×Na$_2$SO$_4$) and concentrated under reduced pressure. Flash silica chromatography of the residue (6:1 hexanes/EtOAc eluent) provided the title compound as a light yellow oil (115 mg, 81%).

Step D 3-chloro-6-(2,2-difluoro-2-phenyl-ethylamino)-2-phenoxycarbonylmethyl-pyridine 1-oxide

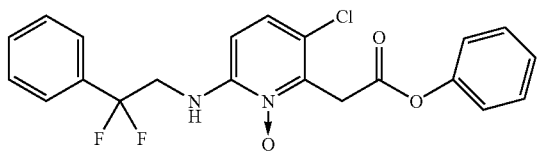

A solution of 3-chloro-6-(2,2-difluoro-2-phenyl-ethylamino)-2-phenoxycarbonylmethyl-pyridine 1-oxide (70.0 mg, 174 μmol), as prepared in the previous step, MCPBA (47.9 mg, 69.5% w/w, 193 μmol), and CDCl₃ (200 μL) was stirred at 60° C. for 40 min. The resulting amber homogeneous solution was applied to a silica flash column (3:2 hexanes/EtOAc eluent) to afford the title compound (45 mg, 62%).

Step E

Aminoethoxy-guanidine Dihydrochloride

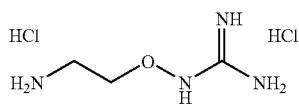

The HCl salt of ({[(tert-butoxycarbonyl)amino-(tert-butoxycarbonyl)iminomethyl]aminooxy}ethyl)amine (90.5 mg, 255 μmol) (WO 2004/091613 A2) was treated with 12 M HCl (aq) (210 μL, 2.5 mmol) in one portion at rt, and was then stirred at rt for 20 min. The resulting thick white slurry was concentrated under rotary evaporation at rt, and the residue was taken up in toluene (3×3 mL) with repeated rotary evaporation and high vacuum to yield the title compound as an off-white powder (52.9 mg, quantitative yield).

Step F 3-chloro-6-(2,2-difluoro-2-phenyl-ethylamino)-2-{2-[(aminoiminomethyl)aminooxy]ethyl}aminocarbonylmethyl-pyridine 1-oxide

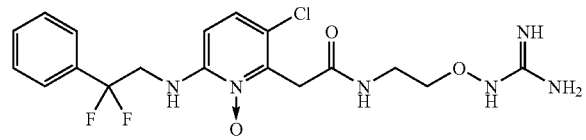

A mixture of 3-chloro-6-(2,2-difluoro-2-phenyl-ethylamino)-2-phenoxycarbonylmethyl-pyridine 1-oxide (41.2 mg, 98.4 μmol), as prepared in Example 2d, N-[2-(amidinoaminooxy)ethylamine dihydrochloride (32.9 mg, 172 μmol), as prepared in the previous step, MeOH (0.50 mL), and DIPEA (66 μL, 379 μmol) were stirred at 70° C. for 40 min. The homogeneous dark amber solution yielded a heavy white precipitate. Application of this crude reaction mixture to a silica flash column (95:5 DCM/MeOH with saturated NH₃ as eluent) yielded the title compound as an off-white solid (6.5 mg, 15%). ¹H-NMR (300 MHz, CD₃OD) δ 7.58-7.42 (m, 5H), 7.35 (d, 1H), 6.83 (d, 1H), 4.06 (t, J=13.7 Hz, 2H), 4.08 (s, 2H), 3.79 (t, 2H), 3.41 (t, 2H). LC/MS (ESI): calcd mass 442.1. found 443.3 (MH)⁺.

EXAMPLE 3

3-cyano-6-(2,2-difluoro-2-pyridin-2-yl-ethylamino)-2-(3-Amino-benzo[d]isoxazol-5-ylmethyl)aminocarbonylmethyl-pyridine 1-oxide (Cpd 3)

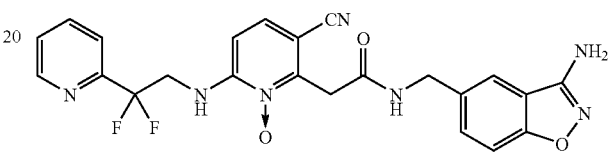

Step A 5-methyl-benzo[d]isoxazol-3-ylamine

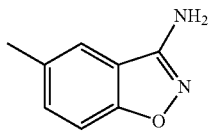

To a solution of 1 M potassium tert-butoxide in THF (40.7 mL, 40.7 mmol) was added acetone oxime (2.97 g, 40.7 mmol) in one portion. After stirring for 20 min at rt, a solution of 2-fluoro-5-methylbenzonitrile (5.0 g, 37.0 mmol) in THF (30 mL) was slowly added from an addition funnel. After stirring for 3 hrs at room temperature, the mixture was heated at 60° C. overnight. A dark brown solution was obtained. The reaction was quenched with water (10 mL). The reaction mixture was partitioned between saturated NaHCO₃ solution (50 mL) and ethyl acetate (150 mL). The organic layer was separated and washed with water (3×30 mL) and the solvent was removed on a rotary evaporator to yield a brown solid. The solid was then treated with a mixture of EtOH (80 mL), H₂O (53 mL) and HCl (12 N, 26.8 mL) at reflux for 2 hrs. After cooling, the reaction mixture was basified with solid sodium carbonate and NaOH (1 N, 30 mL). The reaction mixture was then extracted with ethyl acetate (2×100 mL). The organic layer was washed with water (2×30 mL) and brine (40 mL), then dried over anhydrous sodium sulfate. Rotary evaporation of solvent afforded a brown solid (4.6 g). LC/MS (ESI) (M+H⁺+CH₃CN: 190.0). This product was used without further purification.

Step B

Bis-tert-butoxycarbonyl-(5-methyl-benzo[d]isoxazol-3-yl)-amine

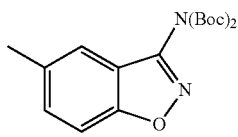

To a solution of 5-methyl-benzo[d]isoxazol-3-ylamine (4.6 g) in anhydrous DCM (50 mL) was slowly added a solution of (Boc)$_2$O in anhydrous DCM (50 mL) and 50 mg of DMAP. After refluxing overnight, TLC showed complete reaction. LCMS/ELSD showed formation of the desired product (M+H: 349.2). The reaction was quenched with aqueous sodium carbonate (1 M, 50 mL) and stirred for 1 hr at room temperature. The organic layer was dried over anhydrous sodium sulfate. After rotary evaporation of most solvent, the concentrated solution was loaded onto a 50 g ISOLUTE silica cartridge and eluted with EtOAc/Hexane (from 1:10 to 1:2). Rotary evaporation of solvent provided a light yellow solid. Trituration with EtOAc/Hexane (1:9) provided a white solid (4.56 g). $^1$H-NMR (300 MHz, CDCl$_3$) δ 7.47 (d, 1H), 7.40 (d, 1H), 7.37 (s, 1H), 2.48 (s, 3H), 1.41 (s, 18H). LC/MS (ESI): M+H$^+$ 349.2.

Step C

Bis-tert-butoxycarbonyl-(5-bromomethyl-benzo[d]isoxazol-3-yl)-amine

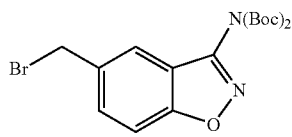

A solution of bis-tert-butoxycarbonyl-(5-methyl-benzo[d]isoxazol-3-yl)-amine (1.08 g) in CCl$_4$ was placed under vacuum and sparged with Argon. To this solution was added NBS (0.58 g) and benzoyl peroxide (50.6 mg). The suspension was stirred at reflux overnight, after which time TLC indicated a new major spot. After cooling to rt, solid was filtered off and washed with DCM. The solution was concentrated and loaded onto a 20 g ISOLUTE silica cartridge and eluted with Hexane/DCM (from 3:2 to 1:4). Rotary evaporation of solvent afforded a light tan solid (1.12 g). This product was used without further purification.

Step D

2-[3-(bis-tert-butoxycarbonyl)-amino-benzo[d]isoxazol-5-ylmethyl]-isoindole-1,3-dione

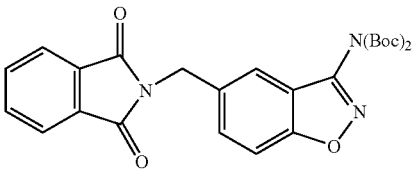

To a solution of bis-tert-butoxycarbonyl-(5-bromomethyl-benzo[d]isoxazol-3-yl)-amine (1.12 g) in anhydrous DMF (15 mL) was added phthalimide (297 mg) and cesium carbonate (2.63 g). The reaction mixture was stirred at room temperature overnight, after which time TLC indicated a new major spot. The solid was filtered off. The solvent was removed by rotary evaporation and the residue was re-dissolved in EtOAc (100 mL) and extracted with water (30 mL), 1 N NaOH (20 mL), water (2×20 mL) and brine (25 mL). The organic layer was dried over anhydrous sodium sulfate. Rotary evaporation of solvent resulted a brown gummy solid (1.31 g). LC/MS (ESI) (M+H$^+$ 494.1) indicated presence of the desired product. This product was used without further purification.

Step E (5-Aminomethyl-benzo[d]isoxazol-3-yl)-carbamic Acid Tert-butyl Ester

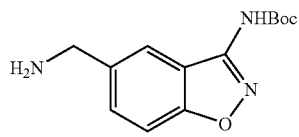

A mixture of 2-[3-(tert-butoxycarbonyl)amino-benzo[d]isoxazol-5-ylmethyl]-isoindole-1,3-dione (1.31 g) and hydrazine hydrate (2.52 mL, 52 mmol) in 1-butanol (10 mL) was stirred at room temperature. The mixture turned into a translucent orange solution. After stirring for about 1 hr, white precipitate formed. The mixture was then heated to reflux for 5 min and all solid dissolved. After cooling, DCM was added, after which time white precipitate formed. The solid was filtered off and washed with DCM. Rotary evaporation afforded a yellow oil. The oily residue was taken up with EtOAc (100 mL) and washed with water (3×30 mL), brine (30 mL) and dried over anhydrous sodium sulfate. Most solvent was removed on a rotary evaporator and the remainder was loaded onto a 20 g ISOLUTE silica cartridge. The product was eluted with (2 M ammonia in methanol)/DCM (4:96). A light yellow solid was obtained (330 mg). $^1$H-NMR (300 MHz, CDCl$_3$) δ 8.05 (s, 1H), 7.53 (d, 1H), 7.45 (d, 1H), 7.31 (s, 1H), 3.40 (s, 2H), 1.57 (s, 9H).

Step F 3-cyano-6-chloro-2-[3-(tert-butoxycarbonyl)amino-benzo[d]isoxazol-5-ylmethyl]aminocarbonylmethyl-pyridine 1-oxide

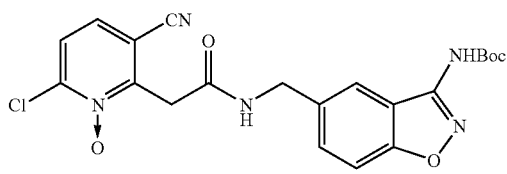

A mixture of 6-chloro-3-cyano-2-(4-nitro-phenoxycarbonylmethyl)-pyridine 1-oxide (83.6 mg, 0.25 mmol), as prepared in Example 6f, and (5-aminomethyl-benzo[d]isoxazol-3-yl)-carbamic acid tert-butyl ester (78.8 mg, 0.3 mmol) in CDCl₃ (3 mL) was stirred in an ice-water bath which was allowed to rise to rt overnight. A lot of precipitate formed. TLC showed the disappearance of 6-chloro-3-cyano-2-(4-nitro-phenoxycarbonylmethyl)-pyridine 1-oxide. A small amount of methanol was added to dissolve the solid. The solution was applied onto a prep TLC (2 mm, 20×20 cm) and developed with EtOAc/Hexane (4:1). A white solid was obtained (103 mg). LC/MS (ESI) (M+H⁺ 458.1)

Step G 3-cyano-6-(2,2-difluoro-2-pyridin-2-yl-ethylamino)-2-[3-(tert-butoxycarbonyl)amino-benzo[d]isoxazol-5-ylmethyl]aminocarbonylmethyl-pyridine 1-oxide

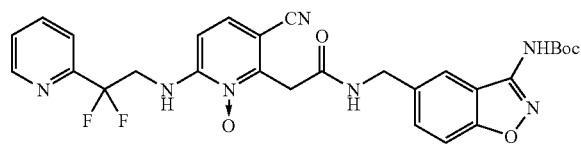

A mixture of 3-cyano-6-chloro-2-[3-(tert-butoxycarbonyl)amino-benzo[d]isoxazol-5-ylmethyl]aminocarbonylmethyl-pyridine 1-oxide (103 mg, 0.225 mmol) and 2,2-difluoro-2-pyridin-2-yl-ethylamine (89 mg, 0.534 mmol) (*Organic Process Research & Development* 8:192-200, 2004), in DMSO (3 mL) was stirred for 18 hrs at 80° C. LC/MS (ESI) (M+H⁺ 580.2) indicated the formation of desired product. After removing most DMSO by high-vacuum rotary evaporation, water was added, after which time precipitate formed. The liquid was loaded onto a 5 g FisherBrand PrepSep SPE C18 cartridge. The solid was washed with water a few times. The washes were also loaded onto the cartridge. The cartridge was then washed with water (40 mL), acetonitrile (20 mL), mixture of acetonitrile/DCM (1:1, 20 mL) and DMF (10 mL). All organic washes were combined and stripped off solvent by rotary evaporation. An orange solid was obtained and used without further purification. LC/MS (ESI): M+H⁺ 580.1.

Step H 3-cyano-6-(2,2-difluoro-2-pyridin-2-yl-ethylamino)-2-(3-amino-benzo[d]isoxazol-5-ylmethyl)aminocarbonylmethyl-pyridine 1-oxide

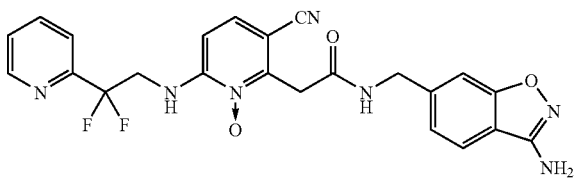

The product from the previous step was dissolved in anhydrous DCM (4 mL). To it, cooled in an ice-water bath, was slowly added a solution of 50% TFA in DCM (4 mL). After stirring for 5 min in the ice-water bath, the ice-water bath was removed. The reaction mixture was allowed to warm up to room temperature for 1 hr. LC/MS (ESI) indicated the disappearance of 3-cyano-6-(2,2-difluoro-2-pyridin-2-yl-ethylamino)-2-[3-(tert-butoxycarbonyl)amino-benzo[d]isoxazol-5-ylmethyl]aminocarbonylmethyl-pyridine 1-oxide and the presence of the desired product. The solvent and excess TFA was removed on a rotary evaporator. The liquid residue was re-dissolved in DCM and the solvent again removed on a rotary evaporator. Re-dissolved in (2M NH₃ in MeOH)/DCM (5:95, 2 mL) and loaded onto a 20 g ISOLUTE silica cartridge. The product was eluted with (2M NH₃ in MeOH)/DCM (5:95). Rotary evaporation of most solvent resulted the formation of a white solid. The solid was collected by filtration and washed with methanol. After vacuum drying, an off-white solid was obtained (42.4 mg). LC/MS (ESI): M+H+ 480.2. ¹H-NMR (300 MHz, DMSO) δ 8.81 (t, 1H), 8.73 (d, 1H), 8.32 (t, 1H), 8.02 (t, 1H), 7.77-7.67 (m, 3H), 7.61 (dd, 1H), 7.48 (d, 1H), 7.40 (d, 1H), 6.36 (s, 2H), 4.36 (m, 4H), 3.95 (s, 2H).

EXAMPLE 4

3-cyano-6-(2,2-difluoro-2-pyridin-2-yl-ethylamino)-2-(3-amino-benzo[d]isoxazol-6-ylmethyl)aminocarbonylmethyl-pyridine 1-oxide (Cpd 4)

Step A 2-fluoro-terephthalonitrile

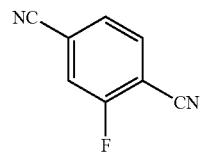

To a solution of 4-bromo-6-fluorobenzonitrile (5 g, 25 mmol) in anhydrous DMF (20 mL) was added Zinc cyanide (1.75 g, 14.9 mmol) and tetrakis(triphenylphosphine)-palladium(0) (0.6 g, 0.519 mmol). The reaction mixture was heated overnight under argon at 90° C. After cooling to room temperature, the reaction mixture was poured into ethyl acetate (150 mL) and extracted with water 50 mL, 2×30 mL, brine (30 mL), then dried over anhydrous sodium sulfate. After rotary evaporation of most solvent, the concentrated solution was loaded onto a silica column and eluted with EtOAc/Hexane (1:6). A white solid was obtained (3.73 g). $^1$H-NMR (300 MHz, CDCl$_3$) δ 7.80 (m, 1H), 7.58 (m, 2H).

Step B 3-amino-benzo[d]isoxazole-6-carbonitrile

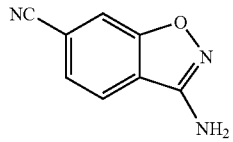

To a solution of 1 M potassium tert-butoxide in THF (11.0 mL, 11.0 mmol) was added acetone oxime (0.824 g, 11.3 mmol) in one portion. After stirring for 20 min at room temperature, a solution of 2-fluoro-terephthalonitrile (1.48 g, 10.1 mmol) in THF (11 mL) was slowly added through a syringe. The reaction mixture warmed up and turned into a red solution. After stirring for 1.5 hrs at room temperature, the mixture was heated at 60° C. for 1 hr. The reaction was quenched with a mixture of saturated ammonium chloride solution and water (1:1, 10 mL). THF was removed by rotary evaporation. The reaction mixture was then partitioned between ethyl acetate (30 mL) and brine (20 mL). The organic layer was separated and dried over anhydrous sodium sulfate. The solvent was then removed in vacuo to provide a yellow solid. The solid was then treated with a mixture of EtOH (22 mL) and HCl (1 N, 14 mL) at reflux for 1.5 hrs. After cooling to room temperature, the reaction mixture was basified with solid sodium carbonate and partitioned between ethyl acetate (100 mL) and water (20 mL). The aqueous layer was further extracted with ethyl acetate (2×25 mL). All organic layers were combined and extracted with water (3.25 mL), brine (30 mL) then dried over anhydrous sodium sulfate. Rotary evaporation of solvent afforded a light brown solid. LC/MS (ESI) showed the desired mass (M+H$^+$+CH$_3$CN: 201.1). All crude was dissolved in minimum amount of MeOH/DCM (5:95) and loaded onto a silica column. The product was eluted with (2 M NH$_3$ in MeOH)/DCM (5:95). A light brown solid was obtained (1.01 g).

Step C. 3-[(bis-tert-butoxycarbonyl)amino]-benzo[d]isoxazole-6-carbonitrile

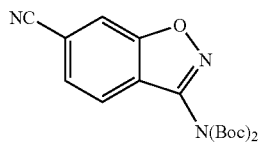

The title compound was prepared using the same procedure as for 10b. A white solid was obtained (2.74 g). LC/MS (ESI): M+H$^+$ 260.1. $^1$H-NMR (300 MHz, CDCl$_3$) δ 7.95 (s, 1H), 7.66 (dd, 2H), 1.42 (s, 18H).

Step D

3-[(bis-tert-butoxycarbonyl)amino]-6-aminomethyl-benzo[d]isoxazole

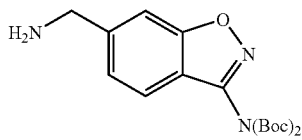

To a solution of 3-[(bis-tert-butoxycarbonyl)amino]-benzo[d]isoxazole-6-carbonitrile (359.4 mg, 1.0 mmol) in anhydrous THF (5 mL), cooled in an ice-water bath, was dropwise added 1 M BH$_3$.THF (3.0 mL, 3.0 mmol). The mixture was stirred overnight from 0° C. to room temperature. The reaction was quenched with 1 N HCl (8 mL) and stirred at r. for 30 min. Solid sodium carbonate was added until no bubble formation occurred. Then, 1 N NaOH was added until the pH was greater than 11. The mixture was extracted with ethyl acetate (2×25 mL). Combined organic layers were washed with brine (25 mL) and dried over sodium sulfate. Rotary evaporation afforded a yellow oil. Purified on a 25 g ISOLUTE silica cartridge with (2 M NH$_3$ in MeOH)/DCM (5:95). A yellow oil was obtained (180 mg). LC/MS (ESI): M+H$^+$ 364.2.

Step E. 3-cyano-6-chloro-2-[3-(tert-butoxycarbonyl)amino-benzo[d]isoxazol-6-ylmethyl]aminocarbonylmethyl-pyridine 1-oxide

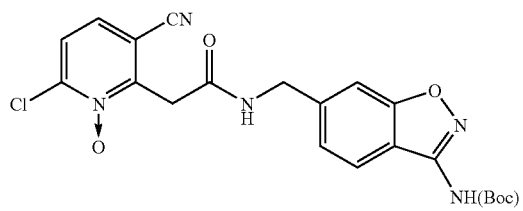

To a solution of 6-chloro-3-cyano-2-(4-nitro-phenoxycarbonylmethyl)-pyridine 1-oxide (66.7 mg, 0.2 mmol) in CDCl$_3$ (1 mL), cooled in an ice-water bath, was added a solution of 3-[(bis-tert-butoxycarbonyl)amino]-6-aminomethyl-benzo[d]isoxazole (90.8 mg, 0.25 mmol) in CDCl$_3$ (1 mL). The reaction mixture was stirred overnight from 0° C. to room temperature. Preparation TLC with EtOAc/Hex (5:2) afforded a yellow gummy solid (29 mg). LCAMS (ESI): M+H$^+$ 458.0, 558.1 and NMR showed a mixture of mono-Boc and b di-Boc products. This mixture was used without further purification.

Step F 3-cyano-6-(2,2-difluoro-2-pyridin-2-yl-ethylamino)-2-[3-(tert-butoxycarbonyl)amino-benzo[d]isoxazol-6-ylmethyl]aminocarbonylmethyl-pyridine 1-oxide

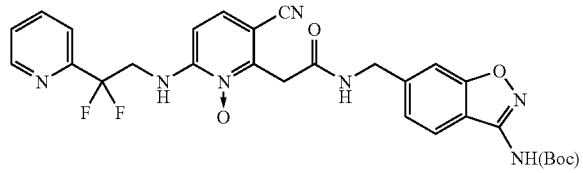

A mixture of 3-cyano-6-chloro-2-[3-(tert-butoxycarbonyl) amino-benzo[d]isoxazol-6-ylmethyl]aminocarbonylmethyl-pyridine 1-oxide (29 mg) and 2,2-difluoro-2-pyridin-2-yl-ethylamine (20 mg) (*Organic Process Research & Development* 8:192-200, 2004), in DMSO (0.5 mL) was heated overnight at 80° C. LC/MS (ESI) indicated the mono-Boc product (M+H$^+$ 580.1) as the major component. To the reaction vial was added DCM (10 mL) and water (3 mL). The mixture was vigorously stirred. After removing the aqueous layer, the organic layer was further washed with water (4×3 mL) to remove DMSO and water soluble components. Rotary evaporation of solvent afforded a syrupy residue that was used without purification. LCAMS (ESI) showed the mono-Boc product (M+H$^+$ 580.1) as the major component and the di-Boc product (M+H$^+$ 680.0) as a minor component.

Step G 3-cyano-6-(2,2-difluoro-2-pyridin-2-yl-ethylamino)-2-(3-amino-benzo[d]isoxazol-6-ylmethyl)aminocarbonylmethyl-pyridine 1-oxide

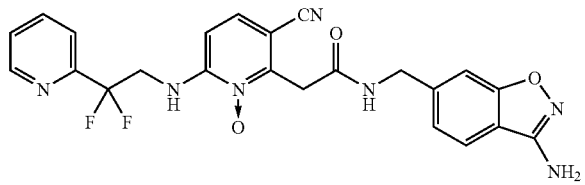

The crude product from the previous step was dissolved in anhydrous DCM (1 mL). To it, cooled in an ice-water bath, was slowly added a solution of 50% TFA in DCM (1 mL). After stirring for 5 min in the ice-water bath, the ice-water bath was removed. The reaction mixture was allowed to warm up to room temperature for 1 hr. LC/MS (ESI) indicated the disappearance of 3-cyano-6-(2,2-difluoro-2-pyridin-2-yl-ethylamino)-2-[3-(tert-butoxycarbonyl)amino-benzo[d]isoxazol-6-ylmethyl]aminocarbonylmethyl-pyridine 1-oxide and the presence of the desired product (M+H$^+$ 480.1). The solvent and excess TFA was removed on a rotary evaporator. The liquid residue was re-dissolved in DCM and the solvent again removed on a rotary evaporator. The residue was then redissolved in (2M NH$_3$ in MeOH)/DCM (4:96, 1 mL) and loaded onto a 20 g ISOLUTE silica cartridge. Eluted with (2M NH$_3$ in MeOH)/DCM (4:96). Rotary evaporation afforded a yellow solid (8.6 mg). LC/MS (ESI): M+H$^+$ 480.2. $^1$H-NMR (300 MHz, CDCl$_3$+CD$_3$OD) δ 8.66 (d, 1H), 7.89 (t, 1H), 7.70 (D, 1h), 7.63 (D, 1h), 7.56 (D, 1h), 7.48 (M, 1h), 7.35 (s, 1h), 7.17 (d, 1H), 7.05 (d, 1H), 4.52 (s, 2H), 4.31 (t, 2H), 4.09 (s, 2H).

EXAMPLE 5

3-cyano-6-(2,2-difluoro-2-pyridin-2-yl-ethylamino)-2-(1-Amino-isoquinolin-7-ylmethyl)aminocarbonyl-methyl-pyridine 1-oxide (Cpd 5)

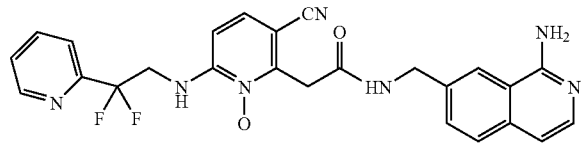

Step A 3-p-tolyl-acryloyl Azide

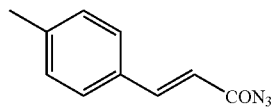

Triethylamine (8.5 mL, 60 mmol) was added slowly into the mixture of 3-p-tolyl-acrylic acid (8.3 g, 50 mmol) in 40 mL of acetonitrile followed by drop-wise addition of ethyl chloroformate (5.3 mL, 55 mmol) at 0° C. The solution was stirred for 2 h at this temperature. Sodium azide (6.5 g, 100 mmol) in 50 mL of water was added slowly to the above solution at 0° C. and the mixture was kept stirring for 1 h. Cold water was added and the precipitate was filtered and washed with cold water. The solid product (7.66 g, 82% yield) was obtained after being dried under vacuum. $^1$H-NMR (300 MHz, CDCl$_3$) δ 7.72 (d, 1H), 7.44 (d, 2H), 7.21 (d, 2H), 6.38 (d, 1H), 2.39 (s, 3H).

Step B 7-methyl-isoquinolin-1-ol

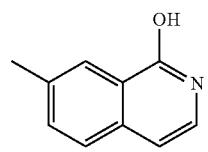

Into the refluxing solution of tributylamine (5 mL) and diphenyl ether (10 mL) was slowly added 3-p-tolyl-acryloyl azide (7.66 g, 40.1 mmol) in 10 mL of tributylamine and 20 mL of diphenyl ether. The reaction mixture was refluxed overnight and cooled down to rt. The above solution was diluted with hexane, the white solid (3.55 g, 55% yield) was collected by filtration and washed with 30% of methylene chloride in hexane.

Step C 1-chloro-7-methyl-isoquinoline

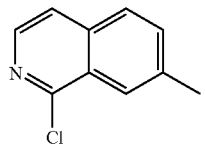

The solution of POCl$_3$ (10 mL) and 7-methyl-isoquinolin-1-ol (3.55 g, 22.3 mmol) was refluxed under nitrogen for 5 h. The residue, after removal of POCl$_3$ by distillation, was quenched with iced water and extracted with methylene chloride (3×). Purification by flash silica gel column using 10-25% EtOAc in hexane as elute gave 3.40 g (85% yield) of desired product. $^1$H-NMR (300 MHz, CDCl$_3$) δ 8.21 (d, 1H), 8.11 (s, 1H), 7.75 (d, 1H 7.60 (d, 1H), 7.55 (d, 1H), 2.60 (s, 3H).

Step D

Benzhydrylidene-(7-methyl-isoquinolin-1-yl)-amine

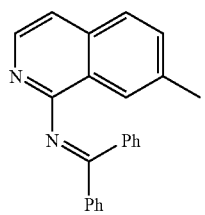

A mixture of 1-chloro-7-methyl-isoquinoline (800 mg, 4.5 mmol), Pd$_2$(dba)$_3$ (32 mg, 0.035 mmol), BINAP (69 mg, 0.11 mmol) and NaO$^t$Bu (670 mg, 7.0 mmol) in 2 mL of toluene was heated at 100° C. for 1 h under microwave. The solution was diluted with water and extracted with CH$_2$Cl$_2$. The concentrated residue was loaded to flash column and washed with 20% EtOAc in hexane. A yellow solid (1.01 g, 70% yield) was obtained.

Step E. 7-methyl-isoquinolin-1-ylamine

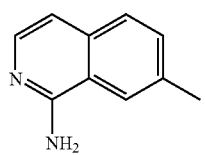

Benzhydrylidene-(7-methyl-isoquinolin-1-yl)-amine was dissolved in 11 mL of THF and 1.0 mL of 6M HCl (aq.) was added. The solution was stirred at rt overnight, diluted with CH$_2$Cl$_2$ and neutralized by using 1N aq. NaOH solution. Extraction with CH$_2$Cl$_2$ and concentration provided 460 mg (93% yield) of free amine after flash column purification. $^1$H-NMR (300 MHz, CDCl$_3$) δ 7.89 (d, 1H), 7.62 (d, 1H), 7.57 (s, 1H), 7.45 (d, 1H), 7.02 (d, 1H), 5.09 (br, 2H), 2.53 (s, 3H); LC/MS (ESI): calcd mass 158.1. found 159.0 (MH)$^+$.

Step F

Bis-tert-butoxycarbonyl-(7-methyl-isoquinolin-1-yl)amine

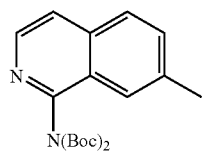

Into 676 mg (4.28 mmol) of 7-methyl-isoquinolin-1-ylamine and 10 mg of DMAP in 10 mL of CH$_2$Cl$_2$ was added 2.13 g (9.77 mmol) of (Boc)$_2$O. The mixture was refluxed overnight. The residue after removal of solvent was loaded to a silica gel column and 500 mg (33% conversion) of Boc-protected product was obtained along with 200 mg of recovered starting material. $^1$H-NMR (300 MHz, CDCl$_3$) δ 8.35 (d, 1H), 7.76 (d, 1H), 7.7 (s, 1H), 7.60 (d, 1H), 7.53 (d, 1H), 2.54 (s, 3H), 1.31 (s, 18H); LC/MS (ESI): calcd mass 358.2. found 359.2 (MH)$^+$.

Step G

Bis-tert-butoxycarbonyl-(7-bromomethyl-isoquinolin-1-yl)amine

A mixture of the bis-tert-butoxycarbonyl-(7-methyl-isoquinolin-1-yl)amine (500 mg, 1.40 mmol), N-bromosuccinimide (265 mg, 1.47 mmol) and 4 mg of benzoyl peroxide in 10 mL of CCl$_4$ was refluxed overnight. The solution was concentrated and loaded to a flash column using 10% EtOAc in hexane as eluent. This gave 440 mg (72% yield) of yellow solid product. $^1$H-NMR (300 MHz, CDCl$_3$) δ 8.44(d, 1H), 7.94 (s, 1H), 7.87 (d, 1H), 7.73 (d, 1H), 7.64 (d, 1H), 4.64 (s, 2H), 1.32 (s, 18H); LC/MS (ESI): calcd mass 436.1. found 437.1 (MH)$^+$.

Step H

Bis-tert-butoxycarbonyl-(7-azidomethyl-isoquinolin-1-yl)amine

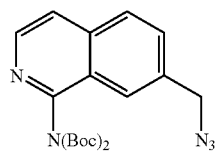

A mixture of bis-tert-butoxycarbonyl-(7-bromomethyl-isoquinolin-1-yl)amine (280 mg, 0.64 mmol) and NaN$_3$ (300 mg, 4.6 mmol) in 3 mL of DMSO was heated at 85° C. for 1 h. Then the solution was cooled down to rt, diluted with water and extracted with 50% EtOAc in hexane. The combined organic layers were washed with water. Removal of solvents furnished the crude product as a yellow oil (200 mg).

Step I

Bis-tert-butoxycarbonyl-(7-aminomethyl-isoquinolin-1-yl)amine

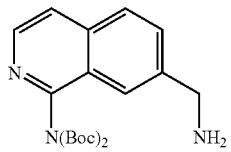

The bis-tert-butoxycarbonyl-(7-azidomethyl-isoquinolin-1-yl)amine, with 100 mg of Pd/C (10%) in 5 mL of MeOH was placed under 1 atmosphere of H$_2$ with efficient stirring for 2 h. The mixture was filtered through Celite. Removal of solvent on a rotary evaporator gave 188 mg of free amine. Without further purification, this intermediate was subjected to the next reaction.

Step J 3-cyano-6-chloro-2-[1-(bis-tert-butoxycarbonyl)amino-isoquinolin-7-ylmethyl]aminocarbonylmethyl-pyridine 1-oxide

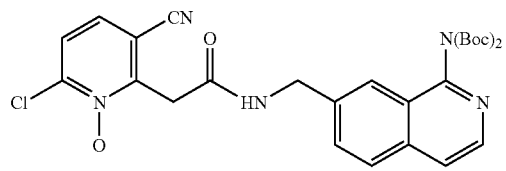

6-chloro-3-cyano-2-(4-nitro-phenoxycarbonylmethyl)-pyridine 1-oxide (110 mg, 0.33 mmol), as prepared in Example 6f, and bis-tert-butoxycarbonyl-(7-aminomethyl-isoquinolin-1-yl)amine (108 mg, 0.29 mmol) were dissolved in 4 mL of CDCl$_3$. The mixture was stirred at rt overnight. The solution was directly loaded to silica gel column. The flash column was washed with a mixture of 20-40% EtOAc and 2-5% MeOH (2M NH$_3$ in MeOH) in hexane. A yellow solid amide (90 mg, 55% yield) was obtained. $^1$H-NMR (300 MHz, CDCl$_3$) δ 8.41(d, 1H), 7.78 (d, 1H), 7.60 (m, 5H), 7.34 (d, 1H), 4.58 (d, 2H), 4.17 (s, 2H), 1.33 (s, 18H); LC/MS (ESI): calcd mass 567.2, found 468.1 (MH-Boc)$^+$.

Step K 3-cyano-6-(2,2-difluoro-2-pyridin-2-yl-ethylamino)-2-[1-(bis-tert-butoxycarbonyl)amino-isoquinolin-7-ylmethyl]aminocarbonylmethyl-pyridine 1-oxide

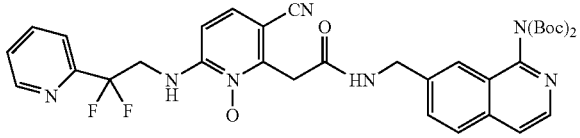

The 3-cyano-6-chloro-2-[1-(bis-tert-butoxycarbonyl)amino-isoquinolin-7-ylmethyl]aminocarbonylmethyl-pyridine 1-oxide (90 mg, 0.16 mmol) and 2,2-difluoro-2-pyridin-2-yl-ethylamine (55 mg, 0.35 mmol) (*Organic Process Research & Development* 8:192-200, 2004), was dissolved in 2 mL of DMSO and heated at 80° C. for 5 h. The solution was cooled down to rt, and diluted with water. A precipitate formed and was collected. The solid and silica gel was mixed with 1 ml of DMF. Then DMF was removed under vacuum. The residue was loaded to a flash column. The column was washed with 0-5% MeOH (2M NH$_3$ in MeOH). This gave 72 mg of product. $^1$H-NMR (300 MHz, CDCl$_3$) δ 8.66 (d, 1H), 8.20 (d, 1H), 8.57 (t, 1H), 7.97 (t, 1H), 7.78 (m, 6H), 7.44 (m, 2H), 6.88 (d, 1H), 4.58 (d, 2H), 4.31 (td, 2H), 4.16 (s, 2H), 1.30 (s, 18H); LC/MS (ESI): calcd mass 689.3. found 690.2 (MH)$^+$.

Step L 3-cyano-6-(2,2-difluoro-2-pyridin-2-yl-ethylamino)-2-(1-amino-isoquinolin-7-ylmethyl)aminocarbonyl-methyl-pyridine 1-oxide

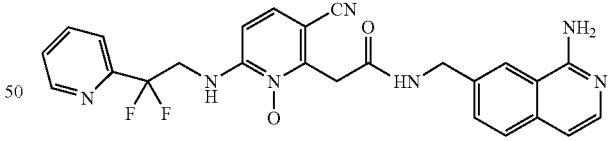

The Boc-protected intermediate [7-({2-[3-cyano-6-(2,2-difluoro-2-pyridin-2-yl-ethylamino)-1-hydroxy-pyridin-2-yl]-acetylamino}-methyl)-isoquinolin-1-yl]-di-carbamic acid di-tert-butyl ester (45 mg, 0.065 mmol) was dissolved in 5 mL of CH$_2$Cl$_2$. Into this solution was added 1 mL of TFA at 0° C. and then the mixture was warmed up to rt for 5 h. The reaction was quenched with 28% NH$_3$ aq. solution. After removal of solvent the residue was loaded to a flash column. The column was washed with 0-5% MeOH (2M NH$_3$ in MeOH) in CH$_2$Cl$_2$. The yellow solid product N-(1-amino-isoquinolin-7-ylmethyl)-2-[3-cyano-6-(2,2-difluoro-2-pyridin-2-yl-ethylamino)-1-oxy-pyridin-2-yl]-acetamide (27 mg, 85% yield) was obtained. $^1$H-NMR (300 MHz, DMSO-d$_6$) δ 8.74 (d, 1H), 8.18 (t, 1H), 8.04 (m, 2H), 7.85 (m, 6H), 7.13 (d, 2H), 6.89 (d, 1H), 6.70 (s, 1H), 4.40 (m, 4H), 4.02 (s, 2H); LC/MS (ESI): calcd mass 489.2, found 490.1 (MH)+.

EXAMPLE 6

3-cyano-6-(2,2-difluoro-2-pyridin-2-yl-ethylamino)-2-(4-[1,2,4]triazol-1-yl-pyridin-3-ylmethyl)aminocarbonylmethyl-pyridine 1-oxide (Cpd 6)

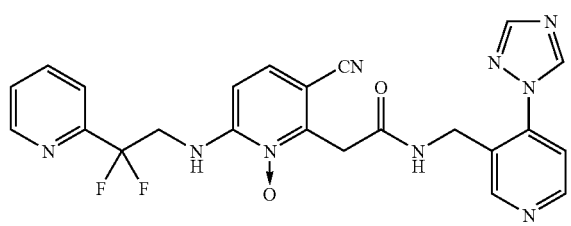

Step A 3-cyano-6-hydroxy-pyridin-2-ol Anion, Sodium Salt

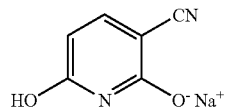

Ethyl propiolate (75.74 g, 0.772 mol) was added dropwise over 20 min to an off-white thick slurry of 2-cyanoacetamide (64.9 g, 0.772 mol) in 3.83 M NaOMe/MeOH (201 mL, 0.770 mol) with stirring at 0° C. (few or no "chunks" of 2-cyanoacetamide were visible upon commencement of ethyl propiolate addition). The resulting mustard yellow slurry was stirred at 0° C. for 2.5 h, at which point the reaction became an immobile yellow paste. Additional dry MeOH was added (50 mL), and the reaction flask was fitted with a reflux condenser and CaSO4 drying tube, and heated at 60° C. for 15 min and 90° C. for 1 h, with occasional manual swirling. The reaction was then allowed to cool to rt, and the yellow paste was filtered. The filter cake was washed with dry MeOH (3×100 mL) and then dried under vacuum at 90° C. to afford, after grinding with mortar and pestle, the title compound (the site of sodium counterion was not definitively assigned) as a free-flowing yellow powder (102.34 g, 84%).

Step B 2,6-dichloro-nicotinonitrile

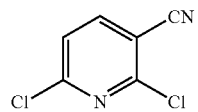

A dry mixture of powdered 3-cyano-6-hydroxy-pyridin-2-ol anion, sodium salt (102.34 g, 0.648 mol), as prepared in the previous step, and triethylamine hydrochloride (89.20 g, 0.648 mol) was swirled until the two components appeared completely mixed. This dry mixture was then cooled on an ice bath while POCl3 (150 mL, 1.62 mol) was slowly poured in under air with intermittent swirling. Triethylamine (90.3 mL, 0.648 mol) was then added rapidly in 2 mL portions with frequent manual swirling while cooling on an ice bath. The flask containing the resulting warm dark semi-solid was then fitted with a reflux condenser and CaSO4 drying tube and stirred under air at 140° C. for 20 h. The easily stirred dark brown thick "solution" was then allowed to cool to rt, chilled on an ice bath, diluted with ether (800 mL), and washed with ice (800 mL). The very dark organic layer was washed with ice water (1×1 L), and the aqueous layers were combined and extracted with ether (3×1 L). The combined ether extracts were concentrated under reduced pressure to give a wet orange-brown solid. This was dissolved in DCM (1 L), dried (2×Na2SO4), and concentrated under reduced pressure at 60° C. to afford the title compound as a brown solid (80.7 g, 466 mmol).

Step C

Malonic Acid Dimethyl Ester, Sodium Salt

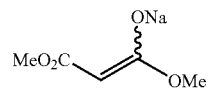

Dimethyl malonate (15.38 g, 116 mmol) was rapidly added in 2 mL portions to an open flask, with manual swirling, containing a mixture of NaH (2.94 g, 116 mmol) in dry ether (90 mL) chilled on a −78° C. bath. Residual dimethyl malonate was transferred with ether (10 mL), and immediately following completion of dimethyl malonate addition the flask was stoppered with an empty balloon outlet (for release of H2 gas pressure) and swirled in the −78° C. bath for an additional minute. The flask was then placed in a 0° C. bath with swirling, and dramatic gas evolution resulted (the flask was periodically placed in the −78° C. flask to moderate the exotherm). After the bulk of H2 gas evolution had occurred (about 20 min after dimethyl malonate addition), the flask containing the resulting light gray paste was rotated at rt for 1 h on the rotary evaporator (without vacuum) to facilitate mixing. It was then concentrated under reduced pressure at 70° C. to afford, after grinding with mortar and pestle, the title compound as a relatively non-hygroscopic off-white powder (16.79 g, 109 mmol).

Step D (6-chloro-3-cyano-pyridin-2-yl)-acetic Acid

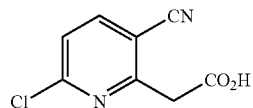

A mixture of malonic acid dimethyl ester, sodium salt (8.067 g, 52.4 mmol), as prepared in the previous step, 2,6-dichloro-nicotinonitrile (4.53 g, 26.2 mmol), as prepared in Example 6b, and dioxane (40 mL) was stirred at 80° C. for 1 h. The resulting easily stirred reddish-brown opaque thin slurry was allowed to cool to rt, 6 M HCl (aq) (80 mL) was added, and the mixture was vigorously stirred at 65-70° C. for 5 h open to air. The resulting clear dark amber solution containing a small amount of dark material was allowed to cool to rt, diluted with water (80 mL), and extracted with DCM (3×100 mL). The organic layers were combined, dried (2×Na$_2$SO$_4$), and concentrated under reduced pressure at 60° C. to provide the crude title compound as a dark brown oil (6.2 g, quantitative yield). A NMR spectrum of the reaction following malonate addition indicated a ~1:2 mixture of desired/undesired regioisomers.

Step E (6-chloro-3-cyano-pyridin-2-yl)-acetic Acid 4-nitro-phenyl Ester

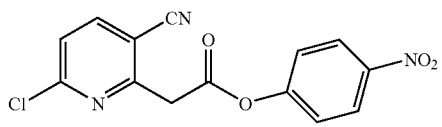

Diisopropylcarbodiimide (3.00 mL, 19.2 mmol) was added dropwise over 2 min at 0° C. with stirring to a homogeneous dark amber solution of crude (6-chloro-3-cyano-pyridin-2-yl)-acetic acid (3.1 g, 16 mmol; mixture of regioisomers), as prepared in the previous step, p-nitrophenol (3.35 g, 24 mmol), DMAP (11 mg, 0.8 mmol) and DCM (20 mL). The ice bath was removed immediately following the completion of DIC addition, and the dark amber solution was stirred at rt overnight. The crude reaction was allowed to stand at rt for some time, and was then loaded directly onto a silica flash column (90 mm×6"). Elution with 97:3 toluene/acetone afforded the impure title compound, but as a single regioisomer (566 mg, 14% from 2,6-dichloro-nicotinonitrile).

Step F 6-chloro-3-cyano-2-(4-nitro-phenoxycarbonylmethyl)-pyridine 1-oxide

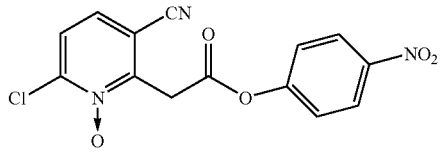

Solid sodium percarbonate (555 mg, 5.30 mmol H$_2$O$_2$) (Na$_2$CO$_3$·1.5 H$_2$O$_2$, approximately 25% H$_2$O$_2$, Aldrich) was added in one portion under air with stirring to a rt solution of (6-chloro-3-cyano-pyridin-2-yl)-acetic acid 4-nitro-phenyl ester (566 mg, 1.78 mmol), as prepared in the previous step, in CH$_3$CN (13.5 mL) and the slurry was then stirred on an ice bath for 5-10 min. The flask was fitted with an argon needle outlet to prevent pressure build-up, and triflic anhydride (7.58 g, 26.9 mmol) was added dropwise with stirring at 0° C. over about 4 min. The reaction was stirred at 0° C. for 3.5 h, and was then poured into 0° C. saturated NaHCO$_3$ (80 mL), with the residual yellow reaction mixture transferred with DCM (2×10 mL). The ice-cold bilayer was stirred at 0° C. for 30 min, and the light yellow organic layer was saved. The dark yellow upper aqueous layer was extracted with DCM (2×40 mL), the organic layers were combined, dried (Na$_2$SO$_4$), and concentrated to provide 463 mg of the crude title compound as a tan solid. This material was combined with a separately-prepared batch of crude title compound (250 mg), and the whole was dissolved in EtOAc (~20 mL) and concentrated under reduced pressure in the presence of silica gel (2.7 g) to afford a free-flowing powder. This silica-adsorbed material was flash chromatographed (2:1 toluene/EtOAc eluent) to afford the title compound as a beige solid [319 mg, 35% (calculated from the 463 mg crude)].

Another batch was prepared as follows: To a suspension of (6-chloro-3-cyano-pyridin-2-yl)-acetic acid 4-nitro-phenyl ester (157 mg, 0.5 mmol) and sodium percarbonate (157 mg, 1.0 mmol) in anhydrous acetonitrile (4 mL), cooled in an ice-water bath, was added trifluoromethanesulfonic anhydride dropwise (253 µL, 1.5 mmol). The reaction mixture turned into a translucent light yellow solution. After stirring for 3 hrs in ice-water bath, the reaction mixture was poured into saturated sodium carbonate solution (30 mL) and cooled in an ice-water bath. The reaction vial was rinsed with DCM and poured into the sodium carbonate solution. After stirring for 25 min in the ice-water bath, the organic layer was separated. The aqueous layer was further extracted with DCM (2×15 mL). The combined organic layers were dried over anhydrous sodium sulfate. After rotary evaporation of most solvent, the concentrated solution was loaded on a preparative silica TLC (2 mm, 20×20 cm) and developed with EtOAc/Hexane (1:1). The title compound was obtained as a light yellow solid (108 mg, 65%). $^1$H-NMR (300 MHz, CDCl$_3$) δ 8.29 (d, 2H), 7.68 (d, 1H), 7.51 (d, 1H), 7.31 (d, 2H), 4.40 (d, 2H).

Step G

4-[1,2,4]triazol-1-yl-nicotinonitrile

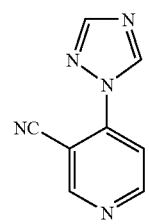

A mixture of known 4-chloro-nicotinonitrile (3.325 g, 24 mmol) (*Tetrahedron Lett.* 46:135-137, 2005), 1H-[1,2,4]triazole (1.99 g, 28.8 mmol), and CsCO$_3$ (9.30 g, 28.5 mmol) in DMSO (5.0 mL) was stirred at 55° C. for 1.5 h. The resulting thin light brown slurry was shaken with water (50 mL) and extracted with DCM (1×50 mL, 2×25 mL). The organic layers were combined, dried (Na$_2$SO$_4$), and concentrated under vacuum at 90° C. to afford the title compound as a beige solid (3.38 g, 82%).

Step H (4-[1,2,4]triazol-1-yl-pyridin-3-yl)-methylamine

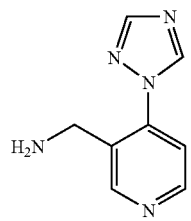

A mixture of dry 2-propanol (35 mL) and CaSO$_4$ (3.5 g, −325 mesh) was bubbled with NH$_3$ gas for 3 min, and was then resuspended and poured onto 4-[1,2,4]triazol-1-yl-nicotinonitrile (300 mg, 1.75 mmol), as prepared in the previous step. This mixture was treated with a suspension of Raney Nickel 2800 in 2-propanol under air (14 mL, prepared from the Aldrich water slurry by decantation of the water and repeated resuspension in and decantation of 2×20 mL 2-propanol, followed by final resuspension in 20 mL 2-propanol). The flask was then sealed and evacuated until bubbles formed, and the evacuated flask was flushed with H$_2$ gas via balloon pressure. After 9 h stirring at rt under balloon H$_2$ pressure, a NMR spectrum of a worked-up aliquot revealed >95% pure title compound, with no starting material remaining. The bulk of the Raney nickel was removed with a magnet, the reaction mixture was filtered, and the clear yellow filtrate was concentrated to give a greenish-yellow oil. This was dissolved in DCM (6 mL) and washed with 0.75 M tetrasodium EDTA (1×6 mL). The aqueous layer was back-extracted with DCM (1×6 mL), EtOAc (2×6 mL), and CH$_3$CN (2×6 mL), and the combined organic layers were dried (Na$_2$SO$_4$) and concentrated under vacuum at 60° C. to provide the title compound as a yellow solid (236 mg, 77%).

Step I 3-cyano-6-chloro-2-(4-[1,2,4]triazol-1-yl-pyridin-3-ylmethyl)aminocarbonylmethyl-pyridine 1-oxide

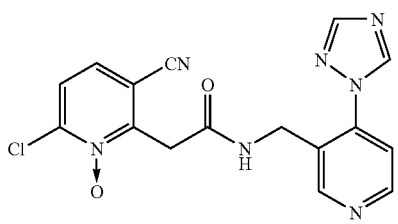

A mixture of 6-chloro-3-cyano-2-(4-nitro-phenoxycarbonylmethyl)-pyridine 1-oxide (150.5 mg, 451 µmol), as prepared in Example 6f, and 82.2 mg (4-[1,2,4]triazol-1-yl-pyridin-3-yl)-methylamine (470 µmol), as prepared in the previous step, in CDCl$_3$ (0.6 mL) was stirred at rt for 4 h. The resulting clear orange-amber solution was directly loaded onto a silica flash column (10 mm×6″) and eluted with CH$_3$CN→97:3 CH$_3$CN/MeOH→9:1 CH$_3$CN/MeOH. The relevant fractions were combined, concentrated, taken up in minimal DCM, and filtered (0.22 µm) to remove silica gel. Concentration of the filtrate yielded the title compound as a white foam (96.9 mg, 58%).

Step J 3-cyano-6-(2,2-difluoro-2-pyridin-2-yl-ethylamino)-2-(4-[1,2,4]triazol-1-yl-pyridin-3-ylmethyl)aminocarbonylmethyl-pyridine 1-oxide

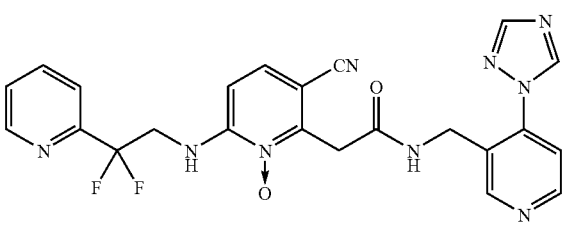

A mixture of 2-(6-chloro-3-cyano-1-oxy-pyridin-2-yl)-N-(4-[1,2,4]triazol-1-yl-pyridin-3-ylmethyl)-acetamide (28.9 mg, 78.2 µmol), as prepared in the previous step, and 2,2-difluoro-2-pyridin-2-yl-ethylamine (25.5 mg, 161 µmol) (see Example 11) in DMSO (80 µL) was stirred at 100° C. for 2.5 h. The homogeneous dark solution then sat at rt for 5 days, at which point the title compound formed crystals. The crude DMSO reaction containing crystalline title compound was diluted with 95:5 CH$_3$CN/MeOH (2 mL), and the supernatant decanted. The crystals were then washed with CH$_3$CN (2×2 mL) and dried under vacuum to afford the title compound as dark red crystals (14.4 mg, 38%). $^1$H-NMR (300 MHz, DMSO-d6) δ 9.11 (s, 1H), 8.78 (m, 2H), 8.72 (m, 1H), 8.66 (d, 1H), 8.32 (s, 1H), 8.28 (m, 1H), 8.00 (dt, 1H), 7.74 (td, 1H), 7.66 (d, 1H), 7.61 (d, 1H), 7.07 (d, 1H), 7.61-7.56 (m, 1H), 4.44 (d, 2H), 4.35 (dt, 2H), 3.91 (s, 2H). LC/MS (ESI): calcd mass 491.2. found 492 (MH)$^+$.

EXAMPLE 7

3-cyano-6-(2,2-difluoro-2-pyridin-2-yl-ethylamino)-2-(2-[1,2,4]triazol-1-yl-6-fluoro-phenylmethyl)aminocarbonylmethyl-pyridine 1-oxide (Cpd 7)

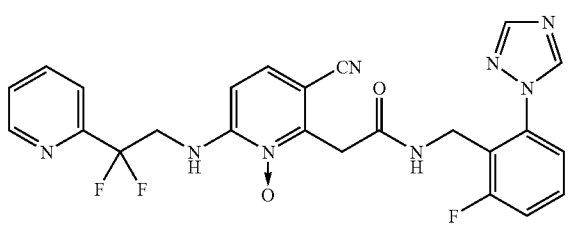

Step A 2-fluoro-6-[1,2,4]triazol-1-yl-benzonitrile

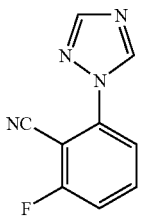

A mixture of 2,6-difluoro-benzonitrile (10.34 g, 74.4 mmol), 1H-[1,2,4]triazole (5.34 g, 77.4 mmol), and CsCO₃ (25.19 g, 77.4 mmol) in DMSO (30 mL) was stirred at ~50° C. for 24 h. The yellowish easily stirred slurry was then diluted with water (200 mL), stirred at rt for 15 min, and filtered. The filter cake was washed with water (1×100 mL) and the filter cake was then partitioned with water (100 mL) and DCM (200 mL). The aqueous layer was extracted with DCM (1×300 mL), and the organic layers were combined, washed with 4 M NaCl (1×100 mL), dried (Na₂SO₄), and concentrated under vacuum at 90° C. to provide the crude title compound as an off-white solid (8.96 g). A portion of this crude material (3.33 g) was dissolved in DCM/MeOH, silica gel (8.5 g) was added, and the mixture was concentrated to a free-flowing powder. The silica-adsorbed crude title compound was applied to a silica flash column (40 mm×6") and eluted with EtOAc to afford the title compound as a white solid [1.60 g, 31% (calculated from chromatographic purification of a portion of the crude material)].

Step B 2-fluoro-6-[1,2,4]triazol-1-yl-benzylamine

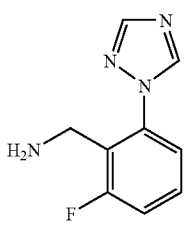

A solution of 2-fluoro-6-[1,2,4]triazol-1-yl-benzonitrile (1.54 g, 8.20 mmol), as prepared in the previous step, in dry EtOH (70 mL) was bubbled with NH₃ gas for 5 min. This solution was treated with a suspension of Raney Nickel 2800 in EtOH under air (15 mL) (prepared by diluting 2 mL of the Aldrich water slurry with 15 mL EtOH, centrifuging, decanting, diluting with 15 mL EtOH and transferring to the reaction). The flask was then sealed and evacuated until bubbles formed, and the evacuated flask was flushed with H₂ gas via balloon pressure. After 14 h stirring at rt under balloon H₂ pressure, TLC demonstrated very little starting material remaining. The bulk of the Raney nickel was removed with a magnet, the reaction mixture was filtered (0.22 μm), and the clear pale yellow filtrate was concentrated to give a green oil. Silica flash chromatography of the crude oil (40 mm×6" column; 98:2 DCM/MeOH/saturated NH₃ eluent; 30 mL fractions; fractions 12-19 combined) afforded the title compound as a yellow solid (1.41 g, 89%).

Step C 3-cyano-6-(2,2-difluoro-2-pyridin-2-yl-ethylamino)-2-(2-[1,2,4]triazol-1-yl-6-fluoro-phenylmethyl)aminocarbonylmethyl-pyridine 1-oxide

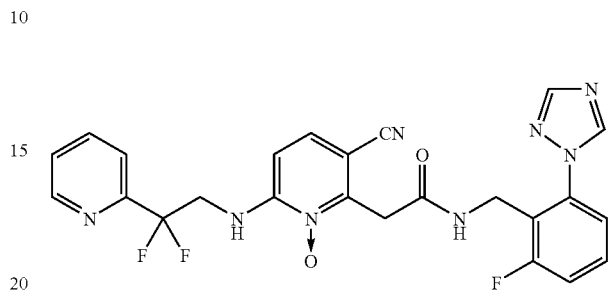

The title compound was prepared as described for Example 6i-j, using 2-fluoro-6-[1,2,4]triazol-1-yl-benzylamine, as prepared in the previous step, except the title compound was purified by silica flash chromatography of the crude reaction (first column eluent 4:1 DCM/CH₃CN/saturated NH₃; second column eluent 95:5 CH₃CN/MeOH). ¹H-NMR (300 MHz, CDCl₃) δ 8.68 (qd, 1H), 8.44 (s, 1H), 8.08 (s, 1H), 7.98 (br t, 1H), 7.89 (br t, 1H), 7.86 (dt, 1H), 7.72 (td, 1H), 7.48-7.36 (m, 3H), 7.20 (m, 1H), 7.12 (td, 1H), 6.86 (d, 1H), 4.41-4.26 (m, 4H), 4.01 (s, 2H). LC/MS (ESI): calcd mass 508.2. found 509.1 (MH)⁺.

EXAMPLE 8

3-cyano-6-(2,2-difluoro-2-(4-fluoro-phenyl)-ethylamino)-2-(4-[1,2,4]triazol-1-yl-pyridin-3-ylmethyl)aminocarbonylmethyl-pyridine 1-oxide (Cpd 8)

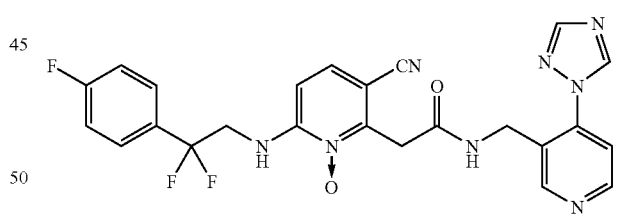

The title compound was prepared as described for Example 6j, using 2,2-difluoro-2-(4-fluoro-phenyl)-ethylamine (WO 2004/091613 A2; prepared from 1-fluoro-4-iodobenzene as described in detail for 1-chloro-3-iodobenzene), to provide the precipitated title compound (19.7 mg, 34%). Silica flash chromatography of the combined supernatants (10 mm×6" column; 95:5 CH₃CN/MeOH eluent; 5 mL fractions; fractions 14-32 combined) yielded an additional amount of title compound (25.0 mg; 44.7 mg total; 77% total yield). ¹H-NMR (300 MHz, DMSO-d6) δ 9.13 (s, 1H), 8.80 (m, 2H), 8.67 (d, 1H), 8.34 (s, 1H), 8.24 (br s, 1H), 7.69-7.61 (m, 4H), 7.35 (t, 2H), 7.13 (d, 1H), 4.45 (d, 1H), 4.21 (dt, 2H), 3.93 (s, 1H). LC/MS (ESI): calc mass 508.2. found 509.1 (MH)⁺.

EXAMPLE 9

3-cyano-6-(2,2-difluoro-2-pyrimidin-2-yl-ethylamino)-2-(4-[1,2,4]triazol-1-yl-pyridin-3-ylmethyl)aminocarbonylmethyl-pyridine 1-oxide (Cpd 9)

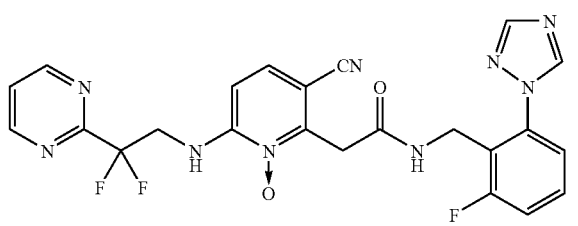

Step A

Difluoro-pyrimidin-2-yl-acetic Acid Ethyl Ester

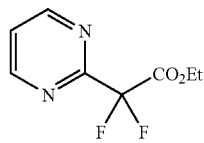

A mixture of copper bronze (Aldrich) (5.88 g, 92.5 mmol), DMSO (10 mL), and bromo-difluoro-acetic acid ethyl ester (Advanced Synthesis Technologies) (6.46 mL, 50.4 mmol) was evacuated and flushed with argon three times, and was then stirred at rt for 1 h. Upon standing, the supernatant was dark green. Solid 2-iodopyrimidine (8.76 g, 42.5 mmol) (*J. Org. Chem.* 67:6550, 2002) was then added, the flask was again evacuated and flushed with argon three times, and stirred at rt for 14 h (mild initial warming of flask spontaneously occurred). The resulting immobile dark brown paste was diluted with saturated NH$_4$Cl (175 mL) and EtOAc (150 mL), the mixture was filtered through a pad of Celite, and the filter cake washed with EtOAc (2×50 mL). The blue aqueous layer was extracted with EtOAc (1×50 mL), and the combined filtrate clear yellow organic layers were washed with saturated NH$_4$Cl (2×100 mL), 10% w/v EDTA trisodium (1×100 mL; saturated NaBr needed to break phases), saturated NaCl (1×50 mL), saturated NaBr (1×20 mL), dried (2×Na$_2$SO$_4$), and concentrated under reduced pressure. Silica flash chromatography of the greenish residue (1:1 hexanes/EtOAc eluent) provided the title compound as a nearly colorless oil with a greenish precipitate (1.75 g, 20%).

Step B 2,2-difluoro-2-pyrimidin-2-yl-ethanol

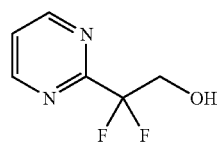

A solution of difluoro-pyrimidin-2-yl-acetic acid ethyl ester (1.75 g, 8.65 mmol), as prepared in the previous step (and containing undissolved green precipitate), in anhydrous absolute EtOH (18 mL) was stirred at 0° C. for 5 min, and was then treated with solid NaBH$_4$ (655 mg, 17.3 mmol) in one slow steady portion at 0° C. Bubbles immediately formed, and the solution turned light amber. Stirring continued at 0° C. for 2 h, and the reaction was then quenched with half-saturated NH$_4$Cl (40 mL) and extracted with EtOAc (2×15 mL). The organic phases were combined, washed with saturated NaCl (1×10 mL), dried (Na$_2$SO$_4$), and concentrated to give the title compound as a yellow oil (696 mg, 50%).

Step C 2-(1,1-difluoro-2-iodo-ethyl)-pyrimidine

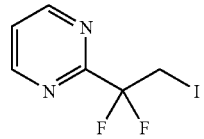

A homogeneous solution of 2,2-difluoro-2-pyrimidin-2-yl-ethanol (689 mg, 4.31 mmol), as prepared in the previous step, PPh$_3$ (1.69 g, 6.44 mmol), and imidazole (590 mg, 8.67 mmol) in toluene (5.8 mL) and CH$_3$CN (2.9 mL) was stirred at 0° C. for 5 min, and was then treated with I$_2$ (1.61 g, 6.34 mmol) in two portions and stirred at 0° C. for another 5 min. The resulting brown opaque slurry was then heated at 90° C. for 19 h, and then allowed to cool to rt. The mixture was filtered, the beige filter cake was washed with toluene (3×10 mL), and the combined brown filtrates were concentrated. Silica flash chromatography of the residue (2:1 hex/EtOAc eluent) afforded the title compound as a pale yellow oil (849 mg, 73%).

Step D. 2,2-difluoro-2-pyrimidin-2-yl-ethylamine

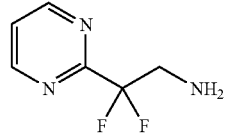

A mixture of 2-(1,1-difluoro-2-iodo-ethyl)-pyrimidine (841 mg, 3.11 mmol), as prepared in the previous step, NaN$_3$ (338 mg, 5.19 mmol), and DMSO (2.35 mL) was stirred at 95° C. for 3 days. The reaction was then shaken with water (10 mL) and extracted with ether (3×8 mL). The organic layers were combined, dried (Na$_2$SO$_4$), and concentrated to give the intermediate 2-(2-azido-1,1-difluoro-ethyl)-pyrimidine as a clear yellow oil (591 mg) that was immediately used in the next step without further purification or characterization.

A portion of the 2-(2-azido-1,1-difluoro-ethyl)-pyrimidine (578 mg, 3.12 mmol) was taken up in THF (8 mL), 0.1 M NaOH (aq) (0.6 mL), and PPh$_3$ (982 mg, 3.74 mmol) and stirred at 50° C. for 29 h. The resulting pale yellow solution was allowed to cool to rt, dried (2×Na$_2$SO$_4$), and treated with 4 M HCl/dioxane (2 mL; approximately 8 mmol HCl). The precipitate was collected by decantation, and washed with dry ether (3×15 mL). The solid was then partitioned with 4 M NaCl (4 mL) and EtOAc (4 mL), and the aqueous layer was washed with EtOAc (1×4 mL). The aqueous layer was then brought to a pH greater than 10 with 2.5 M NaOH, and extracted with equal volumes of DCM (3×5 mL). The combined organic layers were dried (Na$_2$SO$_4$) and concentrated under rotary evaporation at 35° C. to provide the title compound as a pale yellow oil (419 mg, 85% over two steps).

Step E 3-cyano-6-(2,2-difluoro-2-pyrimidin-2-yl-ethylamino)-2-(4-[1,2,4]triazol-1-yl-pyridin-3-ylmethyl)aminocarbonylmethyl-pyridine 1-oxide

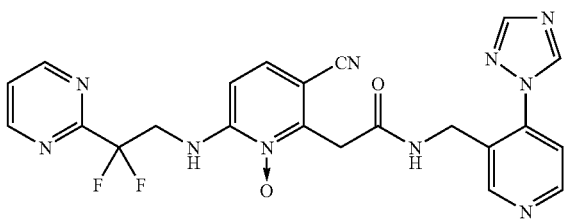

The title compound was prepared as described for Example 6j using 3.4 equivalents of 2,2-difluoro-2-pyrimidin-2-yl-ethylamine, prepared as described in the previous step. Silica flash chromatography (10 mm×6" column; 94:6→9:1 CH$_3$CN/MeOH eluent; 5 mL fractions; fractions 48-62 combined) provided the title compound as a yellow solid (14.8 mg, 83%). $^1$H-NMR (300 MHz, DMSO-d6) δ 9.12 (s, 1H), 9.02 (d, 1H), 8.80 (s, 1H), 8.80 (br t, 1H), 8.67 (d, 1H), 8.33 (s, 1H), 8.32 (br t, 1H), 7.74 (t, 1H), 7.69 (d, 1H), 7.62 (dd, 1H), 7.11 (d, 1H), 4.50-4.36 (m, 4H), 3.92 (s, 2H). LC/MS (ESI): calc mass 492.2. found 493.1 (MH)$^+$.

EXAMPLE 10

3-cyano-6-(2,2-difluoro-2-pyridin-2-yl-ethylamino)-2-(2-[1,2,4]triazol-1-yl-pyridin-3-ylmethyl)aminocarbonylmethyl-pyridine 1-oxide (Cpd 10)

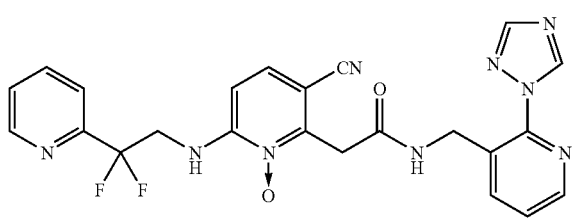

Step A

2-[1,2,4]triazol-1-yl-nicotinonitrile

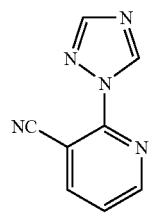

A mixture of 2-chloro-nicotinonitrile (10.30 g, 74.4 mmol), 1H-[1,2,4]Triazole (5.36 g, 77.6 mmol), and Cs$_2$CO$_3$ (25.28 g, 77.6 mmol) in DMSO (30 mL) was stirred at 50° C. for C for 30 min. The resulting off-white semisolid was partitioned with water (600 mL) and DCM (600 mL), and the aq layer was extracted with DCM (2×200 mL). The combined organic layers were dried (Na$_2$SO$_4$), concentrated, and put under vacuum at 90° C. to remove the bulk of DMSO. The resulting white solid was briefly triturated with refluxing diethyl ether (100 mL), allowed to cool to rt, and filtered. The filter cake was washed with ether (3×50 mL) and dried to yield the title compound as white fluffy needles (11.37 g, 89%).

Step B

C-(2-[1,2,4]triazol-1-yl-pyridin-3-yl)-methylamine

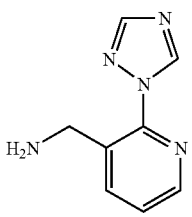

A catalytic amount of Raney 2800 nickel in water (Aldrich; withdrawn as a wet slurry with the tip of a spatula) was added under air to a translucent slurry of 2-[1,2,4]triazol-1-yl-nicotinonitrile (1.053 g, 6.16 mmol), as prepared in the previous step, in 2 M NH$_3$/MeOH (50 mL). The flask was then sealed with a septum, the air was removed from the system, and the flask was flushed with H$_2$ gas under balloon pressure. The reaction was stirred at rt under H$_2$ for 11 h (TLC showed no starting material remained), and the bulk of the Raney nickel was then removed with a magnet. The translucent white reaction mixture was then diluted with DCM (50 mL), filtered, and the translucent filtrate was concentrated under vacuum to provide the title compound as a beige crystalline solid (988 mg, 92%).

Step C 3-cyano-6-(2,2-difluoro-2-pyridin-2-yl-ethylamino)-2-(2-[1,2,4]triazol-1-yl-pyridin-3-ylmethyl)aminocarbonylmethyl-pyridine 1-oxide

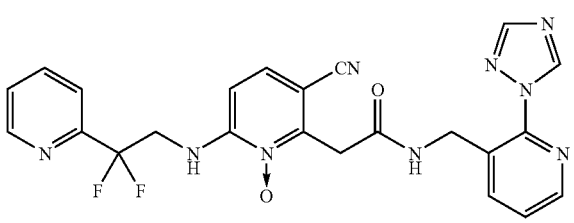

The title compound was prepared as described for Example 6i-j, using C-(2-[1,2,4]triazol-1-yl-pyridin-3-yl)-methylamine, as prepared in the previous step. The title compound was purified as follows: The crude DMSO reaction was allowed to cool to rt, diluted with CDCl$_3$ (0.4 mL), and the homogeneous solution was directly loaded onto a silica flash column (10 mm×6"). Elution with 2:1 DCM/CH$_3$CN/saturated NH$_3$ (5 mL fractions; fractions 12-13 combined), and concentration under vacuum at 90° C. to remove DMSO afforded the title compound as a beige powder (20.7 mg, 70%). $^1$H-NMR (300 MHz, DMSO-d6) δ 9.16 (s, 1H), 8.80 (m, 1H), 8.73 (m, 1H), 8.48 (dd, 1H), 8.33 (m, 1H), 8.30 (s, 1H), 8.15 (dd, 1H), 8.02 (m, H), 7.76 (td, 1H), 7.68 (d, 1H), 7.61 (m, 1H), 7.53 (dd, 1H), 7.10 (d, 1H), 4.49 (d, 2H), 4.37 (dt, 2H), 3.95 (s, 2H). LC/MS (ESI): calc mass 491.2. found 492.5 (MH)$^+$.

EXAMPLE 11

N-{2-[(aminoiminomethyl)aminooxy]ethyl}-2-[3-chloro-6-(2,2-difluoro-2-phenyl-ethylamino)-pyridin-2-yl]-acetamide (Cpd 11)

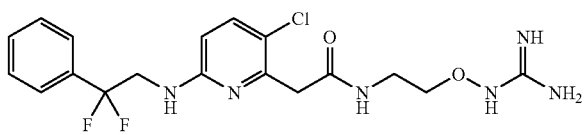

The title compound was prepared as described in Example 2f, except [3-chloro-6-(2,2-difluoro-2-phenyl-ethylamino)-pyridin-2-yl]-acetic acid phenyl ester, prepared as described in Example 2c, was used in place of [3-chloro-6-(2,2-difluoro-2-phenyl-ethylamino)-1-oxy-pyridin-2-yl]-acetic acid phenyl ester. Silica flash chromatography (95:5 DCM/MeOH/saturated NH$_3$ eluent) afforded the title compound as a white solid (2.4 mg, 11%). $^1$H-NMR (300 MHz, CD$_3$OD) δ 7.56-7.51 (m, 2H), 7.44-7.38 (m, 3H), 7.31 (d, 1H), 6.40 (d, 1H), 4.08 (t, J=14.3 Hz, 2H), 3.78 (t, 2H), 3.64 (s, 2H), 3.44 (t, 2H). LC/MS (ESI): calc mass 426.1. found 427 (MH)$^+$.

EXAMPLE 12

3-cyano-6-(2,2-difluoro-2-pyridin-2-yl-ethylamino)-2-(5-chloro-pyridin-3-ylmethyl)aminocarbonylmethyl-pyridine 1-oxide (Cpd 12)

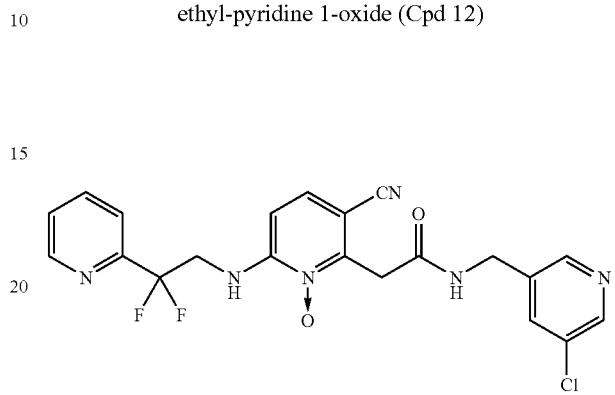

Step A 5-chloro-nicotinonitrile

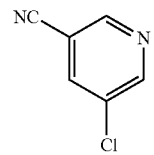

A mixture of 3,5-dichloropyridine (4.23 g, 28.6 mmol), CuCN (3.07 g, 34.3 mmol), and argon-bubbled NMP (8 mL) was placed in a 40 mL scintillation vial, flushed with argon for 1 min, and then quickly capped and stirred under argon at 210° C. for 3 h. The dark brown easily stirred solution was allowed to cool somewhat, and was then poured into concentrated NH$_4$OH (50 mL) on an ice bath, and stirred vigorously for 5 min. DCM (50 mL) was added, the bilayer was stirred for an additional 5 min, and then filtered. The lower dark amber organic layer was saved, and the dark blue aqueous layer was extracted with DCM (2×50 mL). The organic layers were combined and washed with NH$_4$OH (1×30 mL), 4 M NaCl (1×30 mL), dried (Na$_2$SO$_4$), and concentrated to give an amber oil heavily contaminated with NMP. Silica flash chromatography of this residue (90 mm×6" column; 6:1 hex/EtOAc eluent; 100 mL fractions; fractions 15-19 combined) afforded, after rotary evaporation at 40° C., the title compound as brilliant white microcrystals (891 mg, 22%).

Step B

C-(5-chloro-pyridin-3-yl)-methylamine

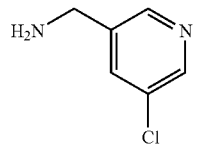

A mixture of 5-chloro-nicotinonitrile (63.8 mg, 461 μmol), 2-propanol (9.2 mL; not dry), and CaSO$_4$ (−325 mesh) (920 mg, 6.76 mmol) was treated with a suspension of Raney Cobalt 2700 in 2-propanol under air (2 mL) (prepared by diluting 2 mL of the commercial water slurry with 15 mL 2-propanol, centrifuging, decanting, and repeating with 2×15 mL 2-propanol, then resuspending with 2 mL 2-propanol). The flask was then sealed and evacuated until bubbles formed, and the evacuated flask was flushed with H$_2$ gas via balloon pressure. After 11 h stirring at rt under balloon H$_2$ pressure, a NMR spectrum of a worked-up reaction aliquot indicated 80% conversion to the title compound. The reaction was then filtered, the filter cake was washed with 2-propanol (3×10 mL), and the combined clear colorless filtrates were concentrated briefly under rotary evaporation at 50° C. The residue was taken up in DCM and concentrated again to afford the volatile crude title compound (53 mg, 81%).

Step C 3-cyano-6-(2,2-difluoro-2-pyridin-2-yl-ethylamino)-2-(5-chloro-pyridin-3-ylmethyl)aminocarbonylm-ethyl-pyridine 1-oxide

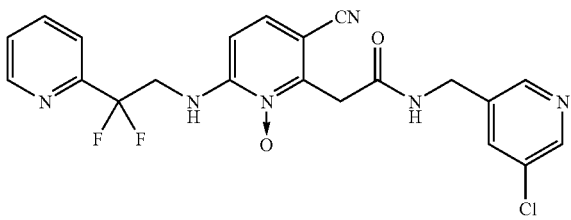

The title compound was prepared as described in Example 6i-j, using C-(5-chloro-pyridin-3-yl)-methylamine, as prepared in the previous step, except the intermediate chloropyidine N-oxide amide was collected by filtration. The product was purified as follows: the homogeneous DMSO reaction solution containing the title compound was allowed to cool to rt and diluted with 95:5 CH$_3$CN/MeOH (2 mL), resulting in the formation of a precipitate. The supernatant was saved, and the precipitate was washed with CH$_3$CN (3×2 mL). The combined supernatants were allowed to slowly evaporate to dryness to provide oily needles. These needles were washed with dry CH$_3$CN (4×2 mL) and dried under vacuum to provide the title compound as yellow needles (14.5 mg, 44%). $^1$H-NMR (300 MHz, DMSO-d6) δ 8.87 (t, 1H), 8.73 (m, 1H), 8.50 (d, 1H), 8.47 (d, 1H), 8.25 (br t, 1H), 8.01 (dt, 1H), 7.88 (m, 1H), 7.76 (td, 1H), 7.70 (d, 1H), 7.61 (m, 1H), 7.11 (d, 1H), 4.45-4.30 (m, 4H), 3.95 (s, 2H). LC/MS (ESI): calc mass 458.1. found 459.0 (MH)$^+$.

Tablet Preparation

Tablets containing 25.0, 50.0, and 100.0 mg, respectively, of the active compound, are prepared as below:

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

Intravenous Solution Preparation

An intravenous dosage form of the above-indicated active compound of Example 1 is prepared as follows:

| | |
|---|---|
| Active Compound | 0.5-10.0 mg |
| Sodium Citrate | 5-50 mg |
| Citric Acid | 1-15 mg |
| Sodium Chloride | 1-8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

In Vitro Inhibition of Purified Enzyme

Reagents: All buffer salts were obtained from Sigma Chemical Company (St. Louis, Mo.), and were of the highest purity available.

Human α-thrombin, was obtained from Enzyme Research Laboratories (South Bend, Ind.).

Kinetic Analysis by Chromogenic Substrates

Compounds were assessed for their inhibitory activity toward Thrombin by kinetic analysis using para-nitroaniline chromogenic substrates monitored at 405 nm. The assay buffer employed was 50 mM HEPES, pH 7.5, 200 mM NaCl, and fresh 0.05% n-octyl β-d-glucopyranoside. DMSO was present at a final concentration of 4%, derived from the substrate and inhibitory compound stock solutions. In a 96-well low binding polystyrene plate, 280 uL of substrate in assay buffer was preincubated at 37° C. for 15 min with 10 μL test compound in DMSO to obtain final test compound concentrations that bracketed the Ki. Reactions were initiated by addition of 10 μL protease, and increase in absorbance due to proteolytic cleavage of substrate was kinetically monitored at 37° C., 405 nm with a Molecular Devices Spectramax 340 plate reader. Initial velocities were determined by analysis of the initial linear portion of the reactions. Plots of $v_o/v_i$ vs. inhibitor concentration, where $v_o$=velocity without inhibitor, and $v_i$=inhibited velocity, were fit to a linear regression line, and IC$_{50}$ was determined from the reciprocal of the slope. Ki was calculated from IC$_{50}$ using the Ki factor specific for the assay as: Ki=IC$_{50}$×Ki factor, or Ki=IC$_{50}$×(1/(1+[S]/Km)), where S is the substrate concentration in the assay, and Km is the Michaelis constant for the substrate (Cheng Y and Prusoff W H (1973) *Biochem Pharmacol* 22: 3099-3108).

The Thrombin assay incorporated substrate SucAAPR pNA (Bachem L-1720, [S]=100 uM final, Km=320 μM, Ki factor=0.76). Substrate in DMSO (10.7 mM) was diluted in assay buffer 100-fold for 100 μM final. Human α-thrombin (Enzyme Research Laboratories HT1002a) was diluted 1500-fold in assay buffer for a final assay concentration of 1.1 nM.

| Cpd | Structure | IC$_{50}$ (nM) |
|---|---|---|
| 1 | 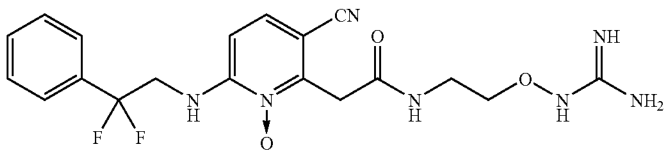 | ~0.13 +/− 0.01 |
| 2 | 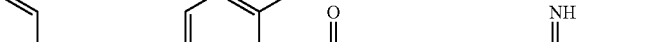 | ~0.54 +/− 0.04 |
| 3 | 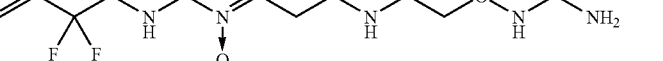 | ~280 |
| 4 | 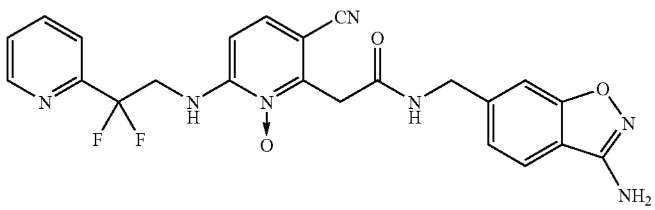 | ~6.1 +/− 0.5 |
| 5 | 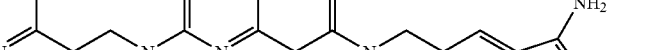 | ~42 |
| 6 | 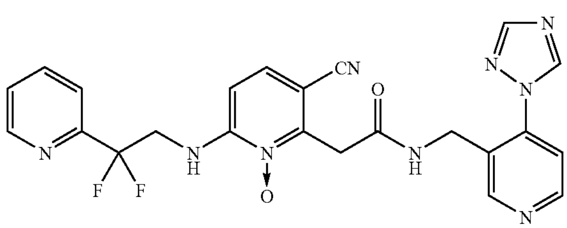 | ~3.3 +/− 0.2 |
| 7 | 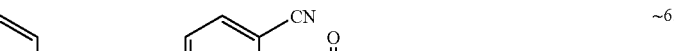 | ~0.44 +/− 0.03 |
| 8 | 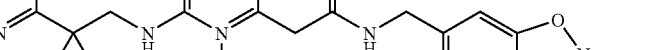 | ~3.4 +/− 0.1 |

-continued

| Cpd | Structure | IC$_{50}$ (nM) |
|---|---|---|
| 9 | 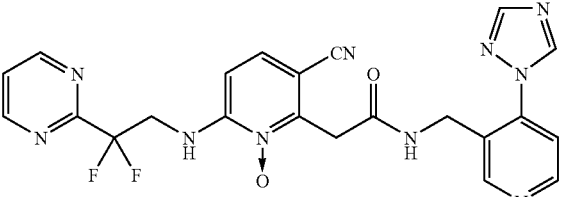 | ~200 +/− 17 |
| 10 | 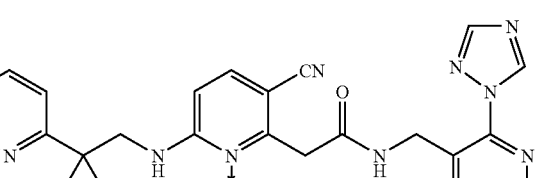 | ~170 |
| 11 | 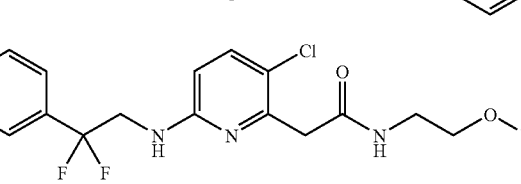 | ~370 |
| 12 | 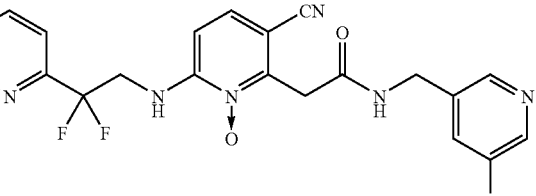 | ~66 +/− 6 |

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of Formula I:

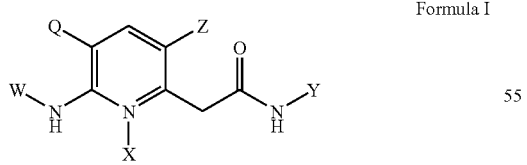

Formula I wherein
Z is H, F, Cl, Br, —CN, C$_{(1-4)}$alkyl, —C≡C—H, —C≡C—CH$_3$, or —C≡C—CH$_2$CH$_3$;
X is absent or oxygen;
Q is H or F;
W is —CH$_2$C(R$^1$)$_2$R$^2$;
R$^1$ is independently hydrogen, C$_{1-4}$ alkyl, halogen, or both R$^1$ may be taken together to form a C$_{(3-6)}$ cycloalkyl ring;

R$^2$ is heterocyclyl, phenyl, 4-fluorophenyl, 4-fluoroheteroaryl, or heteroaryl, wherein said phenyl or 4-fluorophenyl is optionally substituted with one R$^3$; and, R$^3$ is —C$_{(1-4)}$alkyl, —CF$_3$, —Cl, —F, —Br, —CO$_2$H, —CH$_2$CO$_2$H, —CO$_2$Et, —CH$_2$CO$_2$Et, —CH$_2$NHCH$_2$CO$_2$H, —CH$_2$NHCH$_2$CO$_2$Et,

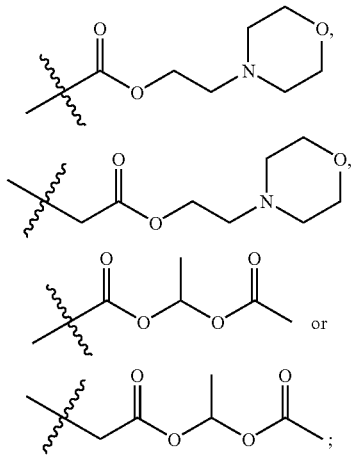

Y is selected from the group consisting of:

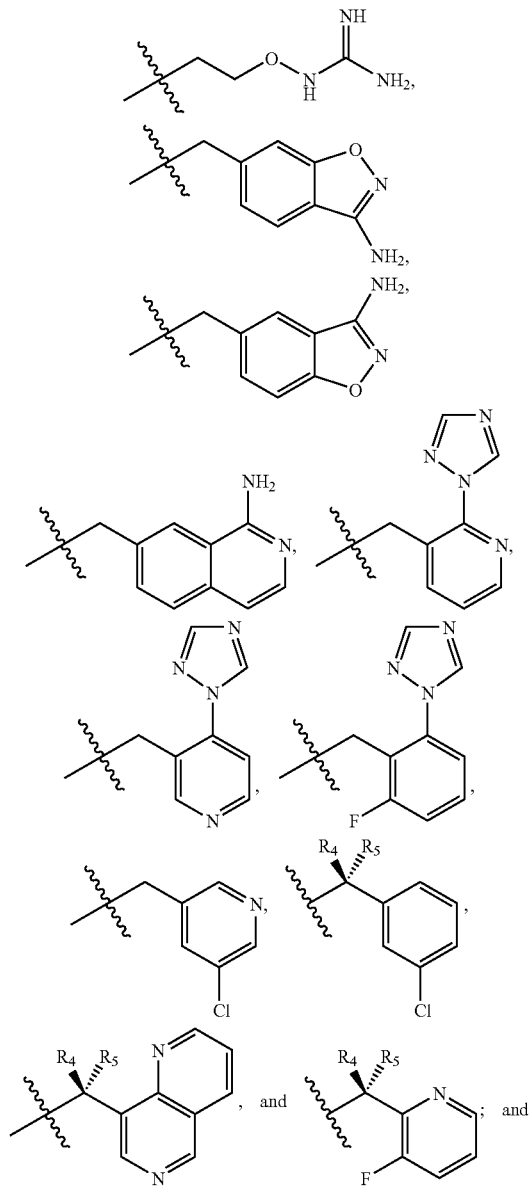
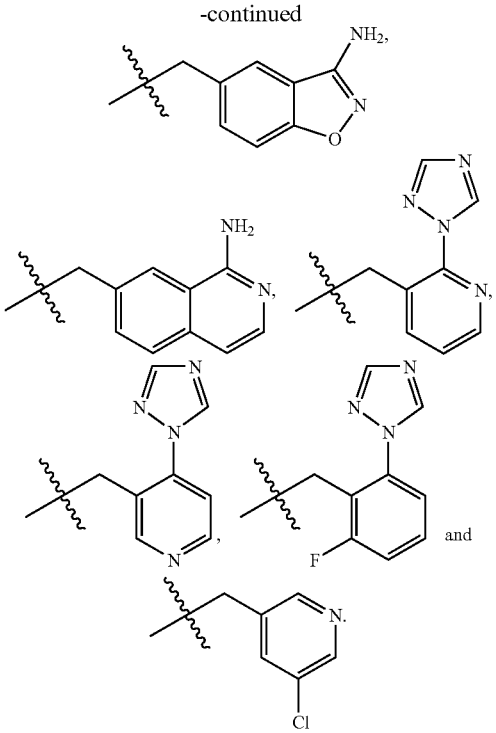

$R_4$ and $R_5$ are independently H or D (deuterium), provided that at least one of $R_4$ and $R_5$ is deuterium.

2. The compound of claim 1, wherein Y is selected from the group consisting of:

3. The compound of claim 2, wherein
W is —CH$_2$C(R$^1$)$_2$R$^2$;
R$^1$ is independently hydrogen, C$_{1-4}$ alkyl, halogen, or both R$^1$ may be taken together to form a C$_{(3-6)}$cycloalkyl ring;
R$^2$ is piperidin-2-yl, phenyl, 4-fluorophenyl, pyrimidyl, pyridinyl, or pyridinyl-N-oxide, wherein said phenyl or 4-fluorophenyl is optionally substituted with one R$^3$; and,
R$^3$ is —C$_{(1-4)}$alky, —CF$_3$, —Cl, —F, —Br, —CO$_2$H, —CH$_2$CO$_2$H, —CO$_2$Et, —CH$_2$CO$_2$Et, —CH$_2$NHCH$_2$CO$_2$H, —CH$_2$NHCH$_2$CO$_2$Et,

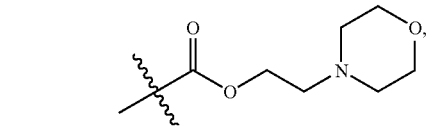

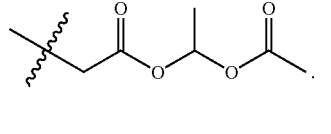

4. The compound of claim 3 wherein
Z is H, F, Cl, Br, —CN, or C$_{(1-4)}$alkyl;
W is —CH$_2$C(R$^1$)$_2$R$^2$;
R$^1$ is independently hydrogen, C$_{1-4}$alkyl, or halogen;

R² is piperidin-2-yl, 4-fluorophenyl, phenyl, pyrimidyl, pyridinyl, or pyridinyl-N-oxide, wherein said phenyl or 4-fluorophenyl is optionally substituted at the ortho position (relative to C(R¹)₂) with one R³; and, R³ is —CO₂H, —CH₂CO₂H, —CO₂Et, —CH₂CO₂Et, CH₂NHCH₂CO₂H, —CH₂NHCH₂CO₂Et,

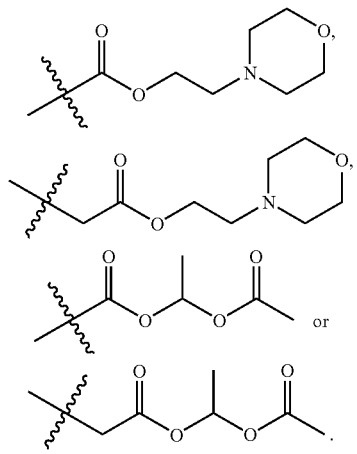

5. The compound of claim 4 wherein
Z is Cl, or —CN;
X is absent or oxygen;
Q is H;
W is —CH₂CF₂R²; and
R² is phenyl, pyrimidyl, 4-fluorophenyl, or pyridyl.

6. A compound selected from the group consisting of:
3-cyano-6-(2,2-difluoro-2-phenyl-ethylamino)-2-{2-[(aminoiminomethyl)aminooxy]ethyl}aminocarbonylmethyl-pyridine 1-oxide,
3-chloro-6-(2,2-difluoro-2-phenyl-ethylamino)-2-{2-[(aminoiminomethyl)aminooxy]ethyl}aminocarbonylmethyl-pyridine 1-oxide,
3-cyano-6-(2,2-difluoro-2-pyridin-2-yl-ethylamino)-2-(3-Amino-benzo[d]isoxazol-5-ylmethyl)aminocarbonylmethyl-pyridine 1-oxide,
3-cyano-6-(2,2-difluoro-2-pyridin-2-yl-ethylamino)-2-(3-amino-benzo[d]isoxazol-6-ylmethyl)aminocarbonylmethyl-pyridine 1-oxide,
3-cyano-6-(2,2-difluoro-2-pyridin-2-yl-ethylamino)-2-(1-Amino-isoquinolin-7-ylmethyl)aminocarbonylmethyl-pyridine 1-oxide,
3-cyano-6-(2,2-difluoro-2-pyridin-2-yl-ethylamino)-2-(4-[1,2,4]triazol-1-yl-pyridin-3-ylmethyl)aminocarbonylmethyl-pyridine 1-oxide,
3-cyano-6-(2,2-difluoro-2-pyridin-2-yl-ethylamino)-2-(2-[1,2,4]triazol-1-yl-6-fluoro-phenylmethyl)aminocarbonylmethyl-pyridine 1-oxide,
3-cyano-6-(2,2-difluoro-2-(4-fluoro-phenyl)-ethylamino)-2-(4-[1,2,4]triazol-1-yl-pyridin-3-ylmethyl)aminocarbonylmethyl-pyridine 1-oxide,
3-cyano-6-(2,2-difluoro-2-pyrimidin-2-yl-ethylamino)-2-(4-[1,2,4]triazol-1-yl-pyridin-3-ylmethyl)aminocarbonylmethyl-pyridine 1-oxide,
3-cyano-6-(2,2-difluoro-2-pyridin-2-yl-ethylamino)-2-(2-[1,2,4]triazol-1-yl-pyridin-3-ylmethyl)aminocarbonylmethyl-pyridine 1-oxide,
N-{2-[(aminoiminomethyl)aminooxy]ethyl}-2-[3-chloro-6-(2,2-difluoro-2-phenyl-ethylamino)-pyridin-2-yl]-acetamide,
3-cyano-6-(2,2-difluoro-2-pyridin-2-yl-ethylamino)-2-(5-chloro-pyridin-3-ylmethyl)aminocarbonylmethyl-pyridine 1-oxide,
and pharmaceutically acceptable salts thereof.

7. A compound selected from the group consisting of:

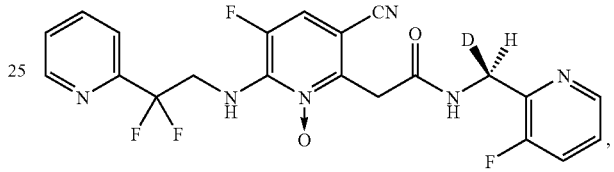

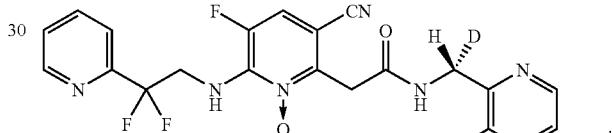

, and

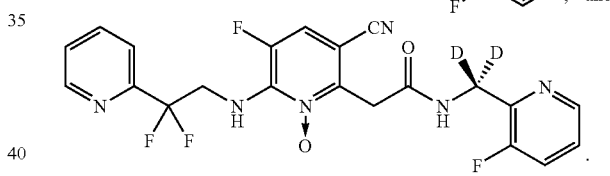

.

8. A pharmaceutical composition, comprising a compound of claim 1 and a pharmaceutically-acceptable carrier.

9. A pharmaceutical composition according to claim 8, further comprising at least one of an anticoagulant, an antiplatelet agent or a thrombolytic agent.

10. A pharmaceutical composition according to claim 8, wherein said compound is present in an amount between about 0.1 and about 500 mg.

* * * * *